US008055451B2

(12) United States Patent
Owczarzy et al.

(10) Patent No.: US 8,055,451 B2
(45) Date of Patent: Nov. 8, 2011

(54) METHOD FOR ESTIMATING A MELTING TEMPERATURE OF A NUCLEIC ACID IN BUFFERS CONTAINING MAGNESIUM IONS

(75) Inventors: Richard Owczarzy, Coralville, IA (US); Bernardo Moreira, Iowa City, IA (US); Yong You, Coralville, IA (US); Mark Aaron Behlke, Coralville, IA (US); Joseph Alan Walder, Chicago, IL (US)

(73) Assignee: Integrated DNA Technologies, Inc., Coralville, IA (US)

( * ) Notice: Subject to any disclaimer, the term of this patent is extended or adjusted under 35 U.S.C. 154(b) by 575 days.

(21) Appl. No.: 11/970,509

(22) Filed: Jan. 7, 2008

(65) Prior Publication Data
US 2009/0198453 A1 Aug. 6, 2009

Related U.S. Application Data

(60) Provisional application No. 60/879,259, filed on Jan. 5, 2007.

(51) Int. Cl.
*C12Q 1/68* (2006.01)
*G01N 33/50* (2006.01)
*G01N 33/48* (2006.01)
*G06G 17/00* (2006.01)

(52) U.S. Cl. .................. 702/19; 702/20; 435/6
(58) Field of Classification Search .................. None
See application file for complete search history.

(56) References Cited

U.S. PATENT DOCUMENTS 5,510,270 A 4/1996 Fodor et al.
6,889,143 B2 5/2005 Behlke et al.

OTHER PUBLICATIONS

Sigel. "Interatctions of Metal Ions with Nucleotides and Nucleic Acids and their Constituents", Chem. Soc. Rev.I 1993, 22:255-267.
Record. Biopolymers 1967, 5:993-1008.
Owczarzy et al.,Effects of Sodium Ions on DNA Duplex Oligomers: Improved Predictions of Melting Temperatures, Biochemistry 2004, 43:3537-3554.
Moreira et al., "Effects of Fluorescent dyes, quenchers, and dangling ends on DNA duplex stability", Biochem. Biophys. Res. Commun. 2005, 327:473-484.
William H. Press et al., Numerical Recipes in C: The Art of Scientific Computing 659-61 (2d Ed. 1992.
Peyret, Ph.D. Thesis, "Prediction of Nucleic Acid Hybridization: Parameters and Algorithms", Wayne State University, Detroit, Michigan, pp. 128, section 5.4.2 (2000).
Mitsuhashi, "Technical Report: Part 1. Basic Requirements for Designing Optimal Oligonucleotide Probe Sequences", J. Clin. Lab. Analysis, 1996, 10:277-284.
Efron,B., Tibshirani,R.J., 1993, An Introduction to the Bootstrap. Chapman & Hall/CRC, Boca Raton, FL, pp. 45-123.
Owczarzy et al., "Effects of Sodium Ions on DNA Duplex Oligomers" Improved Predictions of Melting Temperatures, Biochemistry 2004, 43:35367-3554.
Plum & Breslauer, "Calorimetry of proteins and nucleic acids", Curr. Opinion Struct. Biol., 1995, 5:682-690.
Cooper, "Thermodynamic analysis of biomolecular interactions", Curr. Opinion Chem. Biol., 1999, 3:557-563.
Fasman ed., "Optical Properties of Nucleic Acids, Absorption, and Circular Dichroism Spectra", Handbook of Biochemistry and Molecular Biology, vol. 1, CRC Press: Cleveland, Ohio, 1975, p. 589.
Warshaw et al., "Optical Properties of Sixteen Dinucleoside Phosphates", J. Mol. Biol. 1966, 20:29-38.
Caruthers et al., "Chemical Synthesis of Deoxyoligonucleotides and Deoxyoligonucleotide Analogs", Methods Enzymol. 1992, 211:3-20.
Tan et al., "Nucleic Acid Helix Stability: Effects of Sale Concentration, Cation Valence and Size, and Chain Length", Biophysical Journal, vol. 90, Feb. 2006, pp. 1175-1190.
Owczarzy et al., "Predicting Sequence-Dependent Melting Stability of Short Duplex DNA Oligomers", Biopolymers 1997, 44:217-239.
Breslauer et al., "Predicting DNA Duplex Stability from the Base Sequence", Proc. Natl. Acad. Sci. U.S.A. 1986, 83:3746-3750.
Sambrook et al., 1989 infra, 11.7-11.8.
Sambrook et al., 1989, infra, 9.50-9.51.
Record, "Effects of Na and Mg Ions on the Helix-Coil Transition of DNA", Biopolymers 1975, 14:2137-2158.
Williams et al., "Laser Temperature-Jump, Spectroscopic, and Thermodynamic Study of Sale Effects on Duplex Formation by dGCATGC", Biochemistry 1989, 28:4283-4291.
SantaLucia, "A unified view of polymer, dumbbell, and oligonucleotide DNA nearest-neighbor thermodynamics", Proc. Natl. Acad. Sci. U.S.A. 1998, 95:1460-1465.
Wetmur, "DNA Probes: Applications of the Principles of Nucleic Acid Hybridization", Critical Review in Biochemistry and Molecular Biology 1991, 26:227-259.
Ivanov & AbouHaidar, "Thermal Stability of Oligodeoxynucleotide Duplexes Bound to Nitrocellulose Filters", Analytical Biochemistry 1995, 232:249-251.
Rychlik et al., "Optimization of the annealing temperature fo DNA amplification in vitro", Nucleic Acids Res. 1990, 18:6409-6412.
Schildkraut et al., "Dependence of the Melting Temperature of DNA on Salt Concentration", Biopolymers 1965, 3:195-208.
SantaLucia et al., "The Thermodynamics of DNA Structural Motifs", Biophys. Biomol. Struct. 2004, 33:415-440.
Lockhart et al., "Expression monitoring by hybridization to high-density oligonucleotide arrays" Nature Biotech. 1996, 14:1675.
Schena et al., "Quantitative Monitoring of Gene Expression Patterns with a Complementary DNA Microarray", Science 1995, 270:467-470.
DeRisi et al., "Exploring the Metabolic and Genetic Control of Gene Expression on a Genomic Scale", Science 1997, 278:680-686.
Meinhoth & Wahl, "Review Hybridization of Nucleic Acids Immobilized on Solid Supports", Anal. Biochem. 1984, 138:267-284.
Denhardt, "A Membrane-Filter Technique for the Detection of Complementary DNA", Biochem. Biophys. Res. Commun. 1966, 23:641-646.

(Continued)

Primary Examiner — Michael Borin
(74) Attorney, Agent, or Firm — McDonnell Boehnen Hulbert & Berghoff LLP

(57) ABSTRACT

The invention relates to methods and systems for predicting or estimating the melting temperature of duplex nucleic acids, in the presence of divalent cations, particularly duplexes of oligonucleotides which may be used as, for example, but not limited to primers or probes in PCR and/or hybridization assays. The methods and algorithms use novel formulas, having terms and coefficients that are functions of the particular nucleotide sequence, to estimate the effect of divalent cation salt conditions on the melting temperature.

27 Claims, 10 Drawing Sheets

OTHER PUBLICATIONS

Southern, "Detection of Specific Sequences Among DNA Fragments Separated by Gel Electrophoresis", *J. Mol. Biol.* 1975, 98:503-517.

Henegariu et al., Multiplex PCR : Critical Parameters and Ste-by-Step Protocol, *Biotechniques* 1997, 23(3):504-11.

Markouatos et al., Multiplex Polymerase Chain Reaction : A Practical Approach, *J. Clin. Lab Anal.* 2002, 16(1):47-51.

Saiki et al., "Enzymatic Amplification of $/beta $-Globin Genomic Sequences and Restriction Site Analysis for Diagnosis of Sickle Cell Amemia", *Science* 1985, 230:1350-1354.

Kleppe et al., "Studies on Polynucleotides XCVI. Repair Replication of Short Synthetic DNA's as catalyzed by DNA Polymerases", *J. Mol. Biol.* 1971, 56:341-361.

Nanko et al. "Nucleic acid duplex stability: influence of base composition on cation effects", Nucleic Acids Research, (1999), vol. 27, No. 14, pp. 2957-2965.

Nakano et al., Nucleic Acid Duplex Stability: Influence of Base Composition on Cation Effects. Nucleic Acids Research, 1999, vol. 27, pp. 2957-2965.

Tan et al., Nucleic Acid Helix Stability: Effects of Salt Concentration, Cation Valence and Size, and Chain Length. Biophysical Journal, Feb. 2006, vol. 90, pp. 1175-1190.

Ahsen et al., Oligonucleotide Melting Temperatures under PCR Conditions: Nearest-Neighbor Corrections for Mg2+, Deoxynucleotide triphosphate, and Dmethyl Sulfoxide Concentrations with Comparison to Alternative Empirical Formulas. Clinical Chemistry, 2001, vol. 47, pp. 1956-1961.

SEQUENCE LISTING

<160> NUMBER OF SEQ ID NOS: 92

<210> SEQ ID NO 1
<211> LENGTH: 15
<212> TYPE: DNA
<213> ORGANISM: Artificial

```
<220> FEATURE:
<223> OTHER INFORMATION: primer

<400> SEQUENCE: 1
tactaacatt aacta                                                15

<210> SEQ ID NO 2
<211> LENGTH: 15
<212> TYPE: DNA
<213> ORGANISM: Artificial
<220> FEATURE:
<223> OTHER INFORMATION: primer

<400> SEQUENCE: 2
atacttactg attag                                                15

<210> SEQ ID NO 3
<211> LENGTH: 15
<212> TYPE: DNA
<213> ORGANISM: Artificial
<220> FEATURE:
<223> OTHER INFORMATION: primer

<400> SEQUENCE: 3
gtacactgtc ttata                                                15

<210> SEQ ID NO 4
<211> LENGTH: 15
<212> TYPE: DNA
<213> ORGANISM: Artificial
<220> FEATURE:
<223> OTHER INFORMATION: primer

<400> SEQUENCE: 4
gtatgagaga cttta                                                15

<210> SEQ ID NO 5
<211> LENGTH: 15
<212> TYPE: DNA
<213> ORGANISM: Artificial
<220> FEATURE:
<223> OTHER INFORMATION: primer

<400> SEQUENCE: 5
ttctacctat gtgat                                                15

<210> SEQ ID NO 6
<211> LENGTH: 15
<212> TYPE: DNA
<213> ORGANISM: Artificial
<220> FEATURE:
<223> OTHER INFORMATION: primer

<400> SEQUENCE: 6
agtagtaatc acacc                                                15

<210> SEQ ID NO 7
<211> LENGTH: 15
<212> TYPE: DNA
<213> ORGANISM: Artificial
<220> FEATURE:
<223> OTHER INFORMATION: primer

<400> SEQUENCE: 7
atcgtctcgg tataa                                                15
```

```
<210> SEQ ID NO 8
<211> LENGTH: 15
<212> TYPE: DNA
<213> ORGANISM: Artificial
<220> FEATURE:
<223> OTHER INFORMATION: primer

<400> SEQUENCE: 8
acgacaggtt tacca                                                      15

<210> SEQ ID NO 9
<211> LENGTH: 15
<212> TYPE: DNA
<213> ORGANISM: Artificial
<220> FEATURE:
<223> OTHER INFORMATION: primer

<400> SEQUENCE: 9
ctttcatgtc cgcat                                                      15

<210> SEQ ID NO 10
<211> LENGTH: 15
<212> TYPE: DNA
<213> ORGANISM: Artificial
<220> FEATURE:
<223> OTHER INFORMATION: primer

<400> SEQUENCE: 10
tggatgtgtg aacac                                                      15

<210> SEQ ID NO 11
<211> LENGTH: 15
<212> TYPE: DNA
<213> ORGANISM: Artificial
<220> FEATURE:
<223> OTHER INFORMATION: primer

<400> SEQUENCE: 11
accccgcaat acatg                                                      15

<210> SEQ ID NO 12
<211> LENGTH: 15
<212> TYPE: DNA
<213> ORGANISM: Artificial
<220> FEATURE:
<223> OTHER INFORMATION: primer

<400> SEQUENCE: 12
gcagtggatg tgaga                                                      15

<210> SEQ ID NO 13
<211> LENGTH: 15
<212> TYPE: DNA
<213> ORGANISM: Artificial
<220> FEATURE:
<223> OTHER INFORMATION: primer

<400> SEQUENCE: 13
ggtccttact tggtg                                                      15

<210> SEQ ID NO 14
<211> LENGTH: 15
<212> TYPE: DNA
<213> ORGANISM: Artificial
<220> FEATURE:
<223> OTHER INFORMATION: primer

<400> SEQUENCE: 14
```
cgcctcatgc tcatc                                                    15

<210> SEQ ID NO 15
<211> LENGTH: 15
<212> TYPE: DNA
<213> ORGANISM: Artificial
<220> FEATURE:
<223> OTHER INFORMATION: primer

<400> SEQUENCE: 15
aaatagccgg gccgc                                                    15

<210> SEQ ID NO 16
<211> LENGTH: 15
<212> TYPE: DNA
<213> ORGANISM: Artificial
<220> FEATURE:
<223> OTHER INFORMATION: primer

<400> SEQUENCE: 16
ccagccagtc tctcc                                                    15

<210> SEQ ID NO 17
<211> LENGTH: 15
<212> TYPE: DNA
<213> ORGANISM: Artificial
<220> FEATURE:
<223> OTHER INFORMATION: primer

<400> SEQUENCE: 17
gacgacaaga ccgcg                                                    15

<210> SEQ ID NO 18
<211> LENGTH: 15
<212> TYPE: DNA
<213> ORGANISM: Artificial
<220> FEATURE:
<223> OTHER INFORMATION: primer

<400> SEQUENCE: 18
cagcctcgtc gcagc                                                    15

<210> SEQ ID NO 19
<211> LENGTH: 15
<212> TYPE: DNA
<213> ORGANISM: Artificial
<220> FEATURE:
<223> OTHER INFORMATION: primer

<400> SEQUENCE: 19
ctcgcggtcg aagcg                                                    15

<210> SEQ ID NO 20
<211> LENGTH: 15
<212> TYPE: DNA
<213> ORGANISM: Artificial
<220> FEATURE:
<223> OTHER INFORMATION: primer

<400> SEQUENCE: 20
gcgtcggtcc gggct                                                    15

<210> SEQ ID NO 21
<211> LENGTH: 20
<212> TYPE: DNA
<213> ORGANISM: Artificial

```
<220> FEATURE:
<223> OTHER INFORMATION: primer

<400> SEQUENCE: 21
tatgtatatt ttgtaatcag                                                    20

<210> SEQ ID NO 22
<211> LENGTH: 20
<212> TYPE: DNA
<213> ORGANISM: Artificial
<220> FEATURE:
<223> OTHER INFORMATION: primer

<400> SEQUENCE: 22
ttcaagttaa acattctatc                                                    20

<210> SEQ ID NO 23
<211> LENGTH: 20
<212> TYPE: DNA
<213> ORGANISM: Artificial
<220> FEATURE:
<223> OTHER INFORMATION: primer

<400> SEQUENCE: 23
tgattctacc tatgtgattt                                                    20

<210> SEQ ID NO 24
<211> LENGTH: 20
<212> TYPE: DNA
<213> ORGANISM: Artificial
<220> FEATURE:
<223> OTHER INFORMATION: primer

<400> SEQUENCE: 24
gagattgttt ccctttcaaa                                                    20

<210> SEQ ID NO 25
<211> LENGTH: 20
<212> TYPE: DNA
<213> ORGANISM: Artificial
<220> FEATURE:
<223> OTHER INFORMATION: primer

<400> SEQUENCE: 25
atgcaatgct acatattcgc                                                    20

<210> SEQ ID NO 26
<211> LENGTH: 20
<212> TYPE: DNA
<213> ORGANISM: Artificial
<220> FEATURE:
<223> OTHER INFORMATION: primer

<400> SEQUENCE: 26
ccactatacc atctatgtac                                                    20

<210> SEQ ID NO 27
<211> LENGTH: 20
<212> TYPE: DNA
<213> ORGANISM: Artificial
<220> FEATURE:
<223> OTHER INFORMATION: primer

<400> SEQUENCE: 27
ccatcattgt gtctacctca                                                    20
```

-continued

```
<210> SEQ ID NO 28
<211> LENGTH: 20
<212> TYPE: DNA
<213> ORGANISM: Artificial
<220> FEATURE:
<223> OTHER INFORMATION: primer

<400> SEQUENCE: 28
cgggaccaac taaaggaaat                                              20

<210> SEQ ID NO 29
<211> LENGTH: 20
<212> TYPE: DNA
<213> ORGANISM: Artificial
<220> FEATURE:
<223> OTHER INFORMATION: primer

<400> SEQUENCE: 29
tagtggcgat tagattctgc                                              20

<210> SEQ ID NO 30
<211> LENGTH: 20
<212> TYPE: DNA
<213> ORGANISM: Artificial
<220> FEATURE:
<223> OTHER INFORMATION: primer

<400> SEQUENCE: 30
agctgcagtg gatgtgagaa                                              20

<210> SEQ ID NO 31
<211> LENGTH: 20
<212> TYPE: DNA
<213> ORGANISM: Artificial
<220> FEATURE:
<223> OTHER INFORMATION: primer

<400> SEQUENCE: 31
tacttccagt gctcagcgta                                              20

<210> SEQ ID NO 32
<211> LENGTH: 20
<212> TYPE: DNA
<213> ORGANISM: Artificial
<220> FEATURE:
<223> OTHER INFORMATION: primer

<400> SEQUENCE: 32
cagtgagaca gcaatggtcg                                              20

<210> SEQ ID NO 33
<211> LENGTH: 20
<212> TYPE: DNA
<213> ORGANISM: Artificial
<220> FEATURE:
<223> OTHER INFORMATION: primer

<400> SEQUENCE: 33
cgagcttatc cctatccctc                                              20

<210> SEQ ID NO 34
<211> LENGTH: 20
<212> TYPE: DNA
<213> ORGANISM: Artificial
<220> FEATURE:
<223> OTHER INFORMATION: primer

<400> SEQUENCE: 34
```
cgtactagcg ttggtcatgg                                               20

<210> SEQ ID NO 35
<211> LENGTH: 20
<212> TYPE: DNA
<213> ORGANISM: Artificial
<220> FEATURE:
<223> OTHER INFORMATION: primer

<400> SEQUENCE: 35
aaggcgagtc aggctcagtg                                               20

<210> SEQ ID NO 36
<211> LENGTH: 20
<212> TYPE: DNA
<213> ORGANISM: Artificial
<220> FEATURE:
<223> OTHER INFORMATION: primer

<400> SEQUENCE: 36
accgacgacg ctgatccgat                                               20

<210> SEQ ID NO 37
<211> LENGTH: 20
<212> TYPE: DNA
<213> ORGANISM: Artificial
<220> FEATURE:
<223> OTHER INFORMATION: primer

<400> SEQUENCE: 37
agcagtccgc cacaccctga                                               20

<210> SEQ ID NO 38
<211> LENGTH: 20
<212> TYPE: DNA
<213> ORGANISM: Artificial
<220> FEATURE:
<223> OTHER INFORMATION: primer

<400> SEQUENCE: 38
cagcctcgtt cgcacagccc                                               20

<210> SEQ ID NO 39
<211> LENGTH: 20
<212> TYPE: DNA
<213> ORGANISM: Artificial
<220> FEATURE:
<223> OTHER INFORMATION: primer

<400> SEQUENCE: 39
gtggtgggcc gtgcgctctg                                               20

<210> SEQ ID NO 40
<211> LENGTH: 20
<212> TYPE: DNA
<213> ORGANISM: Artificial
<220> FEATURE:
<223> OTHER INFORMATION: primer

<400> SEQUENCE: 40
gtccacgccc ggtgcgacgg                                               20

<210> SEQ ID NO 41
<211> LENGTH: 25
<212> TYPE: DNA
<213> ORGANISM: Artificial

```
<220> FEATURE:
<223> OTHER INFORMATION: primer

<400> SEQUENCE: 41
gatatagcaa aattctaagt taata                                           25

<210> SEQ ID NO 42
<211> LENGTH: 25
<212> TYPE: DNA
<213> ORGANISM: Artificial
<220> FEATURE:
<223> OTHER INFORMATION: primer

<400> SEQUENCE: 42
ataactttac gtgtgtgacc tatta                                           25

<210> SEQ ID NO 43
<211> LENGTH: 25
<212> TYPE: DNA
<213> ORGANISM: Artificial
<220> FEATURE:
<223> OTHER INFORMATION: primer

<400> SEQUENCE: 43
gttctatact cttgaagttg attac                                           25

<210> SEQ ID NO 44
<211> LENGTH: 25
<212> TYPE: DNA
<213> ORGANISM: Artificial
<220> FEATURE:
<223> OTHER INFORMATION: primer

<400> SEQUENCE: 44
ccctgcactt taactgaatt gttta                                           25

<210> SEQ ID NO 45
<211> LENGTH: 25
<212> TYPE: DNA
<213> ORGANISM: Artificial
<220> FEATURE:
<223> OTHER INFORMATION: primer

<400> SEQUENCE: 45
taaccatact gaataccttt tgacg                                           25

<210> SEQ ID NO 46
<211> LENGTH: 25
<212> TYPE: DNA
<213> ORGANISM: Artificial
<220> FEATURE:
<223> OTHER INFORMATION: primer

<400> SEQUENCE: 46
tccacacggt agtaaaatta ggctt                                           25

<210> SEQ ID NO 47
<211> LENGTH: 25
<212> TYPE: DNA
<213> ORGANISM: Artificial
<220> FEATURE:
<223> OTHER INFORMATION: primer

<400> SEQUENCE: 47
ttccaaaagg agttatgagt tgcga                                           25
```

```
<210> SEQ ID NO 48
<211> LENGTH: 25
<212> TYPE: DNA
<213> ORGANISM: Artificial
<220> FEATURE:
<223> OTHER INFORMATION: primer

<400> SEQUENCE: 48
aatatctctc atgcgccaag ctaca                                          25

<210> SEQ ID NO 49
<211> LENGTH: 25
<212> TYPE: DNA
<213> ORGANISM: Artificial
<220> FEATURE:
<223> OTHER INFORMATION: primer

<400> SEQUENCE: 49
tagtatatcg cagcatcata caggc                                          25

<210> SEQ ID NO 50
<211> LENGTH: 25
<212> TYPE: DNA
<213> ORGANISM: Artificial
<220> FEATURE:
<223> OTHER INFORMATION: primer

<400> SEQUENCE: 50
tggattctac tcaaccttag tctgg                                          25

<210> SEQ ID NO 51
<211> LENGTH: 25
<212> TYPE: DNA
<213> ORGANISM: Artificial
<220> FEATURE:
<223> OTHER INFORMATION: primer

<400> SEQUENCE: 51
cggaatccat gttacttcgg ctatc                                          25

<210> SEQ ID NO 52
<211> LENGTH: 25
<212> TYPE: DNA
<213> ORGANISM: Artificial
<220> FEATURE:
<223> OTHER INFORMATION: primer

<400> SEQUENCE: 52
ctggtctgga tctgagaact tcagg                                          25

<210> SEQ ID NO 53
<211> LENGTH: 25
<212> TYPE: DNA
<213> ORGANISM: Artificial
<220> FEATURE:
<223> OTHER INFORMATION: primer

<400> SEQUENCE: 53
acagcgaatg gacctacgtg gcctt                                          25

<210> SEQ ID NO 54
<211> LENGTH: 25
<212> TYPE: DNA
<213> ORGANISM: Artificial
<220> FEATURE:
<223> OTHER INFORMATION: primer

<400> SEQUENCE: 54
```
agcaagtcga gcagggccta cgttt                                              25

<210> SEQ ID NO 55
<211> LENGTH: 25
<212> TYPE: DNA
<213> ORGANISM: Artificial
<220> FEATURE:
<223> OTHER INFORMATION: primer

<400> SEQUENCE: 55
gcgagcgaca ggttacttgg ctgat                                              25

<210> SEQ ID NO 56
<211> LENGTH: 25
<212> TYPE: DNA
<213> ORGANISM: Artificial
<220> FEATURE:
<223> OTHER INFORMATION: primer

<400> SEQUENCE: 56
aaaggtgtcg cggagagtcg tgctg                                              25

<210> SEQ ID NO 57
<211> LENGTH: 25
<212> TYPE: DNA
<213> ORGANISM: Artificial
<220> FEATURE:
<223> OTHER INFORMATION: primer

<400> SEQUENCE: 57
atgggtggga gcctcggtag cagcc                                              25

<210> SEQ ID NO 58
<211> LENGTH: 25
<212> TYPE: DNA
<213> ORGANISM: Artificial
<220> FEATURE:
<223> OTHER INFORMATION: primer

<400> SEQUENCE: 58
cagtgggctc ctgggcgtgc tggtc                                              25

<210> SEQ ID NO 59
<211> LENGTH: 25
<212> TYPE: DNA
<213> ORGANISM: Artificial
<220> FEATURE:
<223> OTHER INFORMATION: primer

<400> SEQUENCE: 59
gccaactccg tcgccgttcg tgcgc                                              25

<210> SEQ ID NO 60
<211> LENGTH: 25
<212> TYPE: DNA
<213> ORGANISM: Artificial
<220> FEATURE:
<223> OTHER INFORMATION: primer

<400> SEQUENCE: 60
acgggtcccc gcaccgcacc gccag                                              25

<210> SEQ ID NO 61
<211> LENGTH: 30
<212> TYPE: DNA
<213> ORGANISM: Artificial

```
<220> FEATURE:
<223> OTHER INFORMATION: primer

<400> SEQUENCE: 61
ttatgtatta agttatatag tagtagtagt                              30

<210> SEQ ID NO 62
<211> LENGTH: 30
<212> TYPE: DNA
<213> ORGANISM: Artificial
<220> FEATURE:
<223> OTHER INFORMATION: primer

<400> SEQUENCE: 62
attgatatcc ttttctattc atctttcatt                              30

<210> SEQ ID NO 63
<211> LENGTH: 30
<212> TYPE: DNA
<213> ORGANISM: Artificial
<220> FEATURE:
<223> OTHER INFORMATION: primer

<400> SEQUENCE: 63
aaagtacatc aacatagaga attgcatttc                              30

<210> SEQ ID NO 64
<211> LENGTH: 30
<212> TYPE: DNA
<213> ORGANISM: Artificial
<220> FEATURE:
<223> OTHER INFORMATION: primer

<400> SEQUENCE: 64
cttaagatat gagaacttca actaatgtgt                              30

<210> SEQ ID NO 65
<211> LENGTH: 30
<212> TYPE: DNA
<213> ORGANISM: Artificial
<220> FEATURE:
<223> OTHER INFORMATION: primer

<400> SEQUENCE: 65
ctcaacttgc ggtaaataaa tcgcttaatc                              30

<210> SEQ ID NO 66
<211> LENGTH: 30
<212> TYPE: DNA
<213> ORGANISM: Artificial
<220> FEATURE:
<223> OTHER INFORMATION: primer

<400> SEQUENCE: 66
tattgagaac aagtgtccga ttagcagaaa                              30

<210> SEQ ID NO 67
<211> LENGTH: 30
<212> TYPE: DNA
<213> ORGANISM: Artificial
<220> FEATURE:
<223> OTHER INFORMATION: primer

<400> SEQUENCE: 67
gtcatacgac tgagtgcaac attgttcaaa                              30
```

```
<210> SEQ ID NO 68
<211> LENGTH: 30
<212> TYPE: DNA
<213> ORGANISM: Artificial
<220> FEATURE:
<223> OTHER INFORMATION: primer

<400> SEQUENCE: 68
aacctgcaac atggagtttt tgtctcatgc                                30

<210> SEQ ID NO 69
<211> LENGTH: 30
<212> TYPE: DNA
<213> ORGANISM: Artificial
<220> FEATURE:
<223> OTHER INFORMATION: primer

<400> SEQUENCE: 69
ccgtgcggtg tgtacgtttt attcatcata                                30

<210> SEQ ID NO 70
<211> LENGTH: 30
<212> TYPE: DNA
<213> ORGANISM: Artificial
<220> FEATURE:
<223> OTHER INFORMATION: primer

<400> SEQUENCE: 70
gttcacgtcc gaaagctcga aaaggatac                                 30

<210> SEQ ID NO 71
<211> LENGTH: 30
<212> TYPE: DNA
<213> ORGANISM: Artificial
<220> FEATURE:
<223> OTHER INFORMATION: primer

<400> SEQUENCE: 71
agtctggtct ggatctgaga acttcaggct                                30

<210> SEQ ID NO 72
<211> LENGTH: 30
<212> TYPE: DNA
<213> ORGANISM: Artificial
<220> FEATURE:
<223> OTHER INFORMATION: primer

<400> SEQUENCE: 72
tcggagaaat cactgagctg cctgagaaga                                30

<210> SEQ ID NO 73
<211> LENGTH: 30
<212> TYPE: DNA
<213> ORGANISM: Artificial
<220> FEATURE:
<223> OTHER INFORMATION: primer

<400> SEQUENCE: 73
cttcaacgga tcaggtagga ctgtggtggg                                30

<210> SEQ ID NO 74
<211> LENGTH: 30
<212> TYPE: DNA
<213> ORGANISM: Artificial
<220> FEATURE:
<223> OTHER INFORMATION: primer

<400> SEQUENCE: 74
```
acgcccacag gattaggctg gcccacattg                                    30

<210> SEQ ID NO 75
<211> LENGTH: 30
<212> TYPE: DNA
<213> ORGANISM: Artificial
<220> FEATURE:
<223> OTHER INFORMATION: primer

<400> SEQUENCE: 75
gttattccgc agtccgatgg cagcaggctc                                    30

<210> SEQ ID NO 76
<211> LENGTH: 30
<212> TYPE: DNA
<213> ORGANISM: Artificial
<220> FEATURE:
<223> OTHER INFORMATION: primer

<400> SEQUENCE: 76
tcagtaggcg tgacgcagag ctggcgatgg                                    30

<210> SEQ ID NO 77
<211> LENGTH: 30
<212> TYPE: DNA
<213> ORGANISM: Artificial
<220> FEATURE:
<223> OTHER INFORMATION: primer

<400> SEQUENCE: 77
cgcgccacgt gtgatctaca gccgttcggc                                    30

<210> SEQ ID NO 78
<211> LENGTH: 30
<212> TYPE: DNA
<213> ORGANISM: Artificial
<220> FEATURE:
<223> OTHER INFORMATION: primer

<400> SEQUENCE: 78
gacctgacgt ggaccgctcc tgggcgtggt                                    30

<210> SEQ ID NO 79
<211> LENGTH: 30
<212> TYPE: DNA
<213> ORGANISM: Artificial
<220> FEATURE:
<223> OTHER INFORMATION: primer

<400> SEQUENCE: 79
gcccctccac tggccgacgg cagcaggctc                                    30

<210> SEQ ID NO 80
<211> LENGTH: 30
<212> TYPE: DNA
<213> ORGANISM: Artificial
<220> FEATURE:
<223> OTHER INFORMATION: primer

<400> SEQUENCE: 80
cgccgctgcc gactggagga gcgcgggacg                                    30

<210> SEQ ID NO 81
<211> LENGTH: 10
<212> TYPE: DNA
<213> ORGANISM: Artificial

```
<220> FEATURE:
<223> OTHER INFORMATION: primer

<400> SEQUENCE: 81
atcaatcata                                                            10

<210> SEQ ID NO 82
<211> LENGTH: 10
<212> TYPE: DNA
<213> ORGANISM: Artificial
<220> FEATURE:
<223> OTHER INFORMATION: primer

<400> SEQUENCE: 82
ttgtagtcat                                                            10

<210> SEQ ID NO 83
<211> LENGTH: 10
<212> TYPE: DNA
<213> ORGANISM: Artificial
<220> FEATURE:
<223> OTHER INFORMATION: primer

<400> SEQUENCE: 83
gaaatgaaag                                                            10

<210> SEQ ID NO 84
<211> LENGTH: 10
<212> TYPE: DNA
<213> ORGANISM: Artificial
<220> FEATURE:
<223> OTHER INFORMATION: primer

<400> SEQUENCE: 84
ccaacttctt                                                            10

<210> SEQ ID NO 85
<211> LENGTH: 10
<212> TYPE: DNA
<213> ORGANISM: Artificial
<220> FEATURE:
<223> OTHER INFORMATION: primer

<400> SEQUENCE: 85
atcgtctgga                                                            10

<210> SEQ ID NO 86
<211> LENGTH: 10
<212> TYPE: DNA
<213> ORGANISM: Artificial
<220> FEATURE:
<223> OTHER INFORMATION: primer

<400> SEQUENCE: 86
agcgtaagtc                                                            10

<210> SEQ ID NO 87
<211> LENGTH: 10
<212> TYPE: DNA
<213> ORGANISM: Artificial
<220> FEATURE:
<223> OTHER INFORMATION: primer

<400> SEQUENCE: 87
cgatctgcga                                                            10
```

```
<210> SEQ ID NO 88
<211> LENGTH: 10
<212> TYPE: DNA
<213> ORGANISM: Artificial
<220> FEATURE:
<223> OTHER INFORMATION: primer

<400> SEQUENCE: 88
tggcgagcac                                                              10

<210> SEQ ID NO 89
<211> LENGTH: 10
<212> TYPE: DNA
<213> ORGANISM: Artificial
<220> FEATURE:
<223> OTHER INFORMATION: primer

<400> SEQUENCE: 89
gatgcgctcg                                                              10

<210> SEQ ID NO 90
<211> LENGTH: 10
<212> TYPE: DNA
<213> ORGANISM: Artificial
<220> FEATURE:
<223> OTHER INFORMATION: primer

<400> SEQUENCE: 90
gggaccgcct                                                              10

<210> SEQ ID NO 91
<211> LENGTH: 11
<212> TYPE: DNA
<213> ORGANISM: Artificial
<220> FEATURE:
<223> OTHER INFORMATION: primer

<400> SEQUENCE: 91
cgtacacatg c                                                            11

<210> SEQ ID NO 92
<211> LENGTH: 11
<212> TYPE: DNA
<213> ORGANISM: Artificial
<220> FEATURE:
<223> OTHER INFORMATION: primer

<400> SEQUENCE: 92
ccattgctac c                                                            11
```

METHOD FOR ESTIMATING A MELTING TEMPERATURE OF A NUCLEIC ACID IN BUFFERS CONTAINING MAGNESIUM IONS

FIELD OF THE INVENTION

The invention relates to methods and systems for predicting or estimating the melting temperature of duplex nucleic acids, in the presence of divalent cations, particularly duplexes of oligonucleotides which may be used as, for example, but not limited to, primers or probes in PCR and/or hybridization assays. The invention also relates to methods and systems for designing and selecting oligonucleotide probes and primers having a predicted melting temperature which is optimized for such assays. The methods and algorithms use novel formulas, having terms and coefficients that are functions of the particular nucleotide sequence, to estimate the effect of divalent cation salt conditions on the melting temperature.

FIELD OF THE INVENTION

The invention relates to methods and systems for predicting or estimating the melting temperature of duplex nucleic acids, in the presence of divalent cations, particularly duplexes of oligonucleotides which may be used as, for example, but not limited to, primers or probes in PCR and/or hybridization assays. The invention also relates to methods and systems for designing and selecting oligonucleotide probes and primers having a predicted melting temperature which is optimized for such assays. The methods and algorithms use novel formulas, having terms and coefficients that are functions of the particular nucleotide sequence, to estimate the effect of divalent cation salt conditions on the melting temperature.

BACKGROUND OF THE INVENTION

Hybridization between complementary nucleic acids is an implicit feature in the Watson-Crick model for DNA structure that is exploited for many applications of the biological and biomedical arts. For example, virtually all methods for replicating and/or amplifying nucleic acid molecules are initiated by a step in which a complementary oligonucleotide (typically referred to as a "primer") hybridizes to some portion of a "target" nucleic acid molecule. A polymerase then synthesizes a complementary nucleic acid from the primer, using the target nucleic acid as a "template." See, Kleppe et al., *J. Mol. Biol.* 1971, 56:341-361.

One particular application, known as the polymerase chain reaction, PCR, is widely used in a variety of biological and medical arts. For a description, see Saiki et al., *Science* 1985, 230:1350-1354. In PCR, two or more primers are used that hybridize to separate regions of a target nucleic acid and its complementary sequence. The sample is then subjected to multiple cycles of heating and cooling, repeatedly hybridizing and dissociating the complementary strands so that multiple replications of the target nucleic acid and its complement are performed. As a result, even very small initial quantities of a target nucleic acid may be enormously increased, or "amplified," for subsequent uses (e.g., for detection, sequencing, etc.).

Multiplex PCR is a particular version of PCR in which several different primers are used to amplify and detect a plurality of different nucleic acids in a sample—usually ten to a hundred different target nucleic acids. Thus, the technique allows a user to amplify and evaluate large numbers of different nucleic acids simultaneously in a single sample. The enormous benefits of high throughput, speed and efficiency offered by this technique has made multiplex PCR increasingly popular. However, achievement of successful multiplex PCR usually involves empirical testing as existing computer programs that pick and/or design PCR primers have errors. In multiplex PCR, the errors become additive and therefore good results are seldom achieved without a substantialsome amount of trial and error. See, Markouatos et al., *J. Clin. Lab Anal.* 2002, 16(1):47-51; Henegarin et al., *Biotechniques* 1997, 23(3):504-11.

Other techniques that are widely used in the biological and medical arts exploit nucleic acid hybridization to detect target nucleic acid sequences in a sample. See, for example, Southern, *J. Mol. Biol.* 1975, 98:503-517; Denhardt, *Biochem. Biophys. Res. Commun.* 1966, 23:641-646; Meinhoth & Wahl, *Anal. Biochem.* 1984, 138:267-284. For instance, Southern blotting and similar techniques have long been used in which nucleic acid molecules from a sample are immobilized onto a solid surface or support (e.g., a membrane support). A target nucleic acid molecule of interest may then be detected by contacting one or more complementary nucleic acids (often referred to as nucleic acid "probes") and detecting their hybridization to nucleic acid molecules on the surface or support. A signal generated by some detectable label on the probes is proportional to the amount of hybridization to the target.

Similar techniques are also known in which one or more nucleic acid probes are immobilized onto a solid surface or support, and a sample of nucleic acid molecules is hybridized thereto. Nucleic acid arrays, for example, are known and have become increasingly popular in the art. See, e.g., DeRisi et al., *Science* 1997, 278:680-686; Schena et al., *Science* 1995, 270:467-470; and Lockhart et al., *Nature Biotech.* 1996, 14:1675. See also, U.S. Pat. No. 5,510,270 issued Apr. 23, 1996 to Fodor et al. Nucleic acid arrays typically comprise a plurality (often many hundreds or even thousands) of different probes, each immobilized at a defined location on the surface or support. A sample of nucleic acids (for example, an mRNA sample, or a sample of cDNA or cRNA derived therefrom), that may be detectably labeled, may then be hybridized to the array. Hybridization of those nucleic acids to the different probes may be assessed, e.g., by detecting labeled nucleic acids at each probe's location on the array. Thus, hybridization techniques using nucleic acid arrays have the potential for simultaneously detecting a large number of different nucleic acid molecules in a sample, by simultaneously detecting their hybridization to the different probes of the array.

The successful implementation of all techniques involving nucleic acid hybridization (including the exemplary techniques described, supra) is dependent upon the use of nucleic acid probes and primers that specifically hybridize with complementary nucleic acids of interest while, at the same time, avoiding non-specific hybridization with other nucleic acid molecules that may be present. For a review, see Wetmur, *Critical Reviews in Biochemistry and Molecular Biology* 1991, 26:227-259. These properties are even more critical in techniques, such as multiplex PCR and microarray hybridization, where a plurality of different probes or primers is used, each of which may be specific for a different target nucleic acid.

Duplex stability between complementary nucleic acid molecules is frequently expressed by the duplex's "melting temperature", $T_m$. Roughly speaking, the $T_m$ indicates the temperature at which a duplex nucleic acid dissociates into single-stranded nucleic acids. Nucleic acid hybridization may be performed at a temperature just slightly below the $T_m$, so that hybridization between a probe or primer and its target nucleic acid is optimized, while minimizing non-specific hybridization of the probe or primer to other, non-target nucleic acids. Duplex stability and $T_m$ are also important in applications, such as PCR, where thermocycling may be involved. During such thermocycling melting steps, it is important that the sample temperature be raised sufficiently above the $T_m$ so that duplexes of the target nucleic acid and its complement are dissociated. In subsequent steps of reannealing, however, the temperature must be brought sufficiently below the $T_m$ that duplexes of the target nucleic acid and primer are able to form, while still remaining high enough to avoid non-specific hybridization events. For a general discussion, see Rychlik et al., Nucleic Acids Research 1990, 18:6409-6412.

Traditionally, theoretical or empirical models that relate duplex stability to nucleotide sequence have been used to predict or estimate melting temperatures for particular nucleic acids. For example, Breslauer et al. (*Proc. Natl. Acad. Sci. U.S.A.* 1986, 83:3746-3750) describe a model for predicting melting temperatures that is widely used in the art, known as the "nearest neighbor model." See also, SantaLucia et al., *Biophys. Biomol. Struct.* 2004, 33:415-440; Owczarzy et al., *Biopolymers* 1997, 44:217-239; and SantaLucia, *Proc. Natl. Acad. Sci. USA.* 1998, 95:1460-1465. Such models are usually calibrated or optimized for particular salt conditions, typically 1 M Na$^+$. However, applications that exploit nucleic acid hybridization may be implemented in a variety of different salt conditions, including, for example, magnesium and potassium, with cation concentrations typically being on the order of magnitude of 0.001-1 M. Thus, melting temperatures for particular probes or primers in an assay are typically predicted by predicting a melting temperature at a first salt concentration using the nearest neighbor or other models, and then using another theoretical or empirical model to predict what effect(s) the salt conditions of the particular assay will have on that melting temperature.

Most existing models used to estimate $T_m$ do so in solutions of some specific cation concentrations and then correct for presence and concentrations of all cations. Schildkraut et al. (*Biopolymers* 1965, 3:195-208) proposed the following formula to estimate nucleic acid melting temperatures at different sodium ion concentrations, [Na$^+$]:

$$T_m([\text{Na}^+]) = T_m(1M\ \text{Na}^+) + 16.6 \times \log [\text{Na}^+] \quad \text{(Equation 1)}$$

where $T_m$(1M Na$^+$) is the melting temperature of the DNA duplex in solution of 1 M sodium ions. Equation 1, above, is based on empirical data from the specific study of *Escherichia coli* genomic DNA in buffer of between 0.01-0.2 M [Na$^+$]. Nevertheless, the use of this equation has been routinely generalized to model any DNA duplex oligomer pair. See, for example, Rychlik et al., *Nucleic Acids Res.* 1990, 18:6409-6412, Ivanov & AbouHaidar, *Analytical Biochemistry* 1995, 232:249-251; Wetmur, *Critical Review in Biochemistry and Molecular Biology* 1991, 26:227-259.

SantaLucia and Peyret analyzed data of 26 oligonucleotide duplexes and published correction equations for effects of sodium ions. They assumed that sodium ions change the transition entropy of duplex melting, but do not effect a value of $\Delta H^0$ (see SantaLucia, *Proc. Natl. Acad. Sci. USA.* 1998, 95:1460-1465 and Peyret, Ph.D. Thesis, Wayne State University, Detroit, Mich., pp. 128, section 5.4.2 (2000)), and derived the following equation, $$\frac{1}{T_m(\text{Na}^+)} = \frac{1}{T_m(1M\ \text{Na}^+)} + \frac{0.368N}{\Delta H^0} \times \ln[\text{Na}^+] \quad \text{(Equation 2)}$$

$\Delta H^0$ is the standard transition enthalpy predicted from a nearest-neighbor model and N is the number of phosphate groups in the duplex divided by 2. That is, N is typically for synthetic oligomers equal to number of base pairs decreased by one.

Also, U.S. Pat. No. 6,889,143 (incorporated herein by reference in its entirety) describes equations developed for varying sodium cation concentrations, taking into account the G-C content of the oligonucleotides, $$\frac{1}{T_m(\text{Na}^+)} = \frac{1}{T_m(1M\ \text{Na}^+)} + (4.29 \cdot f_{GC} - 3.95) \cdot 10^{-5} \cdot \ln[Mon^+] + 9.40 \cdot 10^{-6} \cdot (\ln[Mon^+])^2 \quad \text{(Equation 3)}$$

While several equations were published to model relationships between monovalent cations (e.g., sodium) and DNA melting temperature (see, e.g., Owczarzy et al., *Biochemistry* 2004, 43:3537-3554), little is known about the effect of divalent cations. Corrections were previously suggested to explain effects of magnesium ions on DNA melting temperatures that are based on the assumption that stabilizing effects of magnesium ions are very similar to stabilizing effects of sodium ions and therefore $T_m$ salt correction for sodium ions can be applied to solutions of magnesium ions using a simple adjustment. These corrections (Equations 6, 7, and 8, below) use Equation 4 where the square root of Mg$^{2+}$ concentration is added to monovalent cation concentrations [Mon$^+$] (e.g., Na$^+$, Tris$^+$, or K$^+$) and the "equivalent effect" sodium concentration, [Na$^+$]$_{eq}$, is calculated, $$[\text{Na}^+]_{eq} = \beta \times \sqrt{[\text{Mg}^{2+}]} + [Mon^+] \quad \text{(Equation 4)}$$

The monovalent cation concentration, [Mon$^+$], is a sum of the concentrations of all monovalent cations in solution. In the pH range typically employed the H$^+$ concentration is less than $10^{-5}$ M and need not be considered; however, H$^+$ ions are not considered. For a typical PCR buffer, concentrations of K$^+$ and Tris$^+$ ions are summed, $$[Mon^+] = [\text{K}^+] + [\text{Tris}^+] \quad \text{(Equation 5)}$$

Values of the conversion factor $\beta$ from 3.3 to 4 were suggested in published literature. The equivalent sodium concentration from Equation 4, [Na$^+$]$_{eq}$, may be combined with the $T_m$ sodium correction equations 1 and 2. Three such correction equations were reported in the published literature, $$T_m(\text{Mg}^{2+}) = T_m(1M\ \text{Na}^+) + 16.6 \times \log\left(\frac{4 \cdot \sqrt{[\text{Mg}^{2+}]} + }{[Mon^+]}\right) \quad \text{(Equation 6)}$$

(Mitsuhashi, *J. Clin. Lab. Analysis,* 1996, 10:277-284)

$$\frac{1}{T_m(Mg^{2+})} = \frac{1}{T_m(1 M NA^+)} + \frac{0.368\, N}{\Delta H^0} \times \ln\left(3.79 \cdot \sqrt{[Mg^{2+}] + [Mon^+]}\right)$$

(Equation 7)

(von Ahsen et al., *Clin. Chem.* 2001, 47:1956-1961)

$$\frac{1}{T_m(Mg^{2+})} = \frac{1}{T_m(1\ M\ Na^+)} + \frac{0.368\, N}{\Delta H^0} \times \ln\left(3.3 \cdot \sqrt{[Mg^{2+}]} + [Mon^+]\right)$$

(Equation 8)

(Peyret, Ph.D. Thesis, Wayne State University, Detroit, Mich., pp. 128, section 5.4.2 (2000)). In some of the above cases, the $T_m$ correction function is expressed directly in terms of Tm (Equation 6), and in Equation 7 and 8 the $T_m$ correction function is related to the reciprocal of $T_m$ (1/Tm).

These equations were used to determine the $T_m$ salt correction for a solution containing magnesium ions in the absence or presence of other monovalent ions.

Recently, Tan and Chen (*Biophys. J* 2006, 90:1175-1190) developed the "Tightly Bound Ion model" and proposed a new formula for dependence of melting temperatures on magnesium concentrations, $$\frac{1}{T_m(Mg^{2+})} = \frac{1}{T_m(1M\ Na^+)} - \frac{0.00322 \times \Delta g_{el} \times (N_{bp} - 1)}{\Delta H^0}$$

(Equation 9)

where $\Delta g_{el}$ is the electrostatic free energy per base stack (kcal/mol), $$\Delta g_{el} = \left(0.02 + \frac{1.18}{N_{bp}^2}\right) \ln[Mg^{2+}] + \left(0.0068 + \frac{0.344}{N_{bp}^2}\right)(\ln[Mg^{2+}])^2$$

(Equation 10)

The Equations 9 and 10 were proposed to be appropriate for duplexes with six or more base pairs in solutions where magnesium ions have dominant effects. These magnesium correction equations do not apply to mixed buffers where monovalent ions compete with magnesium ions.

Further studies on the correction of melting temperature include Nakano et al., *Nucleic Acids Research* 1999, 27:2957-2965; Williams et al., *Biochemistry* 1989, 28:4283-4291; Record, *Biopolymers* 1975, 14:2137-2158.

Notably, none of the $T_m$ correction equations in the prior art consider the sequence of the polynucleotide or its G/C content value, fGC.

As will be demonstrated below, the above equations do not adequately predict melting temperatures in the presence of divalent cations. The errors are significant, in some cases as large as 15 C, and can adversely affect the performance of probes and primers in experiments and assays. The effects on melting temperature due to divalent cations, in the presence and/or absence of monovalent ions, differ significantly from the effects of sodium ions and are not adequately described in the equations above. Therefore, there is a significant need for methods of estimating and predicting melting temperatures with improved accuracy, especially for oligonucleotides in the presence of divalent cations. There further exists a need for methods of designing experiments in which the melting temperature of each oligonucleotide in the presence of divalent cations is optimized for the particular method or assay, such as PCR or other assay that involves nucleic acid hybridization. The present invention meets these needs by providing methods to more accurately predict the melting temperature of nucleic acids in buffers with divalent cations.

The citation or discussion of any reference in this section or elsewhere in the specification is made only to clarify the description of the present invention and is not an admission that any such reference is "prior art" against any invention described herein.

SUMMARY OF THE INVENTION

The present invention provides a method for predicting melting temperatures, $T_m$, for nucleic acid duplex oligomers. The method applies to nucleic acid duplexes in solutions containing divalent cations $[X^{2+}]$, wherein the divalent cation concentration preferably ranges from 0.1 mM to about 1 M concentration. Specifically, the method allows for an accurate prediction of the melting temperatures, $T_m$, for nucleic acid duplex oligomers as divalent and, optionally, monovalent, $[Mon^+]$, cation concentration varies, wherein:

(a) a reference melting temperature, $Tm^\circ$, for the polynucleotide is obtained or provided at a reference monovalent ion concentration $[Mon+]^\circ$, and (b) modifying said reference melting temperature, or reciprocal of said melting temperature, by one or more terms which are a function of $f_{GC}$ to determine the melting temperature of the polynucleotide at the desired monovalent and divalent cation concentrations.

In some certain embodiments, the present invention provides a novel method for estimating a melting temperature, $T_m(X^{2+})$, for a polynucleotide at a desired divalent ion concentration, $[X^{2+}]$, and an optionally present monovalent ion concentration $[Mon^+]$, said polynucleotide having a known G-C content value, $f_{GC}$, the method comprising:

(a) obtaining a reference melting temperature, $T_m^{\ 0}$, for the polynucleotide, said reference melting temperature being a melting temperature obtained or provided for the polynucleotide at a reference monovalent ion concentration, $[Mon^{+0}]$;

(b) modifying said reference melting temperature, or the reciprocal of said reference melting temperature, by adding (i) a term comprising a logarithm of the divalent ion concentration, and (ii) a term comprising $f_{GC}$ multiplied by a term comprising a logarithm of the divalent ion concentration, and optionally adding a further term comprising a logarithm of the divalent ion concentration, to determine the melting temperature of the oligonucleotide at the desired monovalent and divalent cation concentrations; and When the reciprocal of the reference melting temperature is used, the method further comprises (c) taking the reciprocal of the modified reciprocal; wherein the estimated melting temperature is calculated using the reference melting temperature.

In a further embodiment, the present invention provides a novel method for estimating a melting temperature, $T_m(X^{2+})$, for a polynucleotide at a desired divalent ion concentration, $[X^{2+}]$, and an optionally present monovalent ion concentration $[Mon^+]$, said polynucleotide having a known G-C content value, $f_{GC}$, wherein the reciprocal of a reference melting temperature, $T_m^{\ 0}$, is modified by adding a term comprising $a+b\ \ln\ [X^{2+}]+f_{GC} \cdot (c+d\ \ln\ [X^{2+}])$, wherein the reference melting temperature is a melting temperature obtained or provided for the polynucleotide at a reference monovalent ion concentration, $[Mon^+]^0$, and wherein each of the coefficients a, b, c, and d is optimized for predicting polynucleotide melting temperatures based on, for example, experimental data.

In another embodiment, the present invention provides a novel method for estimating a melting temperature, $T_m(X^{2+})$, for a polynucleotide at a desired divalent ion concentration, $[X^{2+}]$, and an optionally present monovalent ion concentration $[Mon^+]$, said polynucleotide having a known G-C content value, $f_{GC}$, according to a formula comprising:

$$\frac{1}{T_m(X^{2+})} = \frac{1}{T_m^o} + a + b\ln[X^{2+}] + f_{GC} \cdot (c + d\ln[X^{2+}]) \quad \text{Equation 11}$$

wherein the reference melting temperature is a melting temperature obtained or provided for the polynucleotide at a reference monovalent ion concentration, $[Mon^+]^o$, and wherein each of the coefficients a, b, c, and d is optimized for predicting polynucleotide melting temperatures based on, for example, experimental data.

In another embodiment, the present invention provides a novel method for estimating a melting temperature, $T_m(X^{2+})$, for a polynucleotide at a desired divalent ion concentration, $[X^{2+}]$, and an optionally present monovalent ion concentration $[Mon^+]$, said polynucleotide having a known G-C content value, $f_{GC}$, and length, that is number of base pairs (Nbp), according to a formula comprising:

$$\frac{1}{T_m(X^{2+})} = \frac{1}{T_m^o} + a + b \cdot \ln[X^{2+}] + \quad \text{Equation 12}$$
$$f_{GC} \cdot (c + d \cdot \ln[X^{2+}]) + \left(\frac{e + f \cdot \ln[X^{2+}]}{2 \cdot (N_{bp} - 1)}\right),$$

wherein the reference melting temperature is a melting temperature obtained or provided for the polynucleotide at a reference monovalent ion concentration, $[Mon^+]^o$, wherein each of the coefficients a, b, c, d, e, and f is optimized for predicting polynucleotide melting temperatures based on, for example, experimental data.

In another embodiment, the present invention provides a novel method for estimating a melting temperature, $T_m(X^{2+})$, for a polynucleotide at a desired divalent ion concentration, $[X^{2+}]$, and an optionally present monovalent ion concentration $[Mon^+]$, said polynucleotide having a known G-C content value, $f_{GC}$, and length (Nbp) according to a formula comprising:

$$\frac{1}{T_m(X^{2+})} = \frac{1}{T_m^o} + a + b \cdot \ln[X^{2+}] + \quad \text{Equation 13}$$
$$e + f \cdot \ln[X^{2+}] +$$
$$f_{GC} \cdot (c + d \cdot \ln[X^{2+}]) + \frac{g \cdot (\ln[X^{2+}])^2}{2 \cdot (N_{bp} - 1)},$$

wherein the reference melting temperature is a melting temperature obtained or provided for the polynucleotide at a reference monovalent ion concentration, $[Mon^+]^o$, wherein each of the coefficients a, b, c, d, e, f and g is optimized for predicting polynucleotide melting temperatures based, for example, on experimental data. In some embodiments, the present invention provides a novel method for estimating a melting temperature, $T_m(X^{2+})$, for a polynucleotide at a desired divalent ion concentration, $[X^{2+}]$, and an optionally present monovalent ion concentration $[Mon^+]$, said polynucleotide having a known G-C content value, $f_{GC}$, the method comprising:

(a) obtaining a reference melting temperature, $T_m^o$, for the polynucleotide, said reference melting temperature being a melting temperature obtained or provided for the polynucleotide at a reference monovalent ion concentration, $[Mon^{+o}]$; and (b) modifying the reference melting temperature by adding a term which is a function of the $f_{GC}$ multiplied by a term comprising a logarithm of the divalent cation concentration to determine the melting temperature of the polynucleotide at the desired divalent and monovalent cation concentrations.

In a further embodiment, the present invention provides a novel method for estimating a melting temperature, $T_m(X^{2+})$, for a polynucleotide at a desired divalent ion concentration, $[X^{2+}]$, and an optionally present monovalent ion concentration $[Mon^+]$, said polynucleotide having a known G-C content value, $f_{GC}$, wherein a reference melting temperature, $T_m^o$, is modified by adding a term comprising $a'+b' \cdot \ln[X^{2+}] + f_{GC} \cdot (c'+d' \cdot \ln[X^{2+}])$, wherein the reference melting temperature is a melting temperature obtained or provided for the polynucleotide at a reference monovalent ion concentration, $[Mon^{+o}]$, and wherein each of the coefficients a', b', c', and d' is optimized for predicting polynucleotide melting temperatures based, for example, on experimental data.

In another embodiment, the present invention provides a novel method for estimating a melting temperature, $T_m(X^{2+})$, for a polynucleotide at a desired divalent ion concentration, $[X^{2+}]$, and an optionally present monovalent ion concentration $[Mon^+]$, said polynucleotide having a known G-C content value, $f_{GC}$, according to a formula comprising:

$$T_m(X^{2+}) = T_m^o + a' + b' \cdot \ln[X^{2+}] + f_{GC} \cdot (c' + d' \cdot \ln[X^{2+}]), \quad \text{Equation 14}$$

wherein the reference melting temperature is a melting temperature obtained or provided for the polynucleotide at a reference monovalent ion concentration, $[Mon^{+o}]$, and each of the coefficients a', b', c', and d' is optimized for predicting polynucleotide melting temperatures based, for example, on experimental data.

In another embodiment, the present invention provides a novel method for estimating a melting temperature, $T_m(X^{2+})$, for a polynucleotide at a desired divalent ion concentration, $[X^{2+}]$, and an optionally present monovalent ion concentration $[Mon^+]$, said polynucleotide having a known G-C content value, $f_{GC}$, and length (Nbp) according to a formula comprising:

$$T_m(X^{2+}) = T_m^o + a' + b' \cdot \ln[X^{2+}] + \quad \text{Equation 15}$$
$$f_{GC} \cdot (c' + d' \cdot \ln[X^{2+}]) + \frac{e' + f' \cdot \ln[X^{2+}]}{2 \cdot (N_{bp} - 1)}$$

wherein the reference melting temperature is a melting temperature obtained or provided for the polynucleotide at a reference monovalent ion concentration, $[Mon^{+o}]$, and wherein the number of base pairs, $N_{bp}$, is the number of paired bases in the polynucleotide, and wherein each of the coefficients a', b', c', d', e', and f' is optimized for predicting polynucleotide melting temperatures based on, for example, experimental data.

In another embodiment, the present invention provides a novel method for estimating a melting temperature, $T_m(X^{2+})$, for a polynucleotide at a desired divalent ion concentration,

[X$^{2+}$], and an optionally present monovalent ion concentration [Mon$^+$], said polynucleotide having a known G-C content value, $f_{GC}$, according to a formula comprising:

$$T_m(X^{2+}) = T_m^o + a' + b' \cdot \ln[X^{2+}] + \\ e' + f' \cdot \ln[X^{2+}] + \\ f_{GC} \cdot (c' + d' \cdot \ln[X^{2+}]) + \frac{g' \cdot (\ln[X^{2+}])^2}{2 \cdot (N_{bp} - 1)} \quad \text{Equation 16}$$

wherein the reference melting temperature is a melting temperature obtained or provided for the polynucleotide at a reference monovalent ion concentration, [Mon$^{+o}$], and wherein the number of base pairs, $N_{bp}$, is the number of paired bases in the polynucleotide, and wherein each of the coefficients a', b', c', d', e', f', and g' is optimized for predicting polynucleotide melting temperatures based on, for example, experimental data.

The coefficients of the above methods are each optionally present, and can be found through optimization based on experimental data. For example, they can be obtained from the present invention, such that a' is −4.59 K, b' is 1.06 K, c' is −7.26 K, d' is −1.34 K, e' is 63.3 K, f' is −60.4 K, and g' is −8.78 K when they are present, and especially when [Mon$^+$] is about 1M. The coefficients may also be allowed to vary with monovalent cation concentration.

In a further embodiment, the above methods can be modified by adding one or more additional terms, $$\frac{q \cdot (\ln[X^{2+}])^p}{2 \cdot (N_{bp} - 1)},$$

wherein p is an integer, and q is a coefficient which is optimized for predicting polynucleotide melting temperatures based on, for example, experimental data. When one or more such terms are be added to the formula, the values for p and q may be unique for each additional added term.

The choice of the above methods for estimating the melting temperature, $T_m(X^{2+})$, can be determined by calculating a ratio R of free divalent ion concentrations, [X$^{2+}$], and monovalent ion concentrations, [Mon$^+$], according to the formula $$R = \frac{\sqrt{[X^{2+}]}}{[Mon^+]};$$

and comparing the ratio R to a limiting value.

The present invention further provides a novel computer system that may be used to implement the analytical methods of the invention, including methods of estimating a salt-corrected melting temperature of a polynucleotide. These computer systems comprise a processor interconnected with a memory that contains one or more software components. In particular, the one or more software components include programs that cause the processor to implement steps of the analytical methods described herein. The software components may comprise additional programs and/or files including, for example, but not limited to, sequence or structural databases of polymers.

Computer program products are further provided, which comprise a computer readable medium, such as one or more floppy disks, compact discs (e.g., CD-ROMS or RW-CDS), DVDs, data tapes, etc., that have one or more software components encoded thereon in computer readable form. In particular, the software components may be loaded into the memory of a computer system and may then cause a processor of the computer system to execute steps of the analytical methods described herein. The software components may include additional programs and/or files including databases, e.g., of polymer sequences and/or structures.

A computer system for predicting a melting temperature may comprise:
a memory; and a processor interconnected with the memory and having one or more software components loaded therein, and one or more software components may cause the processor to execute the steps of the invention.

A computer program product for predicting a melting temperature may comprise: a computer readable medium having one or more software components encoded thereon in computer readable form, wherein the one or more software components may be loaded into a memory of a computer system and cause a processor interconnected with said memory to execute steps of the invention.

DETAILED DESCRIPTION OF THE INVENTION

Definitions

Figure 1A:
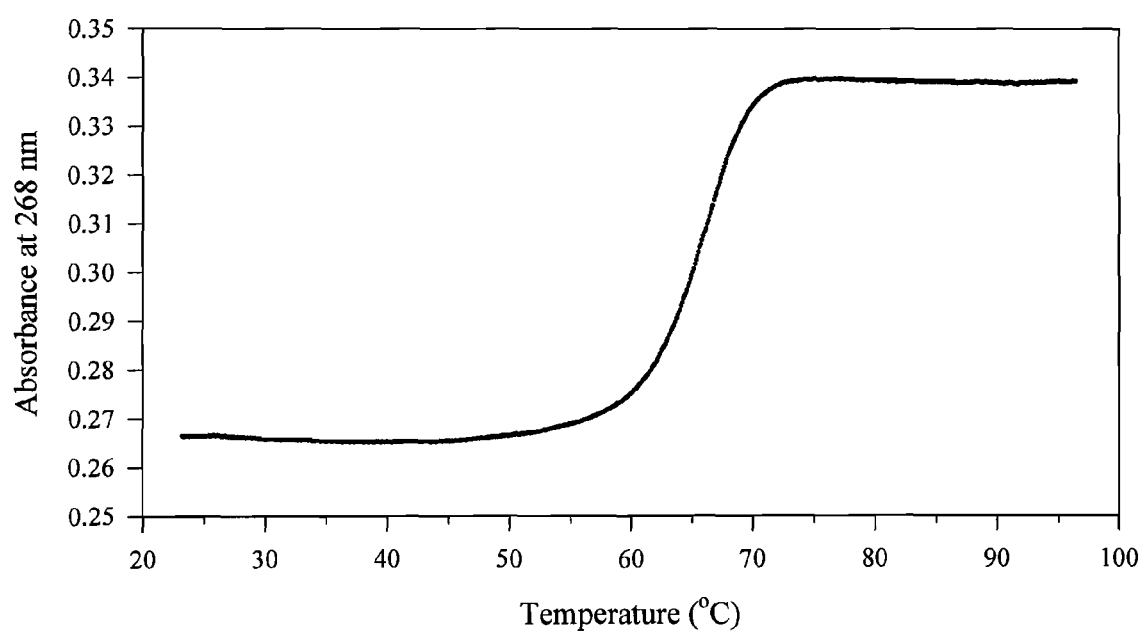
FIG. 1A is a graph showing a UV-melting curve at 268 nm for a 2 μM solution of the oligonucleotide 5'-TACTTCCAGT-GCTCAGCGTA-3' (SEQ ID NO: 31) and its complement dissolved in 3 mM Mg$^{2+}$ and 50 mM KCl PCR buffer.

Melting. The term "melting profile" refers to a collection of measurements of an oligonucleotide and its complement which indicate the oligonucleotide molecule's transition from double-stranded to single-stranded nucleic acid (or vice-versa). The transition of a nucleic acid from double-stranded to single-stranded is often described in the art as the "melting" of that nucleic acid molecule. The transition may also be described as the "denaturation" or "dissociation" of the nucleic acid. Accordingly, a melting profile of the present invention may also be referred to with terms such as "dissociation profile", a "denaturation profile", a "melting curve", a "dissociation curve."

The "melting temperature" or "$T_m$" of a nucleic acid molecule generally refers to the temperature at which a polynucleotide dissociates from its complementary sequence. Generally, the $T_m$ may be defined as the temperature at which one-half of the base pairs in duplex nucleic acid molecules are broken or dissociated (i.e., are "melted") while the other half of the base pairs remain intact in a double stranded conformation (i.e., the fraction of broken based pairs, θ(T)=0.5 when T=$T_m$). In embodiments where duplex nucleic acid molecules are oligonucleotides and in other embodiments where the duplex nucleic acids dissociate in a two-state fashion, the $T_m$ of a nucleic acid may also be defined as the temperature at which one-half of the nucleic acid molecules in a sample are in a single-stranded conformation while the other half of the nucleic acid molecules in that sample are in a double-stranded conformation. $T_m$, therefore, defines a midpoint in the transition from double-stranded to single-stranded nucleic acid molecules (or, conversely, in the transition from single-stranded to double-stranded nucleic acid molecules). It is well appreciated in the art that the transition from double-stranded to single-stranded nucleic acid molecules does not occur at a single temperature but, rather, occurs over a range of temperatures (e.g., typically a narrow range of between about 3 and 10° C.). Nevertheless, the $T_m$ provides a convenient measurement for approximating whether nucleic acid molecules in a sample exist in a single-stranded or double-stranded conformation. As such, the melting temperature of a nucleic acid sample may be readily obtained by simply evaluating a melting profile for that sample.

Ions. The term "Tris" as used herein is an abbreviation for 2-amino-2-(hydroxymethyl)-1,3-propanediol compound.

The term "salt concentration" as used herein is interchangeably used with the term "ion concentration". Types of ions include, but are not limited to, magnesium, potassium, sodium, rubidium, lithium, cesium and francium. Ions may carry a single or multiple charges. The term "divalent cation concentration" or "divalent ion concentration" refers to the free divalent cation concentration, and is calculated from total divalent cation concentration by subtracting those divalent cations that are bound to other compounds in solution. The divalent cation concentration may range from about 0.01 mM to about 5 M, preferably from about 0.1 mM to about 1 M, and more preferably from about 0.5 mM to about 600 mM, and more preferably from about 0.1 mM to about 20 mM.

The term "monovalent cation concentration" or "monovalent ion concentration" refers to the free monovalent cation concentration, and is calculated from total monovalent cation concentration by subtracting those monovalent cations that are bound to other compounds in solution. The monovalent cation concentration may range from 0 to about 5M.

Additional additives may also be present in the reaction buffers. For example, solutions may contain glycerol, ethylene glycol, dimethyl sulfoxide, betaine, tetramethylammonium chloride to name a few.

Nucleic Acids. The methods and algorithms of this invention involve calculating estimated melting temperatures for complementary nucleic acids and can be applied generally to any of the various types of nucleic acids, including but not limited to DNA, RNA, mRNA, cDNA, and cRNA. Polynucleotides that may be used in accordance with the present invention also include double stranded DNA and RNA duplex oligomers, single stranded DNA and RNA. This also includes nucleic acids containing modified bases, for example, but not limited to, thio-uracil, thio-guanine and fluoro-uracil.

As used herein, the terms "polynucleotide", "oligonucleotide" and "oligomers" are interchangeable and are generally used to describe nucleic acid polymers typically having no more than about 500 base pairs. In certain embodiments, the present invention is practiced using oligonucleotides between about 5 and 150 nucleotides in length, preferably between about 5 and 100 nucleotides in length, more preferably between about 10 and 30 nucleotides in length. Oligonucleotides used in the present invention may hybridize to any type of nucleic acid from any source; including but not limited to genomic DNA, mRNA, cDNA, Expressed Sequence Tags (ESTs), and chemically synthesized nucleic acids. Oligonucleotides of the invention may also hybridize to other oligonucleotide molecules.

The nucleic acids may also be modified by many means known in the art. Non-limiting examples of such modifications include methylation, "caps", substitution of one or more of the naturally occurring nucleotides with an analog, and internucleotide modifications such as, for example, but not limited to, those with uncharged linkages (e.g., methylphosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.) and alkylators to name a few. Furthermore, the polynucleotides herein may also be modified with a label capable of providing a detectable signal, either directly or indirectly. Exemplary labels include radioisotopes, fluorescent molecules, biotin and the like.

Oligonucleotides and other polynucleotides can be labeled, e.g., with $^{32}$P-nucleotides or nucleotides to which a label, such as biotin or a fluorescent dye (for example, but not limited to, Cy3 or Cy5) has been covalently conjugated. Generally, oligonucleotides are prepared synthetically, for example, on a nucleic acid synthesizer. Accordingly, oligonucleotides can be prepared with non-naturally occurring phosphoester analog bonds, such as thioester bonds, etc.

Hybridization. A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see, e.g., Sambrook et al., 1989, infra). The conditions of temperature and ionic strength determine the "stringency" of the hybridization.

Hybridization requires that the two nucleic acids contain complementary sequences. However, mismatches between bases are possible depending on the stringency of the hybridization conditions. The appropriate stringency for hybridizing nucleic acids depends on the length of the nucleic acids and the degree of complementarity, variables well known in the art. The greater the degree of similarity or homology between two nucleotide sequences, the greater the value of $T_m$ for a duplex of nucleic acids having those sequences. For duplexes of greater than 100 nucleotides in length, equations for calculating $T_m$ have been derived (see Sambrook et al., 1989, infra, 9.50-9.51). For hybridization with shorter nucleic acids, i.e., oligonucleotides, the position of mismatches becomes more important, and the length of the oligonucleotide determines its specificity (see Sambrook et al., 1989 infra, 11.7-11.8). A minimum length for a hybridizable nucleic acid is at least about 8 nucleotides.

Suitable hybridization conditions for oligonucleotides (e.g., for oligonucleotide probes or primers) are typically somewhat different than for full-length nucleic acids (e.g., full-length cDNA), because of the oligonucleotides' lower melting temperature. Because the melting temperature of oligonucleotides will depend on the length of the oligonucleotide sequences involved, suitable hybridization temperatures will vary depending upon the oligonucleotide molecules and the application. Exemplary temperatures may be 37° C. (for 14-base oligonucleotides), 48° C. (for 17-base oligonucleotides), 55° C. (for 20-base oligonucleotides) and 60° C. (for 23-base oligonucleotides). Exemplary suitable conditions used in PCR experiments include solutions containing 3 mM magnesium chloride, 50 mM potassium chloride, 0.8 mM deoxynucleoside triphosphates and 10 mM Tris-HCl preferably in the range of pH from 6 to 9, or other conditions that afford equivalent levels of hybridization. In other methods, solutions may contain additives or denaturants. For example, dimethyl sulfoxide, formamide, urea, betaine, tetramethylammonium chloride, glycerol, ethylene glycol, Tween 20 are widely used additives in molecular biology methods.

A pair of hybridized polynucleotides may be complementary along their entire length or, alternatively, along only a part of their sequence. In certain embodiments, all of the nucleotides in a pair of hybridized oligonucleotides are complementary. However, mismatch base pairing between complementary nucleic acids may occur, and such nucleic acids are therefore said to be less than 100% complementary. In particular, the extent of complementarity is usually indicated by the fraction (e.g., the percentage) of matched base pairs out of the total number of base pairs in the complementary polynucleotides. It may be that there is at least 99% complementarity between the polynucleotide and its complementary sequence. However, less complementarity may be acceptable or even desirable in some embodiments. For example, in some embodiments, the level of complementary may be as low as 95%, 85% or 75%.

Purification. Nucleic acids can be purified by precipitation, chromatography (including preparative solid phase chromatography), oligonucleotide hybridization, ultracentrifugation, and other means. In one method, nucleic acids are purified using polyacrylamide gel purification (PAGE) techniques. In another embodiment, they are purified using high pressure liquid chromatography (HPLC). Such methods of purification are also well known in the art.

Other Relevant Terms. In certain embodiments, the terms "about" and "approximately" shall generally mean an acceptable degree of error for the quantity measured given the nature or precision of the measurements. Typical, exemplary degrees of error are within 20 percent (%), within 10%, or within 5% of a given value or range of values. Alternatively, and particularly in biological systems, the terms "about" and "approximately" may mean values that are within an order of magnitude, for example, within 5-fold or within 2-fold of a given value. Numerical quantities given herein are approximate unless stated otherwise, meaning that the term "about" or "approximately" can be inferred when not expressly stated.

General Methods

The present invention can be applied to the design of oligonucleotide probes, hybridization and PCR methods, and microarray hybridization methods.

In accordance with the invention, there may be employed conventional molecular biology, microbiology and recombinant DNA techniques within the ordinary skill of the art. Such techniques are explained fully in the literature. See, for example, Sambrook et al. (2001) *Molecular Cloning: A Laboratory Manual*. 3$^{rd}$ ed. Cold Spring Harbor Laboratory Press: Cold Spring Harbor, N.Y.; Sambrook et al. (1989) *Molecular Cloning: A Laboratory Manual*. 2$^{nd}$ ed. Cold Spring Harbor Laboratory Press: Cold Spring Harbor, N.Y.; Ausubel et al. eds. (2006) *Current Protocols in Molecular Biology*. John Wiley and Sons, Inc.: Hoboken, N.J.; Bonifacino et al. eds. (2006) *Current Protocols in Cell Biology*. John Wiley and Sons, Inc.: Hoboken, N.J.; Coligan et al. eds. (2006) *Current Protocols in Immunology*, John Wiley and Sons, Inc.: Hoboken, N.J.; Coico et al. eds. (2006) *Current Protocols in Microbiology*, John Wiley and Sons, Inc.: Hoboken, N.J.; Coligan et al. eds. (2006) *Current Protocols in Protein Science*, John Wiley and Sons, Inc.: Hoboken, N.J.; Enna et al. eds. (2006) *Current Protocols in Pharmacology* John Wiley and Sons, Inc.: Hoboken, N.J.; Hames et al. eds. (1999) *Protein Expression. A Practical Approach*. Oxford University Press: Oxford; Freshney (2000) *Culture of Animal Cells: A Manual of Basic Technique*. 4$^{th}$ ed. Wiley-Liss; among others. The *Current Protocols* listed above are updated several times every year.

Overview of the Method of the Invention

In accordance with the present invention, methods are provided here for estimating a melting temperature, $T_m$, for a polynucleotide or, more specifically, for a polynucleotide and its complementary sequence. Such methods are particularly well suited for the design of oligonucleotide probes and primers, e.g., for use in biological assays such as PCR and nucleic acid hybridization assays. The methods of the invention are robust and straightforward, and provide reliable predictions or estimations of melting temperatures for polynucleotides under conditions that are typically used in such assays. In particular, using the methods of the invention one of ordinary skill in the art may readily determine or estimate melting temperatures for polynucleotides under particular salt conditions and/or may adjust salt conditions for an assay accordingly. Alternatively, the methods of the invention may be used to determine or estimate melting temperatures for a variety of different polynucleotide probes and/or primers in desired salt conditions, and those probes and/or primers having optimal melting temperatures for the assay may then be selected.

In its simplest form, the method of the invention comprises a step of obtaining or determining a "reference" melting temperature for a polynucleotide in a particular monovalent cation concentration (i.e., the "reference" cation concentration) The reference temperature may then be used in accordance with the present invention to obtain or estimate a "salt-corrected" melting temperature therefrom.

Reference melting temperature. A reference melting temperature at a particular monovalent ion concentration may be readily obtained for a particular nucleic acid using any technique known in the art for obtaining or determining melting temperatures. For example, melting temperatures may be experimentally determined for one or more polynucleotides (as described in the Examples, infra) at some standard or reference monovalent ion concentration and these experimentally determined melting temperatures may then be used as reference melting temperatures in accordance with the present invention. However, a reference melting temperature may also be obtained or provided using theoretical, empirical or semi-empirical models that predict melting temperatures at some monovalent ion concentration. In certain embodiments, the reference melting temperature for a polynucleotide is obtained using the "nearest neighbor model", which is well known in the art (see, e.g., Breslauer et al., *Proc. Natl. Acad. Sci. U.S.A.* 1986, 83:3746-3750; Owczarzy et al., *Biopolymers* 1997, 44:217-239; and SantaLucia, *Proc. Natl. Acad. Sci. U.S.A.* 1998, 95:1460). In other embodiments, the $T_m$ monovalent ion correction (e.g., Owczarzy et al., *Biochemistry* 2004, 43:3537-3554) may be applied to predict reference $T_m^\circ$ in 1M Na$^+$ solution from an experimentally determined or predicted melting temperature at other monovalent ion concentrations. Various other models are known in the art and may also be used in accordance with the present invention.

The exact experimental method, model, or formula used to obtain the reference melting temperature is not crucial for practicing the invention. For example and as noted above, the reference melting temperature may be determined experimentally, e.g., by using the melting temperature of a polynucleotide duplex at some reference monovalent ion concentration. However, the melting temperature may also be calculated using some theoretical, empirical or semi-empirical model.

In embodiments where a reference melting temperature is calculated from a theoretical model, the parameters of that model will typically have been calibrated, optimized or otherwise selected for a particular concentration of cations (e.g., for 1 M Na$^+$). One of ordinary skill in the art practicing the invention will appreciate, therefore, that the reference concentration of cations used in such embodiments will preferably be that value for which the theoretical model's parameters have been evaluated.

The model may provide an accurate or reliable estimate of the melting temperature at some monovalent ion concentration for which the model has been optimized. For example, the nearest neighbor model and many other models for predicting melting temperatures use parameters that have been particularly optimized for a 1 M concentration of monovalent cations (specifically, for 1 M Na$^+$). Accordingly, in embodiments where such models are used to obtain a reference melting temperature, the reference monovalent ion concentration may be 1 M. However, the value of $T_m^\circ$ at reference salt concentration may also be calculated from an experimentally determined or calculated melting temperature at another salt concentration using $T_m$ salt correction for monovalent ions (e.g., Owczarzy et al., *Biochemistry* 2004, 43:3537-3554). Generally, one of ordinary skill in the art will readily appreciate for what monovalent ion concentrations a method or model for obtaining melting temperatures has been optimized and, accordingly, will be able to use those monovalent ion concentrations as the "reference" monovalent ion concentration for practicing the methods of this invention. Preferably, both the predicted melting temperature $T_m$ and the reference melting temperature $T_m^\circ$ are specified in Kelvin (K).

Salt concentration. In accordance with the methods of this invention, the melting temperature of a polynucleotide may be readily determined for a particular monovalent ion (denoted [Mon$^+$]) concentration and particular divalent cation concentration (denoted [X$^{2+}$]) of interest to a user. Generally, the cation concentration of interest will correspond to salt conditions for a biological assay (e.g. a PCR or hybridization assay) of particular interest to the user. In certain embodiments of the invention, the divalent cation concentration of interest will be a concentration of free magnesium ions. However, other divalent cations (e.g., calcium, manganese, iron, zinc, copper, nickel, lead, etc.) may be substituted.

The free divalent cation concentration is calculated from total divalent cation concentration by subtracting those divalent cations that are bound to other compounds in solution, for example, but not limited to, deoxynucleoside triphosphates (dNTPs). One of ordinary skill in the art will recognize that free magnesium ion concentration may be calculated by subtracting dNTP concentrations, c(dNTP), from total magnesium concentration, c(Mg$^{2+}$), $$[Mg^{2+}] = c(Mg^{2+}) - c(dNTP).$$

(See von Ahsen et al., *Clin. Chem.* 2001, 47:1956-1961.) The concentration of divalent ions may be compensated for in this manner for any compound which binds the divalent ions, including taking into account the stoichiometry of binding, e.g., $$[X^{2+}] = c(X^{2+}) - c(\text{binding compound}) \times (\text{no. of } X^{2+} \text{ ions bound per binding compound}).$$

Additionally, the monovalent cation concentration, [Mon$^+$], is a sum of concentrations of all monovalent cations in solution; however, H$^+$ ions are not considered. The functional group primarily involved in the buffering action of Tris is an —NH$_2$ group that ionizes to —NH$_3^+$ with a pK$_a$ of 8.3. The pK$_a$ is the pH at which 50% of the buffer concentration is ionized and 50% is not. Because approximately half of the Tris molecules are ionized at pH 8.3 and the experiments of Example 1 were at pH 8.3, in some embodiments, it may be assumed that the monovalent cation concentration is equal to half of the total Tris cation concentration for the calculations. For a typical PCR buffer, concentrations of K$^+$ and Tris$^+$ ions are summed, $$[Mon^+] = [K^+] + [Tris^+] \qquad \text{(Equation 5)}$$

In a more general case, the free monovalent ion concentration is calculated from total monovalent cation concentration by subtracting those monovalent cations that are bound to other compounds in solution [Mon$^+$]=c(Mon$^+$)−c(binding compound)×(no. of Mon$^+$ ions bound per binding compound). In most cases, the binding of monovalent ions to other components in the solution is small and can be neglected.

The formulas presented in this application, as well as the algorithms they represent and illustrate, may be used with any reference monovalent or divalent ions including, but not limited to, magnesium ions (Mg$^{2+}$), manganese ions (Mn$^{2+}$), calcium ions (Ca$^{2+}$), potassium cations (K$^+$), ammonium cations (NH$_4^+$), lithium cations (Li$^+$), rubidium cations (Rb$^+$), cesium cations (Cs$^+$) and francium cations (Fr$^+$). These reference solutions contain cations and may contain various additives or denaturants (e.g., dimethyl sulfoxide, formamide, Tween 20, urea, betaine, tetramethylammonium chloride, glycerol, ethylene glycol).

As demonstrated in the Examples, infra, the methods of the invention are robust, and may be used reliably to determine melting temperatures for a wide range of different monovalent and divalent cation conditions. Divalent cation concentrations may be anywhere from about 0.1 mM to about 1 M, preferably between about 0.5 mM and about 600 mM, more preferably between about 0.5 mM and 125 mM. Monovalent cation concentrations may be anywhere from about 5 mM to about 1.5 M, preferably between about 10 mM and 1.005, more preferably from about 55 mM to 1.005M. However, using empirical techniques that are demonstrated in the below examples, one of ordinary skill in the art can readily optimize the formulas and methods of this invention for any salt concentration or range of salt concentrations of interest. Accordingly, the formulas and techniques described here need not be limited to the specific ranges of salt concentration used in those examples.

Number of base pair value. In certain embodiments, the methods of the invention adjust $T_m$ values based on the lengths of the duplex, denoted by the symbol $N_{bp}$ and equal to the number of bases at each strand. In other embodiments, the $T_m$ values can be predicted or estimated without requiring a correction factor based on the number of base pairs. Overhanging bases at the ends of a duplex are not counted in $N_{bp}$. For example, if two polynucleotides that contain different numbers of nucleotides anneal, all of the paired bases, and none of the unpaired bases, would be included in the $N_{bp}$ value. The $N_{bp}$ value includes nucleotides from one of the stands only, not both stands (see Example 6 if further clarification is needed with regard to the $N_{bp}$ value).

G-C content value. The invention provides methods and formulas which more accurately estimate salt effects on the melting temperature of a polynucleotide. In particular, these methods adjust the "reference" melting temperature in a manner that is dependent upon the polynucleotide's sequence content, specifically the content of guanine (G) and cytosine (C) base pairs that form between a polynucleotide and its complement. Accordingly, the systems and methods of the invention also use a value, referred to herein as the "G-C content value" and denoted by the symbol $f_{GC}$. The G-C content value $f_{GC}$ provides a numerical value which is indicative of the number of G-C base pairs formed between a polynucleotide and its complementary sequence. One of ordinary skill in the art will recognize that adenine (A) and thymine (T) form another type of base pair. In certain embodiments, the G-C content of a polynucleotide may be obtained or provided from the molar fraction of G-C base pairs in the polynucleotide duplex; i.e., $$f_{GC} = \frac{\text{(number of } G-C \text{ base pairs)}}{\text{(number of } G-C \text{ base pairs)} + \text{(number of } A-T \text{ base pairs)}}$$

One of ordinary skill in the art would recognize that $f_{GC} + f_{AT} = 1$, and thus that $f_{GC} = 1 - f_{AT}$, so that $f_{GC}$ can be optionally replaced by $(1 - f_{AT})$.

Estimating Salt Dependent Effects on Melting Temperature

In accordance with the present invention, applicants have discovered novel relationships between the melting temperature of a polynucleotide, $T_m$, the free divalent cation concentration, $[X^{2+}]$, in which the polynucleotide dissociation (or hybridization) occurs, the polynucleotide's G-C content value, $f_{GC}$, a reference temperature, $T_m^o$, calculated at some monovalent ion concentration, and, optionally, the number of base pairs value, $N_{bp}$. Accordingly, the invention provides novel methods for estimating melting temperatures using these novel relationships. Generally speaking, a "reference" melting temperature $T_m^o$ is obtained or provided for the polynucleotide at a "reference" monovalent cation concentration, as described above. The reference melting temperature is then used to calculate a melting temperature, $T_m$, according to a relationship that has been optimized for the polynucleotide's G-C content.

Predictive Formulas. For example, in one embodiment, a melting temperature, $T_m(X^{2+})$, may be estimated or obtained from a reference melting temperature, $T_m^o$, using the formula:

$$\frac{1}{T_m(X^{2+})} = \frac{1}{T_m^o} + a + b\ln[X^{2+}] + f_{GC} \cdot (c + d\ln[X^{2+}]) \quad \text{(Equation 11)}$$

It is noted that for equations such as Equation 11, as well as for other equations throughout the specification based on the reciprocal of the melting temperature (i.e., $1/T_m$), temperatures should be entered in units of Kelvin. One of ordinary skill in the art will be able to readily convert between other scales for measuring temperature (e.g., degrees of Celsius) and units of Kelvin using formulas that are well known and routinely used in the art (for example: K=° C.+273.15). Equation 11 provides an estimate for $T_m$ when working in the 0.5 mM to 50 mM range, and provides an more accurate estimate when working in a the 0.5 mM to 20 mM range.

In another embodiment, a melting temperature, $T_m(X^{2+})$, may be estimated or obtained from a reference melting temperature, $T_m^o$, using the formula:

$$\frac{1}{T_m(X^{2+})} = \frac{1}{T_m^o} + a + b\ln[X^{2+}] + f_{GC} \cdot (c + d\ln[X^{2+}]) + \left(\frac{e + f\ln[X^{2+}]}{2(N_{bp} - 1)}\right) \quad \text{(Equation 12)}$$

Equation 12 provides a more accurate estimate for Tm when working with polynucleotides of varying length.

In yet another embodiment, a melting temperature, $T_m(X^{2+})$, may be estimated or obtained from a reference melting temperature, $T_m^o$, using the formula:

$$\frac{1}{T_m(X^{2+})} = \frac{1}{T_m^o} + a + b\ln[X^{2+}] + \qquad \text{(Equation 13)}$$

$$f_{GC} \cdot (c + d\ln[X^{2+}]) + \left( \frac{e + f\ln[X^{2+}] + g \cdot (\ln[X^{2+}])^2}{2(N_{bp} - 1)} \right)$$

Equation 13 provides an even more accurate estimate for Tm when working with polynucleotides of varying length.

One of ordinary skill in the art will recognize that the terms a+b ln $[X^{2+}]$+$f_{GC}$·(c+d ln $[X^{2+}]$) in equations 11-13 can be very closely approximated by many other mathematical expressions. As such, when practicing the present invention, the terms a+b ln $[X^{2+}]$+$f_{GC}$·(c+d ln $[X^{2+}]$) can be replaced by any such equivalent expression without changing the meaning of said term in equations 11-13 of the invention. For example, the term ln $[X^{2+}]$) can be closely approximated by a polynomial expression using the Taylor expansion, which therefore can also be used when implementing those equations in the in the practice of this invention.

$(f_{GC}+f_{AT})\cdot a+(f_{GC}+f_{AT})\cdot b \ln [X^{2+}]+f_{GC}\cdot (c+d \ln [X^{2+}])$ (Equation 11a)

$f_{GC}\cdot a+f_{AT}\cdot a+f_{GC}\cdot b \ln [X^{2+}]+f_{AT}\cdot b \ln [X^{2+}]+f_{GC}\cdot (c+d \ln [X^{2+}])$ (Equation 11b)

$f_{AT}\cdot a+f_{GC}\cdot (c+a)+[f_{AT}\cdot b+f_{GC}\cdot (b+d)]\times \ln [X^{2+}]$ (Equation 11c)

In many embodiments, the relationship provided in Equations 11-13 may be well approximated by a function linear in the reference melting temperature rather than of its inverse (i.e., $1/T_m$). Such a relationship is less computationally intensive than Equations 11-13 and therefore will be simpler to compute. Accordingly, the use of such a linear approximation may be preferred, particularly when considering the usually relatively narrow range of melting temperatures of nucleic acids; i.e., for physiological temperatures, for example, between about 20 and 80° C. (i.e., between about 293 and 353 K).

Accordingly, in another embodiment, a salt-corrected melting temperature, $T_m(X^{2+})$, may be estimated or obtained from a reference melting temperature using the formula:

$T_m(X^{2+})=T_m^o+a'+b' \ln [X^{2+}]+f_{GC}(c'+d' \ln [X^{2+}])$ (Equation 14)

which is a linear approximation of Equation 11. For equation 11, units of Kelvin and degrees Celsius may be used interchangeably.

In yet another embodiment, a salt-corrected melting temperature, $T_m(X^{2+})$, may be estimated or obtained from a reference melting temperature using the formula:

$$T_m(X^{2+}) = T_m^o + a' + b'\ln[X^{2+}] + \qquad \text{(Equation 15)}$$

$$f_{GC} \cdot (c' + d'\ln[X^{2+}]) + \left( \frac{e' + f'\ln[X^{2+}]}{2(N_{bp} - 1)} \right)$$

which is a linear approximation of Equation 12. Like Equation 12, Equation 15 provides a more accurate estimate of $T_m$ when working with polynucleotides of varying length.

In a further embodiment, a salt-corrected melting temperature, $T_m(X^{2+})$, may be estimated or obtained from a reference melting temperature using the formula:

$$T_m(X^{2+}) = T_m^o + a' + b'\ln[X^{2+}] + \qquad \text{(Equation 16)}$$

$$f_{GC} \cdot (c' + d'\ln[X^{2+}]) + \left( \frac{e' + f'\ln[X^{2+}] + g'(\ln[X^{2+}])^2}{2(N_{bp} - 1)} \right)$$

which is a linear approximation of Equation 13. As in the case of Equation 13, Equation 16 provides a further improved estimate of the $T_m$ when working with polynucleotides of varying length.

Higher Order Terms. Formulas for estimating or providing a salt-corrected melting temperature (e.g., Equations 11-16 above) may be further optimized by the addition of one or more higher order polynomial terms. Thus, for example, embodiments of the invention are also contemplated that may use, e.g., a third order, forth order, and/or even fifth order polynomial term. One of ordinary skill in the art will be able to modify the equations used in this invention to incorporate still higher order polynomial terms; e.g. $(\ln [X^{2+}])^3$, $(\ln [X^{2+}])^4$, $(\ln [X^{2+}])^5$, etc. using routine formulas and methods well known in the mathematical arts.

Formula Coefficients. The coefficients a, b, c, d, e, f, and g in Equations 11-13, and the coefficients a', b', c', d', e', f', and g' in Equations 14-16, may be optimized to determine melting temperatures for polynucleotides having different G-C content, different number of base pairs, different monovalent ion concentrations, and different divalent ions under the salt concentration(s) or range of salt concentrations of interest. For instance, the Examples infra describe experiments when appropriate values for these coefficients are optimized for all of Equations 11-16 above, by optimizing the fit quality to melting data for a plurality of polynucleotide sequences (see the Examples for further clarification.) One of ordinary skill in the art will appreciate that the exact value of the coefficients will depend on which formula (Equations 11-16) is used to estimate or obtain the melting temperature. Therefore, the coefficients may be optimized independently for each formula. Further, when practicing the invention, one should realize that the coefficients depend on the chosen reference monovalent ion concentration, and may be optimized independently for difference reference monovalent ion concentrations.

Applicants have determined that the effect of salt concentration on the melting temperature of a polynucleotide is dependent on the nucleotide sequence. However, as demonstrated herein, such sequence-dependent effects may be accounted for when predicting or estimating $T_m$ values, by simply using terms of Equations 11-16 which are a function of the nucleotide sequence content. In particular and in preferred embodiments of the invention, the terms may be a function of the polynucleotide's G-C content, $f_{GC}$, and, optionally, a polynucleotides' number of base pairs, $N_{bp}$.

In still other embodiments, additional higher order polynomial terms may also be used in Equations 11-16 to estimate salt-corrected melting temperatures with even greater accuracy and reliability. Thus, the invention also contemplates the optional use of third, forth and/or even fifth order polynomial terms. One of ordinary skill in the art will be able to modify the equations used in this invention to incorporate such higher order polynomial terms using routine formulas and methods well known in the mathematical arts. One of ordinary skill in the art will also recognize that, when higher order polynomial terms are used in these equations, it will be necessary to re-optimize the coefficients for optimal results.

It is also noted that the formulas provided in Equations 11-16 are set forth with respect to the "natural logarithm" (i.e., a logarithm of the base e=2.1718) of a cation concentration. As one of ordinary skill in the art will readily appreciate, it may be preferable in many instances to perform calculations using logarithms of a different base (e.g., the logarithm of base 10 or of base 2) which may, for example, be simpler to calculate. The logarithmic terms in Equations 11-16, as well as in the other formulas and equations set forth in this document, may be readily adapted to such other forms by simply making an appropriate adjustment to the coefficient(s); more specifically by multiplying the coefficient(s) by an appropriate factor. One of ordinary skill in the art will be able to readily obtain or determine the appropriate factor(s) and make the necessary adjustment to the logarithmic coefficient(s). Accordingly, it is understood that versions of these equations which use logarithms of other bases are mathematically equivalent to the equations and formulations set forth in this application, and merely provide alternative representations or descriptions of the algorithms and computational methods of this invention. Indeed, one of ordinary skill in the mathematical arts will appreciate that the equations and formulas set forth throughout this application may be written or expressed in a variety of different ways that are mathematically equivalent. Such mathematically equivalent expressions merely represent alternative representations or descriptions of the computational methods that they describe rather than any departure from those methods.

Relative Monovalent/Divalent Cation Concentrations

The coefficients for the above equations can be estimated from fitting the equations to experimentally determined melting temperatures of a set of polynucleotides, and the resulting coefficients may be constant values or functions of the monovalent ion concentration. Whether the coefficients are constant values or functions of monovalent ion concentration depends on the relative concentration of divalent cations, $[X^{2+}]$, and monovalent cations, $[Mon^+]$, in solution. In solutions where divalent cations, $[X^{2+}]$, are "dominant" over monovalent ions, $[Mon^+]$, in their effects on melting temperatures, the coefficients of the above equations are constants and do not vary with $[Mon^+]$. In solutions where neither divalent cations, $[X2^+]$, nor monovalent cations, $[Mon^+]$, are dominant in their effects on melting temperature, the optimal coefficients of the above equations do vary with $[Mon^+]$. Finally, in solutions where monovalent cations, $[Mon^+]$, are "dominant" over divalent cations, $[X2^+]$, in their effects on melting temperatures. Equations which predict melting temperatures based on [Mon+] alone are used, see for example Equation 3.

Applicants have discovered that the ratio, R, $$R=\sqrt{[X^{2+}]}/[Mon^+] \quad \text{(Equation 17)}$$

is a suitable function to show whether divalent ions or monovalent ions are "dominant" in their effects on $T_m$ and whether $T_m$ correction formulae for divalent cations (Equations 11-16) or $T_m$ correction formulae for monovalent cations (for example, Equation 3) are the most accurate and relevant.

Figure 6:
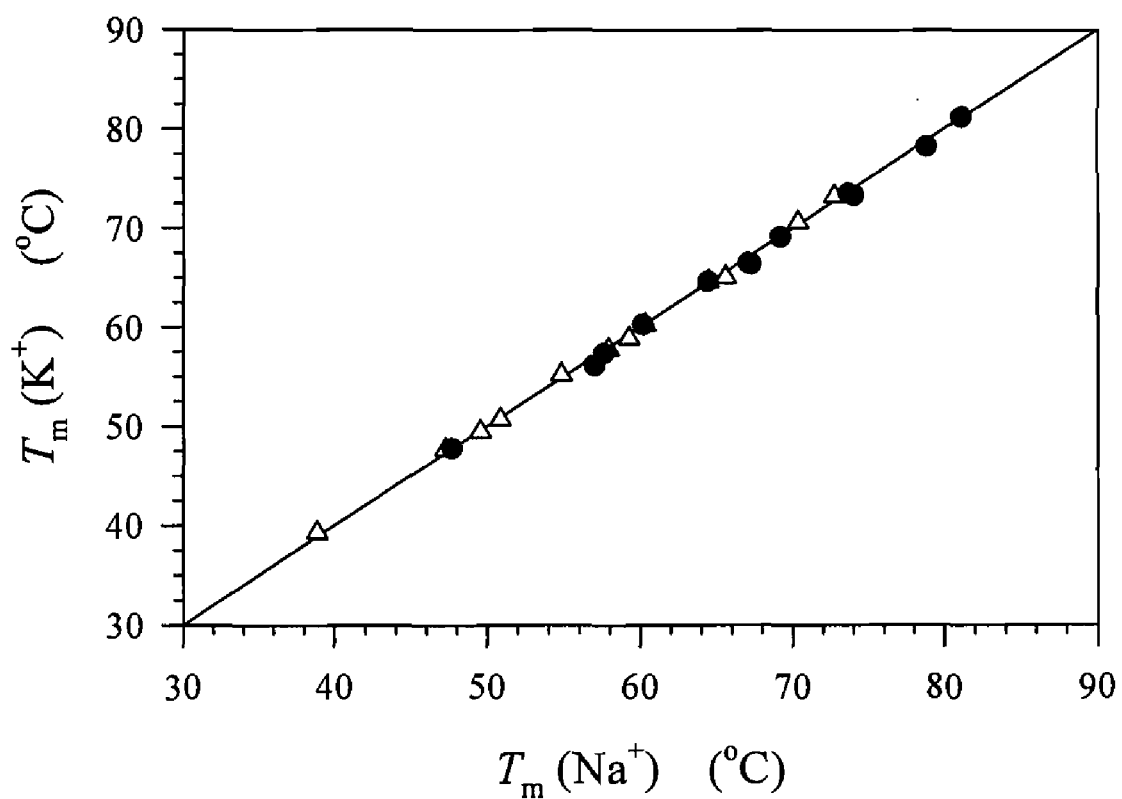
FIG. 6 is a comparison of effects of Na$^+$ and K$^+$ on melting temperatures in buffers of 55 mM (∆) and 205 mM (●) monovalent ion concentrations. Oligonucleotides range in length from 15 to 30 base pairs and are taken from Table I. Melting temperatures determined in 10 mM Tris-HCl, and 50 or 200 mM KCl buffers are plotted versus melting temperatures measured in 10 mM sodium phosphate and NaCl buffers (Owczarzy et al., Biochemistry 2004, 43:3537-3554). Diagonal solid line connects points where melting temperatures in both buffers would be the same.

For example, if the ratio R is equal to or greater than 0.22 for solutions of magnesium and monovalent cations, then $Mg^{2+}$ ions have dominant effects on $T_m$ values and correction formulae for divalent cations (for example, Equations 11-16) are the most accurate. When the ratio R is less than 0.22, $T_m$ correction for monovalent ions (for example, Equation 3) is the most accurate. A flowchart of this algorithm used to select the most accurate $T_m$ correction equation is shown in FIG. 6.

Figure 5:
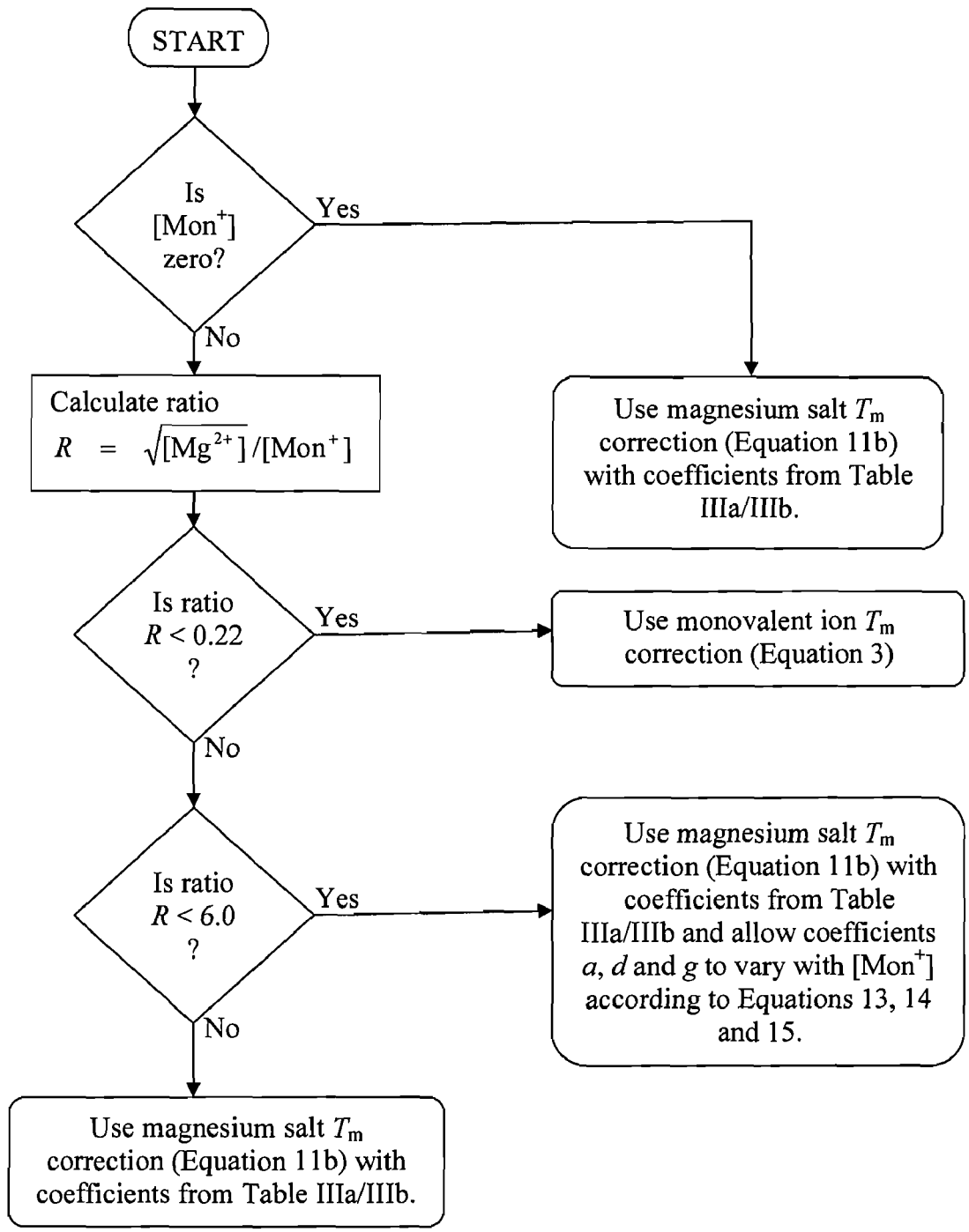
FIG. 5 is a diagram of embodiment of the invented algorithm for solutions containing monovalent and magnesium ions. The algorithm provides the most accurate $T_m$ correction equation based on concentrations of magnesium and monovalent ions.

FIG. 5 illustrates that effects of magnesium and monovalent cations on duplex melting temperature are competitive. Depending on the ratio R of ion concentrations, as determined by Equation 17, melting temperatures are largely determined by the "dominant" ions present.

$T_m$ prediction can be further improved by allowing the coefficients of Equations 11-16 to vary depending upon monovalent cation concentration. For example, additional terms describing the dependence of the coefficients a, b, c, d, e, f, g on $[Mon^+]$ can be used in magnesium buffers where the ratio $$R=\sqrt{[Mg^{2+}]}/[Mon^{30}]$$

is in the range from 0.22 to 6.0. Although Equations 11-16 with constant coefficients are accurate in this range, further improvements of $T_m$ predictions were observed when the coefficients were allowed to vary with $[Mon^+]$. For example, the accuracy of equation 13 was improved in the range of R values from 0.22 to 6.0 when coefficients a, d and g were allowed to vary with $[Mon^+]$ according to Equations 18-20.

$$a=3.92\times10^{-5}(1-0.157-0.352\sqrt{[Mon^+]}\cdot\ln[Mon^+]) \quad \text{(Equation 18)}$$

$$d=1.42\times10^{-5}[1+0.279-4.03\times10^{-3}\ln[Mon^+]-8.03\times10^{-3}(\ln[Mon^+])^2] \quad \text{(Equation 19)}$$

$$g=8.31\times10^{-5}[1-0.514-0.258\ln[Mon^+]+5.25\times10^{-3}(\ln[Mon^+])^3] \quad \text{(Equation 20)}.$$

Temperatures and concentrations have units of Kelvin and mol/L, respectively.

Monovalent cations concentration is a sum of concentrations of all monovalent cations in solution. Concentration of $H^+$ ions is negligible under experimental conditions of interest. Exemplary condition is a typical PCR buffer where concentrations of $K^+$ and $Tris^+$ ions are summed, $$[Mon^+]=[K^+]+[Tris^+] \quad \text{(Equation 5)}$$

Concentrations of cations are under equilibrium conditions. Amounts of basic and acidic forms of buffering compounds vary with pH. Only concentrations of cations are included in Equation 5. For example, Tris at pH 8.3 and 25° C. is about half ionized. Thus, a buffer of 10 mM total Tris concentration at these conditions will contain approximately 5 mM of $Tris^+$ cations and this value is entered into Equation 5.

These equations applied according to the flowchart on FIG. 6 were shown to be accurate for solutions of 0-600 mM $Mg^{2+}$, and 0-1M $K^+$ and pH from 6 to 9. These equations may be less accurate in higher magnesium concentrations, specifically above 1 M $Mg^{2+}$, because $Mg^{2+}$ ions at such high concentrations can bind to additional sites on nucleic acids.

Implementation Systems and Methods

Figure 2:
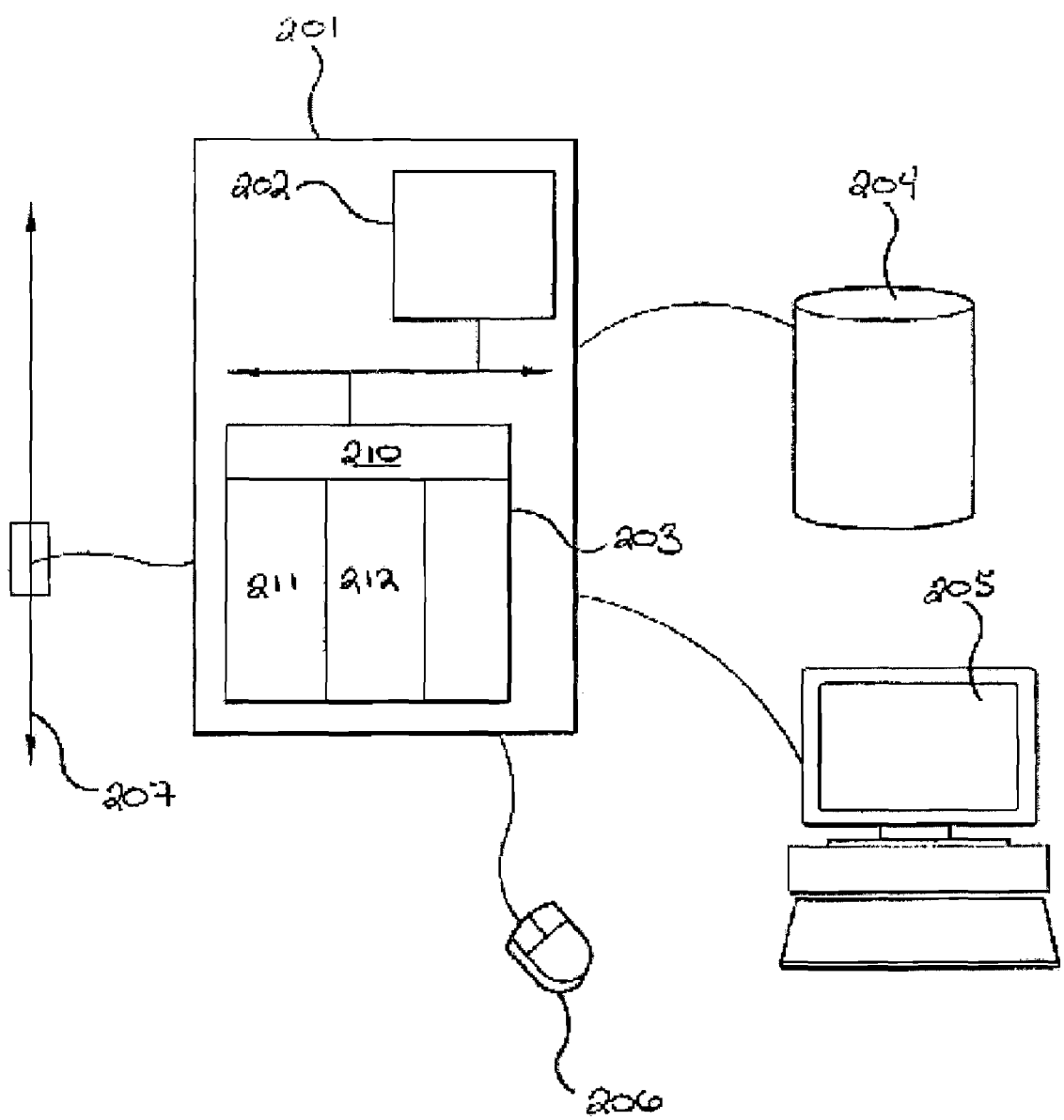
FIG. 2 is a schematic of an exemplary computer system that may be used to implement the analytical methods of the invention.

Computer System. The analytical methods described herein can be implemented by the use of one or more computer systems. FIG. 2 schematically illustrates an exemplary computer system suitable for implementation of the analytical methods of this invention. The components of the computer system 201 include processor element 202 interconnected with a main memory 203. The computer system can contain other components such as a mass storage device 204 and user interface devices 205 including for example, but not limited to, a monitor, a keyboard, and/or pointing devices 206 like a mouse or other graphical input device. The computer system 201 can be linked to a network 207, which can be part of an Ethernet, a local computer system (e.g., as part of a local area network or LAN), and/or a wide area communication network (WAN) such as the Internet.

Typically, one or more software components are loaded into main memory 203 during operation of computer system 201. Software component 210 represents an operating system, which is responsible for managing computer system 201 and its network connections. Software component 211 represents common languages and functions in the system to assist programs implementing the methods specific to the invention. Equations for practicing the methods of the invention can also be programmed and implemented using any programmable spreadsheet software program. Programmable database systems (for example, but not limited to, a SQL database) can be used to program and/or implement the equations and methods of this invention. Thus, software component 212 represents the analytic methods of the invention as programmed in an appropriate procedural language, symbolic package, or the like.

Computer Program Products. The invention also provides computer program products which can be used, e.g., to program or configure a computer system for the implementation of analytical methods of the invention. A computer program product of the invention comprises a computer readable medium such as one or more compact disks (i.e., one or more "CDs", which may be CD-ROMs or a RW-CDs), one or more DVDs, one or more floppy disks (including, for example, but not limited to, one or more ZIP™ disks) or one or more DATs to name a few. The computer readable medium has encoded thereon, in computer readable form, one or more of the software components 212 that, when loaded into memory 203 of a computer system 201, cause the computer system to implement analytic methods of the invention. The computer readable medium may also have other software components encoded thereon in computer readable form. Such other software components may include, for example, but not limited to, functional languages 211 or an operating system 210.

The invention also contemplates the use of the Internet. For example, a web browser may be used as an interface between the user and a server, wherein the user inputs data into the browser, and the data is sent to the server over the Internet. The server may then use the methods of the invention to perform calculations as described within this application and output calculated parameters, e.g., melting temperatures. The server may then provide the calculated parameters through the interface/browser to the user.

System Implementation. In an exemplary implementation, to practice the methods of the invention a G-C content value and/or cation concentrations may be loaded into the computer system 201. For example, the G-C content value may be directly entered by a user from monitor and keyboard 205 by directly typing a sequence of symbols representing numbers (e.g., G-C content value). Alternatively, a user may specify a reference ion concentration, e.g., by selecting an ion concentration from a menu of candidate ion concentrations presented on the monitor or by entering an accession number for a ion concentration in a database and the computer system may access the selected ion concentration from the database, e.g., by accessing a database in memory 203 or by accessing the sequence from a database over the network connection, e.g., over the internet.

Finally, the software components of the computer system, when loaded into memory 203, preferably also cause the computer system to estimate a melting temperature according to the methods described herein. For example, the software components may cause the computer system to use the reference melting temperature of the polynucleotide at a particular reference ion concentration to calculate a modified melting temperature for the polynucleotide at another ion concentration utilizing the methods described herein.

Upon implementing these analytic methods, the computer system preferably then outputs, e.g., the melting temperature for the polynucleotide at a desired ion concentration. The output may be output to the monitor, printed on a printer (not shown), written on mass storage 204 or sent through a computer network (e.g., the internet or an intranet such as a Local Area Network) to one or more other computers.

Alternative systems and methods for implementing the analytic methods of this invention are also intended to be comprehended within the accompanying claims. In particular, the accompanying claims are intended to include the alternative program structures for implementing the methods of this invention that will be readily apparent to one of ordinary skill in the relevant art(s).

EXAMPLES

The present invention is also described by means of the following examples. However, the use of these or other examples anywhere in the specification is illustrative only and in no way limits the scope and meaning of the invention or of any exemplified term. Likewise, the invention is not limited to any particular embodiments described herein. Indeed, many modifications and variations of the invention may be apparent to one of ordinary skill in the art upon reading this specification and can be made without departing from its spirit and scope. The invention is therefore to be limited only by the terms of the appended claims along with the full scope of equivalents to which the claims are entitled.

Example 1

Melting Temperatures of Various Oligomers Measured in Different Salt Conditions

This example describes experiments in which melting profiles were measured for 92 different, exemplary oligonucleotide duplex molecules ranging in length from 10 to 30 base pairs in various salt concentrations. Melting temperatures are extracted from those profiles for each oligonucleotide at each salt concentration observed, and those melting temperatures are provided in the results, infra. Sequence information for each of the exemplary oligonucleotides is also provided. Methods of Moreira et al., *Biochem. Biophys. Res. Commun.* 2005, 327:473-484 and Owczarzy et al., *Biochemistry* 2004, 43:3537-3554 (both of which are incorporated herein by reference in their entireties) were followed according to the below:

Oligonucleotide synthesis and purification. DNA oligonucleotides (SEQ ID NOS:1-92) were synthesized using solid phase phosphoramidite chemistry, deprotected and desalted on NAP-5 columns (Amersham Pharmacia Biotech, Piscataway, N.J.) according to routine techniques (Caruthers et al., *Methods Enzymol.* 1992, 211:3-20). The oligomers were purified using 20% polyacrylamide gel electrophoresis in 1×TBE buffer (50 mM Tris, 50 mM boric acid, 1 mM $Na_2EDTA$). The purity of each oligomer was determined by capillary electrophoresis (CE) carried out on a Beckman PACE 5000 (Beckman Coulter, Inc., Fullerton, Calif.). The CE capillaries had a 11 µm inner diameter and contained ssDNA 100R gel (Beckman-Coulter, Inc., Fullerton, Calif.). Typically, about 0.6 mole of oligonucleotide was injected into a capillary, ran in an electric field of 444 V/cm and detected by UV absorbance at 254 nm. The assays indicated that all oligomers were more than 92% pure.

Compound identity was verified by matrix-assisted laser desorption ionization time-of-flight (MALDI-TOF) mass spectroscopy on a Voyager DE™ Biospectometry™ Work station (Applied Biosystems, Foster, Calif.) or an electrospray ionization-liquid chromatography/mass spectrometry (ESI-LCMS) Oligo HTCS system (Novatia, Princenton, N.J.) following the manufacturer's recommended protocol. Experimental molar masses of all oligomers were within 0.1% of expected molar masses.

Preparation of Magnesium and DNA Samples. in the First Set of Experiments (Examples 1-4), melting studies were carried out in buffers containing 2 mM Tris-HCl with 0.5 mM, 1.5 mM, 3 mM, 10 mM, or 20 mM $MgCl_2$; or in buffers containing 10 mM Tris-HCl with 50 mM, 125 mM, 300 mM or 600 mM $MgCl_2$. These were the lowest concentrations of Tris that exhibited sufficient buffering capacity.

In the second set of experiments (Example 5), competitive effects of $Mg^{2+}$ and $K^+$ ions were examined. Therefore, buffers contained 10 mM Tris-HCl with 0.5 mM, 1.5 mM, 3 mM, 10 mM, 20 mM, 50 mM or 125 mM $MgCl_2$ and with 50 mM, 100 mM, 200 mM, 600 mM or 1M KCl.

Buffer pH was adjusted to 8.3 (at 25° C.) with 0.6 M HCl. Magnesium concentrations of buffers were verified using chelatometric EDTA titrations (Moreira et al., *Biochem. Biophys. Res. Commun.* 2005, 327:473-484) and had errors less than 2%.

The DNA samples were thoroughly dialyzed against melting buffer in a 28-Well Microdialysis System (Invitrogen Corp., Carlsbad, Calif.) following the manufacturer's recommended protocol. Concentrations of DNA oligomers were determined using UV absorbance of the samples at 260 nm in a spectrophotometer (Beckman Coulter, Inc., Fullerton, Calif.), using extinction coefficients for each oligonucleotide that were estimated using the nearest neighbor model for calculating extinction coefficients. (See, Warshaw et al., *J. Mol. Biol.* 1966, 20:29-38. See also, Fasman ed., *Handbook of Biochemistry and Molecular Biology*, vol. 1, CRC Press: Cleveland, Ohio, 1975). Oligomer concentrations were estimated at least twice for each sample. If the estimated concentrations for any sample differed more than 4%, the results were discarded and new absorbance measurements were performed.

To prepare oligonucleotide duplexes, complementary DNA oligomers were mixed in 1:1 molar ratio, heated to 368 K (i.e., 95° C.) and slowly cooled to an ambient temperature. Each solution of duplex DNA was diluted with melting buffer to a total DNA concentration, CT, of 2 μM.

Measurement of UV-melting curves. Melting experiments were conducted on a single beam Beckman DU 650 spectrophotometer (Beckman-Coulter) with a Micro $T_m$ Analysis accessory, a Beckman High Performance Peltier Controller (to regulate the temperature), and 1 cm path-length cuvettes. Melting data were recorded using a PC interfaced to the spectrophotometer. UV-absorbance values at 268 nm wavelength were measured at 0.1 degree increments in the temperature range from 283 to 368 K (i.e., 10-95° C.). Both heating (i.e., "denaturation") and cooling (i.e., "renaturation") transition curves were recorded for each sample at a controlled rate of temperature change (24.9±0.3 Kelvin per hour). Sample temperatures were collected from the internal probe located inside the Peltier holder, and recorded with each sample's UV-absorbance data. Melting profiles were also recorded for samples of buffer alone (no oligonucleotide), and these "blank" profiles were digitally subtracted from melting curves of the DNA samples. To minimize systematic errors, at least three melting curves were collected for each sample in different cuvettes and in different positions within the Peltier holder.

It is well known by those of ordinary skill in the art that a sample of double-stranded nucleic acid molecules absorbs less UV-light than an equivalent sample of single-stranded nucleic acid molecules. Thus, in one certain embodiment, a melting profile may comprise a collection of measurements indicating the UV absorption of a nucleic acid sample over a range of temperatures. Such a collection of measurements was obtained for the melting profiles here, in FIG. 1A, following the procedures described, supra. In such a melting profile, an increase in UV-absorption as the temperature increases will indicate the extent to which more and more base pairs of duplex nucleic acid molecules in the sample are dissociating and an increasing fraction, θ, of those molecules are present in a single-stranded conformation. Conversely, a decrease in UV-absorption as the temperature decreases indicates that more and more base pairs are forming in the sample so that the fraction of double stranded nucleic acid molecules (1-θ) in the sample is increasing while the fraction of single-stranded nucleic acid molecules (θ) is decreasing.

Determination of melting temperatures. To determine each sample's melting temperature, the melting profiles were analyzed using methods that have been previously described (Owczarzy et al., *Biochemistry* 2004, 43:3537-3554). Briefly, the experimental data for each sample was smoothed, using a digital filter, to obtain a plot of the sample's UV-absorbance as a function of its temperature. The fraction of single-stranded oligonucleotide molecules, θ, was then calculated from that plot. The "melting temperature" or "$T_m$" of a sample was defined as the temperature where θ=0.5.

As an example, FIG. 1A shows an exemplary "UV-melting curve" for a 2 μM solution of the oligonucleotide 5'-TACT-TCCAGTGCTCAGCGTA-3' (SEQ ID NO: 31) and its complement dissolved in 3 mM $Mg^{2+}$ and 50 mM KCl PCR buffer. This "melting curve" was obtained as described in the Materials and Method section, supra. Because the solution absorbs more UV-light (260 nm) when the nucleic acid molecules are in a single-stranded conformation then when they are in a double-stranded conformation, the UV-melting curve in FIG. 1A actually monitors the oligonucleotide's transition from the double-stranded to the single-stranded conformation. Inspection of the UV-melting curve reveals that the transition from double to single-stranded conformation does not occur completely at a single temperature, but rather takes place across a range of temperatures. However, this range is very narrow (between about 5-10° C.). Thus, at temperatures above the center of this transition (above about 65.6° C. or 339 K) the oligonucleotides in this sample can generally be regarded as existing in a single-stranded conformation, whereas at temperatures below that "melting temperature" the oligonucleotides in the sample are generally regarded as existing in a double-stranded conformation (i.e., as "duplex" oligonucleotide).

Figure 1B:
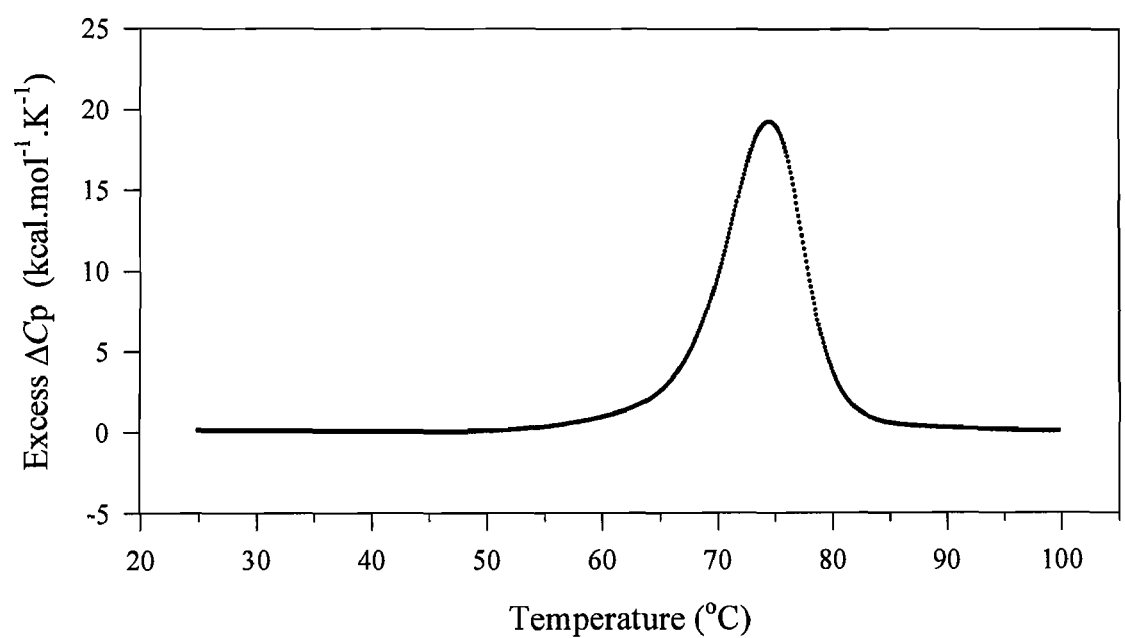
FIG. 1B is a graph showing a differential scanning calorimetry (DSC) curve for a 98 μM solution of the oligonucleotide 5'-TACTTCCAGTGCTCAGCGTA-3' (SEQ ID NO:31) and its complement dissolved in 3 mM Mg$^{2+}$ and 50 mM KCl buffer.

Measurement of melting curves from Differential Scanning Calorimetry, DSC A melting curve for measuring melting temperature may be obtained from differential scanning calorimetry, DSC. The exemplary DSC curve shown in FIG. 1B shows that the melting temperature of a nucleic acid sample may be readily obtained by evaluating a melting profile for that sample from a DSC curve, such as the DSC curve shown in FIG. 1B, in addition to a UV-melting curve, as shown in FIG. 1A. For a detailed description of this experimental technique, see, e.g., Cooper, *Curr. Opinion Chem. Biol.*, 1999, 3:557-563; and Plum & Breslauer, *Curr. Opinion Struct. Biol.*, 1995, 5:682-690.

FIG. 1B shows data from a DSC experiment for a sample of the same oligonucleotide at much higher concentrations (98 μM solution of SEQ ID NO: 31, $C_t$=196 μM, in 3 mM $Mg^{2+}$ and 50 mM KCl buffer). The plot shows the sample's excess heat capacity, $\Delta C_p$, as the temperature is raised from about 293 to about 373 K (i.e., 20° C. to about 100° C.). Heat capacity of the sample increases as the oligonucleotide duplexes in that sample undergo a transition from the double-stranded conformation to the single-stranded conformation. Again, inspection of this figure shows that the transition occurs across a finite but narrow range (e.g., about 5-15 degrees) of temperatures centered at 74.6° C., where the heat absorption is maximal. Thus, again, at temperatures above 74.6° C. (348 K) the oligonucleotides within this sample can generally be regarded as existing in a single-stranded conformation, whereas the oligonucleotides may be generally regarded as existing in a double-stranded conformation at temperatures below 74.6° C.

The observation that this transition (from double-stranded to single-stranded DNA) occurs at a higher temperature for the sample in FIG. 1B (74.6° C.) than for the sample in FIG. 1A (65.6° C.) may be readily attributed to the much higher oligonucleotide concentration in FIG. 1B (196 μM vs. 2 μM) which, as is well known in the art, drives the equilibrium towards the double-stranded nucleic acid conformation.

Melting Temperatures of Various DNA Duplex Oligomers. Oligonucleotides corresponding to each of the sequences set forth in SEQ ID NOS:1-92 and their complementary sequences were synthesized and purified according to the methods described in the Materials and Methods section, supra. For the melting experiments, each of the oligonucleotides (SEQ ID NOS: 1-92) listed in Table I, below, was mixed in a 1:1 molar ratio with its 100% complementary sequence, as described in Material and Methods Section, supra. Melting profiles were then recorded for each oligomer in 0.5 mM, 1.5 mM, 3 mM, 10 mM, 20 mM, 50 mM, 125 mM, 300 mM and 600 mM [$Mg^{2+}$], and the melting temperature was extracted from each profile. The experimentally determined $T_m$ values for each sample were reproducible within 0.3° C. Denaturation and renaturation melting profiles were superimposable indicating equilibrium conditions.

The $T_m$ values obtained for each oligomer are provided in Tables I and II, below. In this first example of experiments, buffers did not contain potassium ions. For convenience, the melting temperatures specified in Tables I and II are listed in units of Kelvin (K), which may be used in the implementation of this invention. However, one of ordinary skill in the art will be able to readily convert between units of Kelvin and other scales or units for measuring temperature (e.g., degrees Celsius) using formulas that are well known and routinely used in the art (for example, K=° C.+273.15). Sequence information was also recorded for each oligomer, including the number of base pairs, $N_{bp}$, and the G-C content. Specifically, an oligomer's G-C content $f_{GC}$ is defined here as the fraction of bases that are either guanine or cytosine. Thus, for example, the oligonucleotide set forth in SEQ ID NO:1 comprises a total of 15 bases pairs (i.e., $N_{bp}$=15), of which three are either guanine (zero) or cytosine (three). Thus, that particular oligomer's G-C content may be obtained or provided by: $f_{GC}$=3/15=0.2. The nucleotide sequence, total number of base pairs and G-C content for each oligomer are also provided in Tables I and II, along with the corresponding SEQ ID NO.

TABLE I

Melting Temperatures of 92 DNA Duplex Oligomers in Tris-HCl Buffers with Various [$Mg^{2+}$], no KCl, and [DNA] = 2 μM

| SEQ ID NO: | $N_{bp}$ $f_{GC}$ | Sequence (5' to 3') | 2 mM Tris-HCl | | | | | 10 mM Tris-HCl | |
|---|---|---|---|---|---|---|---|---|---|
| | | | Melting temperatures (K) at $Mg^{2+}$ concentration (mM) | | | | | | |
| | | | 0.5 mM | 1.5 mM | 3 mM | 10 mM | 20 mM | 50 mM | 125 mM |
| 1 | 15 0.20 | TACTAACATTAACTA | 312.4 | 316.0 | 317.5 | 320.3 | 320.6 | 321.5 | 322.1 |
| 2 | 15 0.27 | ATACTTACTGATTAG | 313.0 | 316.7 | 318.1 | 319.9 | 321.0 | 321.8 | 322.4 |
| 3 | 15 0.33 | GTACACTGTCTTATA | 316.5 | 320.3 | 321.8 | 323.7 | 324.4 | 325.3 | 325.6 |
| 4 | 15 0.33 | GTATGAGAGACTTTA | 316.6 | 320.1 | 321.7 | 324.1 | 324.6 | 325.4 | 326.0 |
| 5 | 15 0.33 | TTCTACCTATGTGAT | 316.4 | 319.2 | 321.0 | 323.4 | 323.5 | 324.1 | 324.6 |
| 6 | 15 0.40 | AGTAGTAATCACACC | 319.7 | 322.6 | 324.1 | 326.2 | 326.6 | 327.2 | 327.6 |
| 7 | 15 0.40 | ATCGTCTCGGTATAA | 321.1 | 324.2 | 325.8 | 327.9 | 328.3 | 328.7 | 329.5 |
| 8 | 15 0.47 | ACGACAGGTTTACCA | 324.7 | 327.7 | 329.1 | 331.3 | 331.7 | 332.1 | 332.6 |
| 9 | 15 0.47 | CTTTCATGTCCGCAT | 325.9 | 328.3 | 329.6 | 331.5 | 332.1 | 332.7 | 332.8 |
| 10 | 15 0.47 | TGGATGTGTGAACAC | 323.0 | 326.6 | 327.9 | 329.8 | 330.4 | 331.0 | 331.4 |
| 11 | 15 0.53 | ACCCCGCAATACATG | 325.8 | 328.5 | 329.8 | 331.6 | 332.2 | 332.0 | 332.4 |
| 12 | 15 0.43 | GCAGTGGATGTGAGA | 325.5 | 328.3 | 329.6 | 331.2 | 331.8 | 332.4 | 332.2 |

TABLE I-continued

Melting Temperatures of 92 DNA Duplex Oligomers in Tris-HCl Buffers with Various [$Mg^{2+}$], no KCl, and [DNA] = 2 µM

| SEQ ID NO: | $N_{bp}$ $f_{GC}$ | Sequence (5' to 3') | 2 mM Tris-HCl | | | | | 10 mM Tris-HCl | |
|---|---|---|---|---|---|---|---|---|---|
| | | | Melting temperatures (K) at $Mg^{2+}$ concentration (mM) | | | | | | |
| | | | 0.5 mM | 1.5 mM | 3 mM | 10 mM | 20 mM | 50 mM | 125 mM |
| 13 | 15 0.53 | GGTCCTTACTTGGTG | 323.5 | 326.5 | 327.9 | 329.7 | 330.3 | 330.6 | 330.7 |
| 14 | 15 0.60 | CGCCTCATGCTCATC | 327.5 | 330.4 | 331.8 | 333.3 | 333.8 | 334.4 | 334.2 |
| 15 | 15 0.67 | AAATAGCCGGGCCGC | 333.6 | 336.6 | 337.7 | 339.3 | 339.5 | 340.2 | 340.3 |
| 16 | 15 0.67 | CCAGCCAGTCTCTCC | 329.7 | 332.6 | 333.7 | 335.2 | 335.6 | 336.1 | 336.1 |
| 17 | 15 0.67 | GACGACAAGACCGCG | 332.5 | 334.9 | 336.0 | 337.3 | 337.7 | 338.4 | 338.1 |
| 8 | 15 0.73 | CAGCCTCGTCGCAGC | 335.0 | 337.3 | 338.5 | 340.0 | 340.4 | 340.6 | 340.5 |
| 19 | 15 0.73 | CTCGCGGTCGAAGCG | 334.5 | 337.1 | 338.3 | 339.4 | 340.0 | 340.4 | 339.9 |
| 20 | 15 0.80 | GCGTCGGTCCGGGCT | 338.4 | 340.7 | 341.7 | 342.7 | 343.5 | 343.7 | 343.3 |
| 21 | 20 0.20 | TATGTATATTTTGTAATCAG | 321.7 | 324.5 | 325.7 | 327.5 | 328.2 | 328.9 | 329.4 |
| 22 | 20 0.25 | TTCAAGTTAAACATTCTATC | 323.1 | 325.7 | 327.1 | 328.8 | 329.6 | 330.4 | 331.0 |
| 23 | 20 0.30 | TGATTCTACCTATGTGATTT | 324.9 | 327.7 | 328.9 | 330.8 | 331.4 | 332.4 | 332.7 |
| 24 | 20 0.35 | GAGATTGTTTCCCTTTCAAA | 326.4 | 329.3 | 330.7 | 332.4 | 333.3 | 334.0 | 334.4 |
| 25 | 20 0.40 | ATGCAATGCTACATATTCGC | 330.5 | 333.1 | 334.1 | 335.7 | 336.3 | 337.0 | 336.9 |
| 26 | 20 0.40 | CCACTATACCATCTATGTAC | 326.1 | 328.6 | 329.8 | 331.2 | 331.9 | 332.3 | 332.6 |
| 27 | 20 0.45 | CCATCATTGTGTCTACCTCA | 331.2 | 333.6 | 334.7 | 336.0 | 336.6 | 337.2 | 337.2 |
| 28 | 20 0.45 | CGGGACCAACTAAAGGAAAT | 330.7 | 333.3 | 334.6 | 336.0 | 336.6 | 337.1 | 337.6 |
| 29 | 20 0.45 | TAGTGGCGATTAGATTCTGC | 333.2 | 335.6 | 336.7 | 338.0 | 338.8 | 339.4 | 339.6 |
| 30 | 20 0.50 | AGCTGCAGTGGATGTGAGAA | 334.2 | 336.8 | 338.0 | 339.5 | 340.0 | 340.8 | 340.4 |
| 31 | 20 0.50 | TACTTCCAGTGCTCAGCGTA | 335.3 | 337.8 | 339.0 | 340.4 | 340.8 | 341.4 | 341.5 |
| 32 | 20 0.55 | CAGTGAGACAGCAATGGTCG | 334.5 | 337.0 | 338.2 | 339.4 | 339.9 | 340.3 | 340.2 |
| 33 | 20 0.55 | CGAGCTTATCCCTATCCCTC | 333.2 | 335.6 | 336.7 | 338.1 | 338.6 | 339.1 | 339.0 |
| 34 | 20 0.55 | CGTACTAGCGTTGGTCATGG | 334.3 | 336.5 | 337.5 | 339.0 | 339.3 | 339.7 | 339.6 |
| 35 | 20 0.60 | AAGGCGAGTCAGGCTCAGTG | 339.3 | 341.6 | 342.9 | 343.8 | 344.4 | 344.7 | 344.6 |

TABLE I-continued

Melting Temperatures of 92 DNA Duplex Oligomers in Tris-HCl Buffers with Various [Mg$^{2+}$], no KCl, and [DNA] = 2 μM

| SEQ ID NO: | $N_{bp}$ $f_{GC}$ | Sequence (5' to 3') | 2 mM Tris-HCl Melting temperatures (K) at Mg$^{2+}$ concentration (mM) | | | | | 10 mM Tris-HCl | |
|---|---|---|---|---|---|---|---|---|---|
| | | | 0.5 mM | 1.5 mM | 3 mM | 10 mM | 20 mM | 50 mM | 125 mM |
| 36 | 20 0.60 | ACCGACGACGCTGATCCGAT | 339.4 | 341.8 | 342.7 | 344.2 | 344.1 | 344.8 | 344.4 |
| 37 | 20 0.65 | AGCAGTCCGCCACACCCTGA | 340.8 | 343.1 | 343.8 | 345.3 | 345.6 | 345.9 | 345.5 |
| 38 | 20 0.70 | CAGCCTCGTTCGCACAGCCC | 342.1 | 344.5 | 345.4 | 346.6 | 347.1 | 347.3 | 347.0 |
| 39 | 20 0.75 | GTGGTGGGCCGTGCGCTCTG | 342.9 | 345.2 | 346.3 | 347.5 | 347.8 | 348.1 | 347.6 |
| 40 | 20 0.80 | GTCCACGCCCGGTGCGACGG | 343.5 | 345.6 | 347.0 | 347.2 | 347.6 | 347.8 | 347.4 |
| 41 | 25 0.20 | GATATAGCAAAATTCTAAGTTAATA | 327.4 | 330.0 | 331.1 | 332.9 | 334.0 | 334.4 | 335.0 |
| 42 | 25 0.32 | ATAACTTTACGTGTGTGACCTATTA | 333.0 | 335.5 | 336.6 | 338.1 | 338.6 | 339.3 | 339.5 |
| 43 | 25 0.32 | GTTCTATACTCTTGAAGTTGATTAC | 330.4 | 332.8 | 334.0 | 335.6 | 336.1 | 336.9 | 337.1 |
| 44 | 25 0.36 | CCCTGCACTTTAACTGAATTGTTTA | 333.9 | 336.3 | 337.3 | 338.8 | 339.2 | 339.9 | 340.2 |
| 45 | 25 0.36 | TAACCATACTGAATACCTTTTGACG | 332.9 | 335.2 | 336.2 | 337.6 | 338.2 | 338.8 | 339.0 |
| 46 | 25 0.40 | TCCACACGGTAGTAAAATTAGGCTT | 335.6 | 337.9 | 338.8 | 340.1 | 341.2 | 341.3 | 341.3 |
| 47 | 25 0.40 | TTCCAAAAGGAGTTATGAGTTGCGA | 335.3 | 337.5 | 338.7 | 340.0 | 340.5 | 341.1 | 341.2 |
| 48 | 25 0.44 | AATATCTCTCATGCGCCAAGCTACA | 337.6 | 340.1 | 341.0 | 342.3 | 342.6 | 343.4 | 343.2 |
| 49 | 25 0.44 | TAGTATATCGCAGCATCATACAGGC | 336.1 | 338.2 | 339.3 | 341.1 | 341.0 | 341.5 | 341.5 |
| 50 | 25 0.44 | TGGATTCTACTCAACCTTAGTCTGG | 335.4 | 337.6 | 338.7 | 340.0 | 340.5 | 341.0 | 341.0 |
| 51 | 25 0.48 | CGGAATCCATGTTACTTCGGCTATC | 337.1 | 339.4 | 340.3 | 341.7 | 342.1 | 342.6 | 342.6 |
| 52 | 25 0.52 | CTGGTCTGGATCTGAGAACTTCAGG | 338.7 | 340.8 | 341.8 | 343.0 | 343.5 | 343.8 | 343.8 |
| 53 | 25 0.56 | ACAGCGAATGGACCTACGTGGCCTT | 343.1 | 345.1 | 346.1 | 347.1 | 347.3 | 347.5 | 347.4 |
| 54 | 25 0.56 | AGCAAGTCGAGCAGGGCCTACGTTT | 343.4 | 345.4 | 346.5 | 347.3 | 347.9 | 348.2 | 348.2 |
| 55 | 25 0.56 | GCGAGCGACAGGTTACTTGGCTGAT | 342.6 | 344.6 | 345.6 | 346.5 | 347.1 | 347.4 | 347.1 |
| 56 | 25 0.60 | AAAGGTGTCGCGGAGAGTCGTGCTG | 344.0 | 346.3 | 347.1 | 348.4 | 348.8 | 348.9 | 348.6 |
| 57 | 25 0.68 | ATGGGTGGGAGCCTCGGTAGCAGCC | 345.3 | 347.6 | 348.4 | 349.6 | 349.8 | 350.0 | 349.9 |
| 58 | 25 0.72 | CAGTGGGCTCCTGGGCGTGCTGGTC | 346.6 | 348.5 | 349.3 | 350.4 | 350.7 | 351.4 | 350.6 |

TABLE I-continued

Melting Temperatures of 92 DNA Duplex Oligomers in Tris-HCl Buffers with Various [$Mg^{2+}$], no KCl, and [DNA] = 2 µM

| SEQ ID NO: | $N_{bp}$ $f_{GC}$ | Sequence (5' to 3') | 2 mM Tris-HCl Melting temperatures (K) at $Mg^{2+}$ concentration (mM) | | | | | 10 mM Tris-HCl | |
|---|---|---|---|---|---|---|---|---|---|
| | | | 0.5 mM | 1.5 mM | 3 mM | 10 mM | 20 mM | 50 mM | 125 mM |
| 59 | 25 0.72 | GCCAACTCCGTCGCCGTTCGTGCGC | 346.9 | 348.8 | 349.6 | 350.3 | 350.6 | 350.8 | 350.7 |
| 60 | 25 0.80 | ACGGGTCCCCGCACCGCACCGCCAG | 350.4 | 352.1 | 352.9 | 353.4 | 353.7 | 353.9 | 353.5 |
| 61 | 30 0.20 | TTATGTATTAAGTTATATAGTAGTAGTAGT | 328.2 | 330.7 | 331.7 | 333.2 | 333.7 | 334.5 | 334.9 |
| 62 | 30 0.23 | ATTGATATCCTTTTCTATTCATCTTTCATT | 332.0 | 334.4 | 335.5 | 336.9 | 337.5 | 338.2 | 338.7 |
| 63 | 30 0.30 | AAAGTACATCAACATAGAGAATTGCATTTC | 334.6 | 336.9 | 337.9 | 339.1 | 339.7 | 340.3 | 340.7 |
| 64 | 30 0.30 | CTTAAGATATGAGAACTTCAACTAATGTGT | 334.1 | 336.3 | 337.2 | 338.6 | 339.2 | 340.3 | 340.3 |
| 65 | 30 0.37 | CTCAACTTGCGGTAAATAAATCGCTTAATC | 337.2 | 339.3 | 340.3 | 341.5 | 342.0 | 342.7 | 342.9 |
| 66 | 30 0.37 | TATTGAGAACAAGTGTCCGATTAGCAGAAA | 338.4 | 340.6 | 341.5 | 342.8 | 343.2 | 343.8 | 344.0 |
| 67 | 30 0.40 | GTCATACGACTGAGTGCAACATTGTTCAAA | 338.6 | 340.8 | 341.6 | 342.9 | 343.2 | 343.8 | 344.0 |
| 68 | 30 0.43 | AACCTGCAACATGGAGTTTTTGTCTCATGC | 341.0 | 343.1 | 344.0 | 344.8 | 345.5 | 345.9 | 346.0 |
| 69 | 30 0.43 | CCGTGCGGTGTGTACGTTTTATTCATCATA | 339.8 | 341.9 | 342.7 | 343.9 | 344.4 | 344.8 | 344.7 |
| 70 | 30 0.47 | GTTCACGTCCGAAAGCTCGAAAAAGGATAC | 341.3 | 343.4 | 344.3 | 345.3 | 345.9 | 346.3 | 346.6 |
| 71 | 30 0.50 | AGTCTGGTCTGGATCTGAGAACTTCAGGCT | 343.0 | 344.8 | 345.7 | 346.7 | 347.1 | 347.3 | 347,6 |
| 72 | 30 0.50 | TCGGAGAAATCACTGAGCTGCCTGAGAAGA | 342.1 | 344.1 | 345.1 | 346.0 | 346.5 | 346.9 | 346.8 |
| 73 | 30 0.57 | CTTCAACGGATCAGGTAGGACTGTGGTGGG | 341.4 | 343.2 | 344.2 | 345.2 | 345.6 | 346.1 | 346.1 |
| 74 | 30 0.60 | ACGCCCACAGGATTAGGCTGGCCCACATTG | 346.3 | 348.1 | 349.0 | 349.8 | 350.1 | 350.5 | 350.3 |
| 75 | 30 0.60 | GTTATTCCGCAGTCCGATGGCAGCAGGCTC | 346.0 | 347.9 | 348.7 | 349.8 | 350.1 | 350.5 | 350.2 |
| 76 | 30 0.63 | TCAGTAGGCGTGACGCAGAGCTGGCGATGG | 346.8 | 348.9 | 349.1 | 350.1 | 350.9 | 351.2 | 350.9 |
| 77 | 30 0.67 | CGCGCCACGTGTGATCTACAGCCGTTCGGC | 347.0 | 348.4 | 349.1 | 350.2 | 350.1 | 350.6 | 350.2 |
| 78 | 30 0.70 | GACCTGACGTGGACCGCTCCTGGGCGTGGT | 349.3 | 350.9 | 351.7 | 352.6 | 352.8 | 353.2 | 353.0 |
| 79 | 30 0.77 | GCCCCTCCACTGGCCGACGGCAGCAGGCTC | 350.7 | 352.2 | 353.0 | 353.6 | 354.0 | 354.1 | 353.8 |
| 80 | 30 0.80 | CGCCGCTGCCGACTGGAGGAGCGCGGACG | 351.8 | 353.2 | 354.0 | 354.2 | 354.8 | 354.8 | 354.3 |
| 81 | 10 0.20 | ATCAATCATA | 295.1 | 298.7 | 300.6 | 303.0 | 304.0 | 306.2 | 306.3 |

TABLE I-continued

Melting Temperatures of 92 DNA Duplex Oligomers in Tris-HCl Buffers with Various [$Mg^{2+}$], no KCl, and [DNA] = 2 μM

| SEQ ID NO: | $N_{bp}$ $f_{GC}$ | Sequence (5' to 3') | 2 mM Tris-HCl Melting temperatures (K) at $Mg^{2+}$ concentration (mM) | | | | | 10 mM Tris-HCl | |
|---|---|---|---|---|---|---|---|---|---|
| | | | 0.5 mM | 1.5 mM | 3 mM | 10 mM | 20 mM | 50 mM | 125 mM |
| 82 | 10 0.30 | TTGTAGTCAT | 300.3 | 304.0 | 305.5 | 308.0 | 309.2 | 310.4 | 310.7 |
| 83 | 10 0.30 | GAAATGAAAG | 297.7 | 300.6 | 303.7 | 304.6 | 307.0 | 307.8 | 308.5 |
| 84 | 10 0.40 | CCAACTTCTT | 303.2 | 308.4 | 309.6 | 312.5 | 312.9 | 313.6 | 313.4 |
| 85 | 10 0.50 | ATCGTCTGGA | 308.3 | 312.1 | 313.7 | 317.0 | 316.5 | 316.9 | 317.5 |
| 86 | 10 0.50 | AGCGTAAGTC | 302.8 | 309.3 | 310.7 | 312.5 | 314.0 | 315.3 | 315.6 |
| 87 | 10 0.60 | CGATCTGCGA | 311.5 | 316.4 | 317.2 | 320.8 | 320.8 | 320.4 | 320.7 |
| 88 | 10 0.70 | TGGCGAGCAC | 318.4 | 322.8 | 323.7 | 325.9 | 326.4 | 327.3 | 327.6 |
| 89 | 10 0.70 | GATGCGCTCG | 317.2 | 320.9 | 322.0 | 323.8 | 324.4 | 324.7 | 325.0 |
| 90 | 10 0.80 | GGGACCGCCT | 321.5 | 325.1 | 326.9 | 328.6 | 329.0 | 328.6 | 329.2 |
| 91 | 11 0.55 | CGTACACATGC | 313.3 | 317.4 | 318.8 | 321.2 | 321.2 | 321.3 | 321.8 |
| 92 | 11 0.55 | CCATTGCTACC | 312.0 | 315.8 | 317.3 | 319.5 | 320.1 | 320.4 | 320.7 |

TABLE II

Melting Temperatures of Selected DNA Duplex Oligomers in Tris-HCl Buffers with Various [$Mg^{2+}$], no KCl, and [DNA] = 2 μM

| SEQ ID NO: | $N_{bp}$ $f_{GC}$ | (5' to 3') | 10 mM Tris-HCl Melting temperatures (K) at $Mg^{2+}$ concentrations (mM) | |
|---|---|---|---|---|
| | | | 300 mM | 600 mM |
| 5 | 15 0.33 | TTCTACCTATGTGAT | 323.9 | 322.6 |
| 12 | 15 0.53 | GCAGTGGATGTGAGA | 331.3 | 329.3 |
| 18 | 15 0.73 | CAGCCTCGTCGCAGC | 338.7 | 336.9 |
| 23 | 20 0.30 | TGATTCTACCTATGTGATTT | 331.9 | 330.8 |
| 30 | 20 0.50 | AGCTGCAGTGGATGTGAGAA | 339.4 | 337,9 |
| 38 | 20 0.70 | CAGCCTCGTTCGCACAGCCC | 345.5 | 343.5 |
| 43 | 25 0.32 | GTTCTATACTCTTGAAGTTGATTAC | 336.7 | 335.7 |

TABLE II-continued

Melting Temperatures of Selected DNA Duplex Oligomers in Tris-HCl Buffers with Various [Mg$^{2+}$], no KCl, and [DNA] = 2 μM

| SEQ ID NO: | $N_{bp}$ $f_{GC}$ | (5' to 3') | 10 mM Tris-HCl Melting temperatures (K) at Mg$^{2+}$ concentrations (mM) | |
|---|---|---|---|---|
| | | | 300 mM | 600 mM |
| 52 | 25 0.52 | CTGGTCTGGATCTGAGAACTTCAGG | 343.0 | 341.7 |
| 58 | 25 0.72 | CAGTGGGCTCCTGGGCGTGCTGGTC | 349.0 | 347.1 |
| 64 | 30 0.30 | CTTAAGATATGAGAACTTCAACTAATGTGT | 339.3 | 338.4 |
| 71 | 30 0.50 | AGTCTGGTCTGGATCTGAGAACTTCAGGCT | 346.6 | 345.3 |
| 78 | 30 0.70 | GACCTGACGTGGACCGCTCCTGGGCGTGGT | 351.2 | 349.6 |
| 82 | 10 0.30 | TTGTAGTCAT | 310.3 | 308.6 |
| 85 | 10 0.50 | ATCGTCTGGA | 316.2 | 314.7 |
| 89 | 10 0.70 | GATGCGCTCG | 323.1 | 320.8 |
| 90 | 10 0.80 | GGGACCGCCT | 328.1 | 325.4 |
| 91 | 11 0.55 | CGTACACATGC | 320.1 | 318.0 |
| 92 | 11 0.55 | CCATTGCTACC | 320.2 | 318.0 |

Example 2

Determination of Coefficient Values of Equations 13 and 16 Based on the Data of Example 1

Coefficients. The experimentally determined melting temperatures set forth in Tables I and II, supra, were fit to Equations 13 and 16 to determine the value of their coefficients.

In each analysis of this Example, a reference salt concentration of [Na$^+$]$_0$=1.0 M was used, and the reference melting temperature, $T_m^o$, was the oligomer's experimentally determined melting temperature at that cation concentration. This reference set of melting temperatures in 1.0 M Na$^+$ buffer was published in Owczarzy et al., *Biochemistry* 2004, 43:35367-3554.

The coefficients in Equation 13 and 16 were derived from experimentally measured $T_m(Mg^{2+})$ and $T_m^o$ values using multiple linear regression fit.

Equation 13 describes the fit of $1/T_m$ and $1/T_m^o$ differences and is consistent with the previously published $T_m$ correction for sodium salt (Owczarzy et al., *Biochemistry* 2004, 43:3537-3554). The coefficients optimized for Equation 13 are summarized in Table IIIa.

TABLE IIIa

Determined Coefficient Values for Equation 13, for $T_m^o$ obtained at 1M cation concentration.

| Coefficient | Value (K$^{-1}$) | Standard error (K$^{-1}$) | Relative error (%) |
|---|---|---|---|
| a | 3.92 × 10$^{-5}$ | 0.2 × 10$^{-5}$ | 5.1 |
| b | −9.11 × 10$^{-6}$ | 0.5 × 10$^{-6}$ | 5.5 |
| c | 6.26 × 10$^{-5}$ | 0.4 × 10$^{-5}$ | 6.4 |
| d | 1.42 × 10$^{-5}$ | 0.08 × 10$^{-5}$ | 5.6 |
| e | −4.82 × 10$^{-4}$ | 0.7 × 10$^{-4}$ | 14.5 |
| f | 5.25 × 10$^{-4}$ | 0.2 × 10$^{-4}$ | 3.8 |
| g | 8.31 × 10$^{-5}$ | 0.2 × 10$^{-5}$ | 2.4 |

Equation 16 describes the fit of $T_m$ and $T_m^o$ differences. The method required a separate optimization for the equation, which resulted in different coefficient values. The coefficients optimized for Equation 16 are summarized in Table IIIb.

TABLE IIIb

Determined Coefficient Values for Equation 16, for $T_m^o$ obtained at 1M cation concentration.

| Coefficient | Value (K) | Standard error (K) | Relative error (%) |
|---|---|---|---|
| a' | −4.59 | 0.3 | 6.5 |
| b' | 1.06 | 0.05 | 4.7 |
| c' | −7.26 | 0.4 | 5.5 |

TABLE IIIb-continued

Determined Coefficient Values for Equation 16, for
$T_m°$ obtained at 1M cation concentration.

| Coefficient | Value (K) | Standard error (K) | Relative error (%) |
|---|---|---|---|
| d' | −1.34 | 0.08 | 6.0 |
| e' | 63.3 | 6 | 9.5 |
| f' | −60.4 | 2 | 3.3 |
| g' | −8.78 | 0.2 | 2.3 |

Estimated Errors. Two methods were used to estimate standard errors of coefficients. The errors were obtained from residuals of the multiple linear regression fit and from bootstrap simulations (see Efron, B., Tibshirani, R. J., 1993, *An Introduction to the Bootstrap*. Chapman & Hall/CRC, Boca Raton, Fla.). The experimental dataset consisted of 680 $T_m$ values for 92 unique duplex DNAs that are shown in Table I and II. Ten thousand bootstrap sample datasets were generated from the experimental dataset. Each bootstrap dataset was of the same size (680 $T_m$'s) and was constructed by random drawing of $T_m$ values, with replacement, from the original experimental dataset. Entire experimental dataset was used in each drawing. Coefficients of Equations 13 (a, b, c, d, e, f, g) and 16 (a', b', c', d', e', f', g') were obtained from each bootstrap dataset using a multivariate linear regression fit. The fits were calculated for each dataset using Excel LINEST function. Bootstrap simulations were run in Microsoft Excel 2003 environment. The procedure generated ten thousand bootstrap estimates of coefficients (a, b, c, d, e, f, g) and (a', b', c', d', e', f', g'). Bootstrap estimates of standard errors for each coefficient were calculated from these estimates of coefficients. The errors are presented in the third column of Table IIIa and Table IIIb. Extra significant figures of the coefficients are reported to prevent rounding errors when coefficient are used. Addition of higher order terms, e.g., $(\ln [Mg^{2+}])^3$, $(\ln [Mg^{2+}])^4$, in Equations 13 and 16, and re-optimization of the coefficients could give additional useful and functional $T_m$ magnesium corrections.

Example 3

Melting Temperatures Predicted by Equation 13 Compared to Experimentally Determined Melting Temperatures in Buffers where Monovalent Ions do not Compete with Divalent ($Mg^+$) Ions Starting from published $T_m$ (1M $Na^+$) values (Owczarzy et al., *Biochemistry* 2004, 43:3537-3554), melting temperatures for SEQ ID NOS: 1-92 were predicted from Equation 13 using the coefficients determined in Example 2.

Figure 3A:
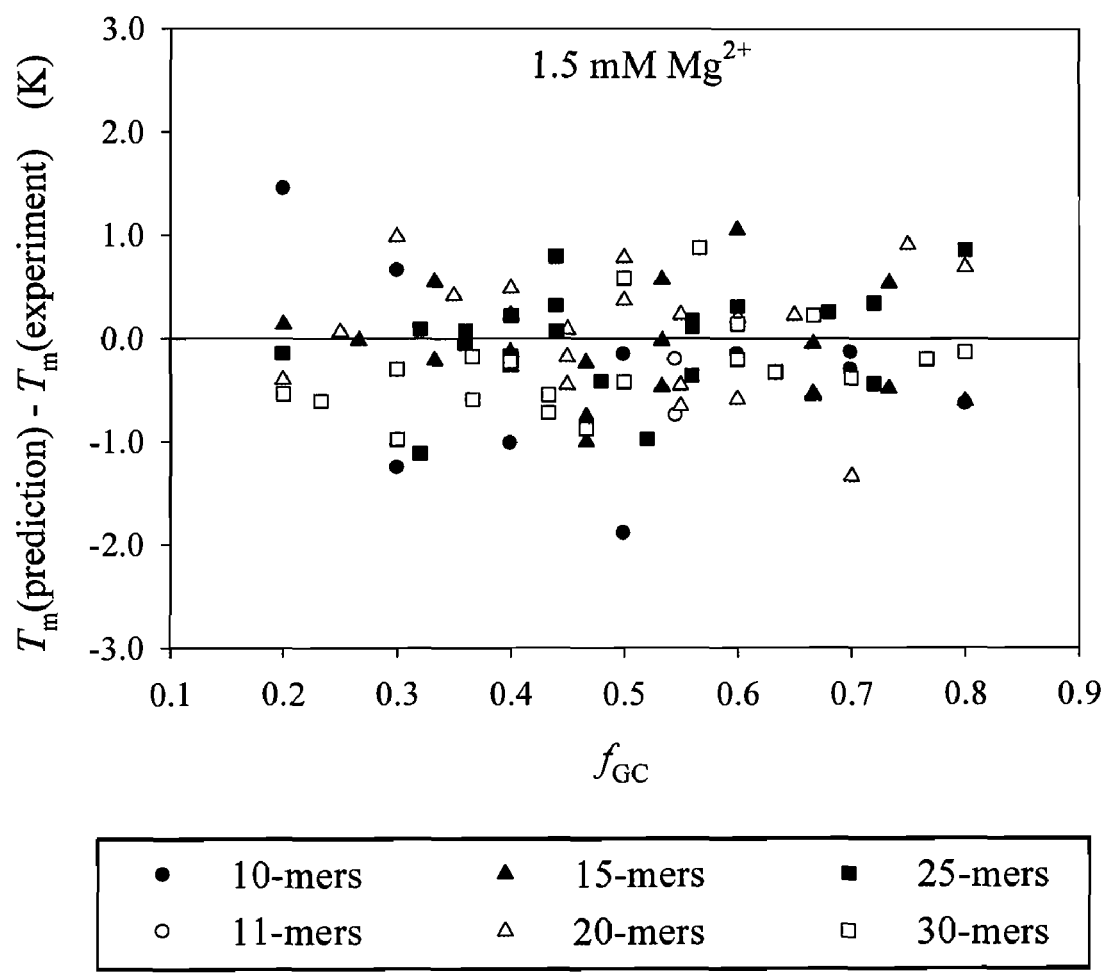
FIG. 3A is a graph showing errors of $T_m$ predictions for the oligonucleotides represented in Table I using Equation 13 in 1.5 mM Mg$^{2+}$ when no KCl is present. (●=10-mers; ○=11-mers; ▲=15-mers; ∆=20-mers; □=25-mers; ■=30-mers)
Figure 3B:
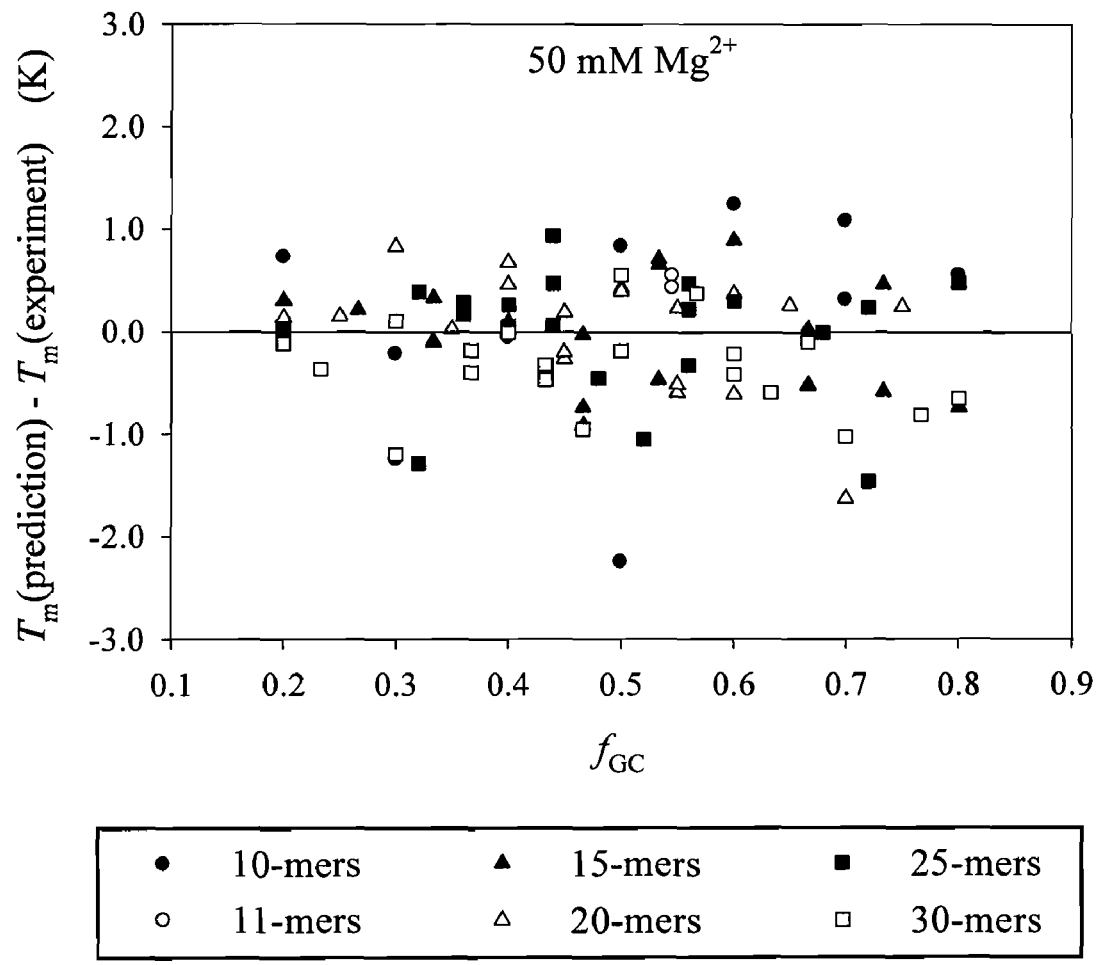
FIG. 3B is a graph showing errors of $T_m$ predictions for the oligonucleotides represented in Table I using Equation 13 in 50 mM Mg$^{2+}$ when no KCl is present. (●=10-mers; ○=11-mers; ▲=15-mers; ∆=20-mers; □=25-mers; ■=30-mers)
Figure 4:
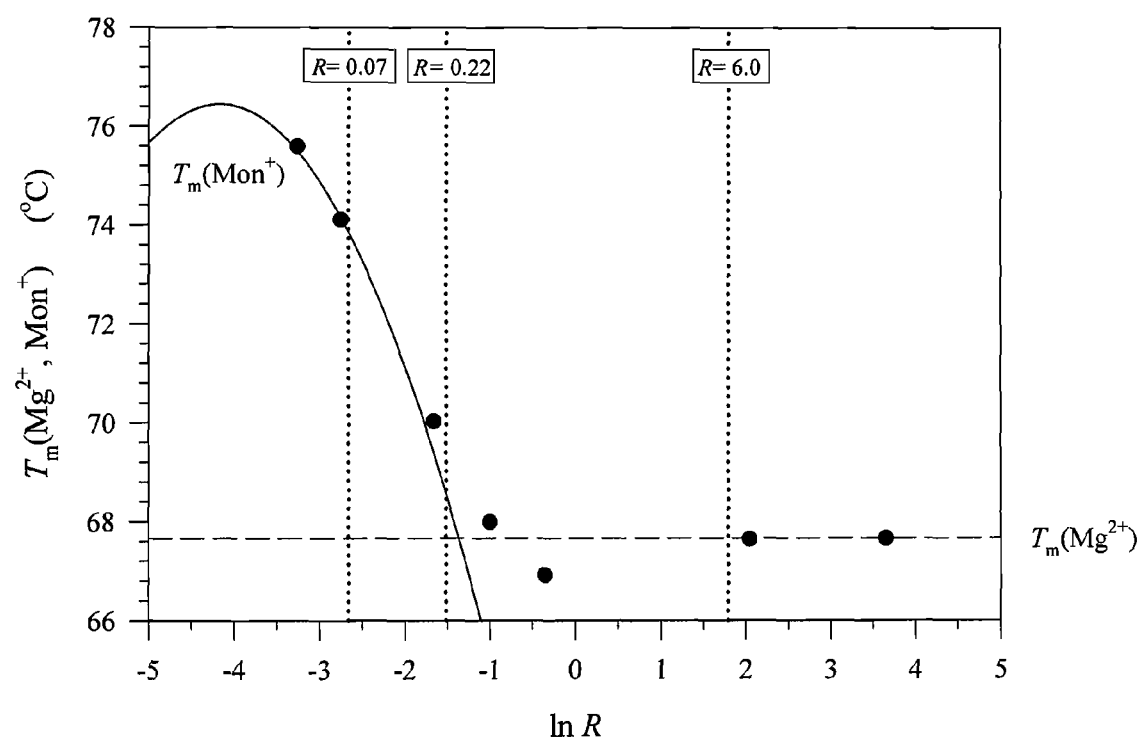
FIG. 4 shows the competitive effects of K$^+$ and Mg$^{2+}$ that were examined for the 25 bp long duplex, CTGGTCTG-GATCTGAGAACTTCAGG (SEQ ID NO: 52). Solid circles (●) are $T_m$'s plotted against ln R, where R=[Mg$^{2+}$]$^{0.5}$/[Mon$^+$]. Buffers are composed of constant 1.5 mM Mg$^{2+}$ while KCl concentration varies. The solid line shows melting temperatures predicted by sodium salt correction (Equation 3) when no Mg$^{2+}$ is present. The dashed line indicates $T_m$ in magnesium buffer when no KCl is present. The dominant ion crossover that occurs on average at R of 0.22 is indicated with the dotted vertical line.

Comparison of predicted $T_m$ with the experimental values of Example 1 reveals that melting temperatures were predicted with an average error of 0.5° C. Errors of $T_m$ predictions as a function of $N_{bp}$, $f_{GC}$, and magnesium concentration were examined. They are presented in Tables IVa and IVb, and in FIGS. 3A and 3B. No systematic error trends have been found. Predicted melting temperatures provided by the Equation 13 have similar accuracy for all sequences.

TABLE IVa

Errors of $T_m$ predictions, $T_m$ (prediction)-$T_m$ (experiment), for 92 DNA duplex oligomers from Table I. Melting temperatures were predicted from Equation 13 and experimentally measured $T_m°$ in 1M Na+.

| | | 2 mM Tris-HCl | | | | | 10 mM Tris-HCl | |
|---|---|---|---|---|---|---|---|---|
| SEQ ID NO: | Sequence (5' to 3') | Error to $T_m$ prediction (K) at $Mg^{2+}$ concentration indicated | | | | | | |
| | | 0.5 mM | 1.5 mM | 3 mM | 10 mM | 20 mM | 50 mM | 125 mM |
| 1 | TACTAACATTAACTA | 0.6 | 0.1 | 0.3 | −0.2 | 0.5 | 0.3 | −0.1 |
| 2 | ATACTTACTGATTAG | 0.6 | 0.0 | 0.2 | 0.5 | 0.3 | 0.2 | −0.2 |
| 3 | GTACACTGTCTTATA | 0.5 | −0.2 | 0.0 | 0.0 | 0.2 | −0.1 | −0.4 |
| 4 | GTATGAGAGACTTTA | 1.0 | 0.5 | 0.5 | 0.3 | 0.5 | 0.3 | −0.1 |
| 5 | TTCTACCTATGTGAT | −0.5 | −0.2 | −0.4 | −0.7 | −0.1 | −0.1 | −0.5 |
| 6 | AGTAGTAATCACACC | −0.2 | −0.1 | −0.1 | −0.2 | 0.1 | 0.1 | −0.4 |
| 7 | ATCGTCTCGGTATAA | −0.2 | −0.3 | −0.4 | −0.4 | −0.1 | 0.0 | −0.8 |
| 8 | ACGACAGGTTTACCA | −1.0 | −1.0 | −0.9 | −1.2 | −1.0 | −0.9 | −1.5 |
| 9 | CTTTCATGTCCGCAT | −0.8 | −0.2 | 0.0 | 0.0 | 0.1 | 0.0 | −0.3 |
| 10 | TGGATGTGTGAACAC | −0.2 | −0.8 | −0.6 | −0.6 | −0.5 | −0.7 | −1.2 |
| 11 | ACCCCGCAATACATG | −0.3 | 0.0 | 0.2 | 0.1 | 0.2 | 0.7 | 0.1 |
| 12 | GCAGTGGATGTGAGA | 0.5 | 0.6 | 0.7 | 0.9 | 0.9 | 0.7 | 0.7 |
| 13 | GGTCCTTACTTGGTG | −0.4 | −0.5 | −0.5 | −0.5 | −0.5 | −0.5 | −0.7 |
| 14 | CGCCTCATGCTCATC | 1.1 | 1.0 | 1.0 | 1.2 | 1.3 | 0.9 | 0.8 |
| 15 | AAATAGCCGGGCCGC | −0.3 | −0.6 | −0.3 | −0.3 | 0.0 | −0.5 | −1.0 |

TABLE IVa-continued

Errors of $T_m$ predictions, $T_m$ (prediction)-$T_m$ (experiment), for 92 DNA duplex oligomers from Table I. Melting temperatures were predicted from Equation 13 and experimentally measured $T_m$ ° in 1M Na+.

| SEQ ID NO: | Sequence (5' to 3') | 2 mM Tris-HCl | | | | | 10 mM Tris-HCl | |
|---|---|---|---|---|---|---|---|---|
| | | Error to $T_m$ prediction (K) at $Mg^{2+}$ concentration indicated | | | | | | |
| | | 0.5 mM | 1.5 mM | 3 mM | 10 mM | 20 mM | 50 mM | 125 mM |
| 16 | CCAGCCAGTCTCTCC | 0.0 | −0.1 | 0.2 | 0.2 | 0.3 | 0.0 | −0.5 |
| 17 | GACGACAAGACCGCG | −1.0 | −0.5 | −0.3 | 0.0 | 0.1 | −0.5 | −0.6 |
| 18 | CAGCCTCGTCGCAGC | 0.1 | 0.5 | 0.7 | 0.7 | 0.6 | 0.5 | 0.1 |
| 19 | CTCGCGGTCGAAGCG | −0.6 | −0.5 | −0.4 | 0.0 | −0.2 | −0.6 | −0.6 |
| 20 | GCGTCGGTCCGGGCT | −0.9 | −0.6 | −0.4 | 0.0 | −0.4 | −0.7 | −1.0 |
| 21 | TATGTATATTTTGTAATCAG | −0.3 | −0.4 | −0.2 | −0.1 | 0.1 | 0.1 | 0.0 |
| 22 | TTCAAGTTAAACATTCTATC | 0.1 | 0.1 | 0.1 | 0.3 | 0.2 | 0.2 | −0.2 |
| 23 | TGATTCTACCTATGTGATTT | 1.2 | 1.0 | 1.1 | 1.1 | 1.2 | 0.8 | 0.8 |
| 24 | GAGATTGTTTCCCTTTCAAA | 0.9 | 0.4 | 0.4 | 0.4 | 0.2 | 0.0 | −0.2 |
| 25 | ATGCAATGCTACATATTCGC | 0.3 | 0.2 | 0.5 | 0.6 | 0.7 | 0.5 | 0.6 |
| 26 | CCACTATACCATCTATGTAC | 0.5 | 0.5 | 0.5 | 0.7 | 0.7 | 0.7 | 0.5 |
| 27 | CCATCATTGTGTCTACCTCA | −0.5 | −0.4 | −0.3 | −0.1 | −0.1 | −0.3 | −0.3 |
| 28 | CGGGACCAACTAAAGGAAAT | 0.0 | −0.2 | −0.3 | −0.1 | −0.1 | −0.2 | −0.7 |
| 29 | TAGTGGCGATTAGATTCTGC | 0.1 | 0.1 | 0.2 | 0.5 | 0.4 | 0.2 | 0.0 |
| 30 | AGCTGCAGTGGATGTGAGAA | 1.0 | 0.8 | 0.8 | 0.9 | 0.9 | 0.4 | 0.7 |
| 31 | TACTTCCAGTGCTCAGCGTA | 0.5 | 0.4 | 0.4 | 0.5 | 0.6 | 0.4 | 0.2 |
| 32 | CAGTGAGACAGCAATGGTCG | 0.4 | 0.2 | 0.2 | 0.4 | 0.4 | 0.2 | 0.2 |
| 33 | CGAGCTTATCCCTATCCCTC | −0.2 | −0.5 | −0.4 | −0.4 | −0.4 | −0.6 | −0.7 |
| 34 | CGTACTAGCGTTGGTCATGG | −0.6 | −0.7 | −0.5 | −0.5 | −0.4 | −0.5 | −0.6 |
| 35 | AAGGCGAGTCAGGCTCAGTG | −0.5 | −0.6 | −0.8 | −0.3 | −0.4 | −0.6 | −0.7 |
| 36 | ACCGACGACGCTGATCCGAT | 0.4 | 0.2 | 0.5 | 0.3 | 0.8 | 0.4 | 0.5 |
| 37 | AGCAGTCCGCCACACCCTGA | 0.4 | 0.2 | 0.6 | 0.4 | 0.4 | 0.3 | 0.3 |
| 38 | CAGCCTCGTTCGCACAGCCC | −1.0 | −1.3 | −1.3 | −1.3 | −1.4 | −1.6 | −1.7 |
| 39 | GTGGTGGGCCGTGCGCTCTG | 1.1 | 0.9 | 0.7 | 0.6 | 0.6 | 0.3 | 0.3 |
| 40 | GTCCACGCCCGGTGCGACGG | 0.9 | 0.7 | 0.2 | 1.0 | 0.8 | 0.5 | 0.3 |
| 41 | GATATAGCAAAATTCTAAGTTAATA | 0.1 | −0.1 | 0.0 | 0.0 | −0.4 | 0.0 | −0.1 |
| 42 | ATAACTTTACGTGTGTGACCTATTA | 0.4 | 0.1 | 0.2 | 0.3 | 0.5 | 0.4 | 0.4 |
| 43 | GTTCTATACTCTTGAAGTTGATTAC | −0.9 | −1.1 | −1.1 | −1.2 | −1.1 | −1.3 | −1.2 |
| 44 | CCCTGCACTTTAACTGAATTGTTTA | 0.4 | 0.1 | 0.2 | 0.3 | 0.5 | 0.3 | 0.2 |
| 45 | TAACCATACTGAATACCTTTTGACG | 0.2 | 0.0 | 0.1 | 0.2 | 0.2 | 0.2 | 0.2 |
| 46 | TCCACACGGTAGTAAAATTAGGCTT | 0.0 | −0.2 | 0.0 | 0.1 | −0.4 | 0.1 | 0.1 |
| 47 | TTCCAAAAGGAGTTATGAGTTGCGA | 0.3 | 0.2 | 0.2 | 0.3 | 0.4 | 0.3 | 0.3 |
| 48 | AATATCTCTCATGCGCCAAGCTACA | 0.7 | 0.3 | 0.5 | 0.6 | 0.8 | 0.5 | 0.7 |

TABLE IVa-continued

Errors of $T_m$ predictions, $T_m$ (prediction)-$T_m$ (experiment), for 92 DNA duplex oligomers from Table I. Melting temperatures were predicted from Equation 13 and experimentally measured $T_m$ ° in 1M Na+.

| SEQ ID NO: | Sequence (5' to 3') | 2 mM Tris-HCl | | | | | 10 mM Tris-HCl | |
|---|---|---|---|---|---|---|---|---|
| | | Error to $T_m$ prediction (K) at $Mg^{2+}$ concentration indicated | | | | | | |
| | | 0.5 mM | 1.5 mM | 3 mM | 10 mM | 20 mM | 50 mM | 125 mM |
| 49 | TAGTATATCGCAGCATCATACAGGC | 0.9 | 0.8 | 0.8 | 0.4 | 1.0 | 0.9 | 1.0 |
| 50 | TGGATTCTACTCAACCTTAGTCTGG | 0.2 | 0.1 | 0.0 | 0.1 | 0.2 | 0.1 | 0.2 |
| 51 | CGGAATCCATGTTACTTCGGCTATC | -0.1 | -0.4 | -0.3 | -0.4 | -0.3 | -0.4 | -0.4 |
| 52 | CTGGTCTGGATCTGAGAACTTCAGG | -0.8 | -1.0 | -1.0 | -0.9 | -1.0 | -1.0 | -1.0 |
| 53 | ACAGCGAATGGACCTACGTGGCCTT | 0.2 | 0.1 | 0.1 | 0.2 | 0.4 | 0.5 | 0.5 |
| 54 | AGCAAGTCGAGCAGGGCCTACGTTT | 0.3 | 0.2 | 0.1 | 0.4 | 0.2 | 0.2 | 0.1 |
| 55 | GCGAGCGACAGGTTACTTGGCTGAT | -0.2 | -0.4 | -0.4 | -0.2 | -0.3 | -0.3 | -0.2 |
| 56 | AAAGGTGTCGCGGAGAGTCGTGCTG | 0.7 | 0.3 | 0.4 | 0.3 | 0.2 | 0.3 | 0.4 |
| 57 | ATGGGTGGGAGCCTCGGTAGCAGCC | 0.8 | 0.3 | 0.3 | 0.1 | 0.1 | 0.0 | -0.2 |
| 58 | CAGTGGGCTCCTGGGCGTGCTGGTC | -0.2 | -0.4 | -0.5 | -0.8 | -0.8 | -1.5 | -1.0 |
| 59 | GCCAACTCCGTCGCCGTTCGTGCGC | 0.6 | 0.3 | 0.3 | 0.5 | 0.4 | 0.2 | 0.0 |
| 60 | ACGGGTCCCCGCACCGCACCGCCAG | 1.0 | 0.9 | 0.8 | 1.0 | 0.9 | 0.5 | 0.4 |
| 61 | TTATGTATTAAGTTATATAGTAGTAGTAGT | -0.1 | -0.5 | -0.4 | -0.3 | -0.1 | -0.1 | -0.1 |
| 62 | ATTGATATCCTTTTCTATTCATCTTTCATT | -0.2 | -0.6 | -0.6 | -0.5 | -0.3 | -0.4 | -0.4 |
| 63 | AAAGTACATCAACATAGAGAATTGCATTTC | 0.0 | -0.3 | -0.2 | 0.1 | 0.1 | 0.1 | 0.0 |
| 64 | CTTAAGATATGAGAACTTCAACTAATGTGT | -0.8 | -1.0 | -0.9 | -0.8 | -0.7 | -1.2 | -0.9 |
| 65 | CTCAACTTGCGGTAAATAAATCGCTTAATC | 0.0 | -0.2 | -0.2 | 0.0 | 0.1 | -0.2 | -0.1 |
| 66 | TATTGAGAACAAGTGTCCGATTAGCAGAAA | -0.4 | -0.6 | -0.6 | -0.4 | -0.3 | -0.4 | -0.3 |
| 67 | GTCATACGACTGAGTGCAACATTGTTCAAA | 0.1 | -0.2 | -0.1 | -0.1 | 0.1 | 0.0 | 0.0 |
| 68 | AACCTGCAACATGGAGTTTTTGTCTCATGC | -0.5 | -0.7 | -0.7 | -0.3 | -0.4 | -0.5 | -0.4 |
| 69 | CCGTGCGGTGTGTACGTTTTATTCATCATA | -0.3 | -0.5 | -0.4 | -0.4 | -0.4 | -0.3 | -0.1 |
| 70 | GTTCACGTCCGAAAGCTCGAAAAAGGATAC | -0.5 | -0.9 | -0.9 | -0.7 | -0.8 | -1.0 | -1.1 |
| 71 | AGTCTGGTCTGGATCTGAGAACTTCAGGCT | -0.3 | -0.4 | -0.4 | -0.4 | -0.3 | -0.2 | -0.4 |
| 72 | TCGGAGAAATCACTGAGCTGCCTGAGAAGA | 0.9 | 0.6 | 0.5 | 0.7 | 0.7 | 0.6 | 0.6 |
| 73 | CTTCAACGGATCAGGTAGGACTGTGGTGGG | 1.1 | 0.9 | 0.7 | 0.7 | 0.6 | 0.4 | 0.3 |
| 74 | ACGCCCACAGGATTAGGCTGGCCCACATTG | 0.0 | -0.2 | -0.3 | -0.2 | -0.1 | -0.4 | -0.3 |
| 75 | GTTATTCCGCAGTCCGATGGCAGCAGGCTC | 0.5 | 0.1 | 0.2 | 0.0 | 0.0 | -0.2 | 0.0 |
| 76 | TCAGTAGGCGTGACGCAGAGCTGGCGATGG | 0.3 | -0.3 | 0.2 | 0.1 | -0.4 | -0.6 | -0.5 |
| 77 | CGCGCCACGTGTGATCTACAGCCGTTCGGC | 0.2 | 0.2 | 0.2 | 0.0 | 0.3 | -0.1 | 0.1 |
| 78 | GACCTGACGTGGACCGCTCCTGGGCGTGGT | -0.1 | -0.4 | -0.5 | -0.6 | -0.7 | -1.0 | -1.1 |
| 79 | GCCCCTCCACTGGCCGACGGCAGCAGGCTC | 0.1 | -0.2 | -0.4 | -0.3 | -0.6 | -0.8 | -0.9 |
| 80 | CGCCGCTGCCGACTGGAGGAGCGCGGGACG | 0.0 | -0.1 | -0.4 | 0.0 | -0.5 | -0.7 | -0.7 |
| 81 | ATCAATCATA | 0.9 | 1.4 | 1.7 | 2.1 | 2.2 | 0.7 | 0.7 |
| 82 | TTGTAGTCAT | -1.6 | -1.3 | -0.6 | -0.5 | -0.6 | -1.2 | -1.5 |

TABLE IVa-continued

Errors of $T_m$ predictions, $T_m$ (prediction)-$T_m$ (experiment), for 92 DNA duplex oligomers from Table I. Melting temperatures were predicted from Equation 13 and experimentally measured $T_m°$ in 1M Na+.

| | | 2 mM Tris-HCl | | | | | 10 mM Tris-HCl | |
|---|---|---|---|---|---|---|---|---|
| | | Error to $T_m$ prediction (K) at $Mg^{2+}$ concentration indicated | | | | | | |
| SEQ ID NO: | Sequence (5' to 3') | 0.5 mM | 1.5 mM | 3 mM | 10 mM | 20 mM | 50 mM | 125 mM |
| 83 | GAAATGAAAG | -0.5 | 0.7 | -0.4 | 1.4 | -0.1 | -0.2 | -1.0 |
| 84 | CCAACTTCTT | 0.1 | -1.0 | -0.2 | -0.4 | 0.1 | -0.1 | -0.1 |
| 85 | ATCGTCTGGA | -0.4 | -0.2 | 0.2 | -0.6 | 0.7 | 0.8 | -0.2 |
| 86 | AGCGTAAGTC | 0.7 | -1.9 | -1.3 | -0.7 | -1.3 | -2.2 | -2.9 |
| 87 | CGATCTGCGA | 0.7 | -0.2 | 1.1 | -0.2 | 0.6 | 1.2 | 0.5 |
| 88 | TGGCGAGCAC | 0.2 | -0.3 | 0.7 | 0.8 | 1.0 | 0.3 | -0.6 |
| 89 | GATGCGCTCG | -0.4 | -0.1 | 0.7 | 1.1 | 1.2 | 1.1 | 0.1 |
| 90 | GGGACCGCCT | -0.9 | -0.6 | -0.6 | -0.1 | 0.0 | 0.6 | -0.9 |
| 91 | CGTACACATGC | -0.4 | -0.7 | -0.4 | -0.5 | 0.3 | 0.5 | -0.3 |
| 92 | CCATTGCTACC | 0.0 | -0.2 | 0.1 | 0.2 | 0.3 | 0.4 | -0.3 |

TABLE IVb

Errors of $T_m$ predictions, $T_m$ (prediction)-$T_m$ (experiment), for DNA duplex oligomers from Table II. Melting temperatures were predicted from Equation 13 and experimentally measured $T_m°$ in 1M Na+.

| | | 10 mM Tris-HCl Error of $T_m$ prediction (K) at $Mg^{2+}$ concentration indicated | |
|---|---|---|---|
| SEQ ID NO: | Sequence (5' to 3') | 300 mM | 600 mM |
| 5 | TTCTACCTATGTGAT | -0.2 | 0.4 |
| 12 | GCAGTGGATGTGAGA | 0.8 | 1.9 |
| 18 | CAGCCTCGTCGCAGC | 0.8 | 1.5 |
| 23 | TGATTCTACCTATGTGATTT | 1.3 | 2.1 |
| 30 | AGCTGCAGTGGATGTGAGAA | 1.3 | 2.2 |
| 38 | CAGCCTCGTTCGCACAGCCC | -0.9 | 0.2 |
| 43 | GTTCTATACTCTTGAAGTTGATTAC | -0.9 | -0.2 |
| 52 | CTGGTCTGGATCTGAGAACTTCAGG | -0.6 | 0.2 |
| 58 | CAGTGGGCTCCTGGGCGTGCTGGTC | -0.2 | 1.0 |
| 64 | CTTAAGATATGAGAACTTCAACTAATGTGT | 0.1 | 0.9 |
| 71 | AGTCTGGTCTGGATCTGAGAACTTCAGGCT | 0.3 | 1.2 |
| 78 | GACCTGACGTGGACCGCTCCTGGGCGTGGT | 0.1 | 1.1 |
| 82 | TTGTAGTCAT | -1.9 | -1.3 |
| 85 | ATCGTCTGGA | 0.1 | 0.3 |
| 89 | GATGCGCTCG | 0.7 | 1.4 |
| 90 | GGGACCGCCT | -1.3 | -0.3 |
| 91 | CGTACACATGC | 0.3 | 1.1 |
| 92 | CCATTGCTACC | -0.7 | 0.2 |

Example 4

Comparison of $T_m$ Determined by Equations 13 and 16 against Previously Published Equations The accuracy of $T_m$ predictions for Equations 13, 16, and the four following magnesium corrections reported in the published literature were studied by comparison of $T_m$ predictions for the data of Tables I and II. The four published equations include:

$$T_m(Mg^{2+}) = T_m(1M\ Na^+) + 16.6 \times \log\left(\frac{4 \times \sqrt{[Mg^{2+}]} +}{[Mon^+]}\right) \quad \text{(Equation 6)}$$

(Mitsuhashi, *J. Clin. Lab. Analysis*, 1996, 10:277-284)

$$\frac{1}{T_m(Mg^{2+})} = \quad \text{(Equation 7)}$$

$$\frac{1}{T_m(1\ M\ Na^+)} + \frac{0.368\ N}{\Delta H^\circ} \times \ln\left(3.79 \times \sqrt{[Mg^{2+}]} + [Mon^+]\right)$$

(von Ahsen et al., *Clin. Chem.* 2001, 47:1956-1961)

$$\frac{1}{T_m(Mg^{2+})} = \quad \text{(Equation 8)}$$

$$\frac{1}{T_m(1M\ Na^+)} + \frac{0.368N}{\Delta H^0} \times \ln\left(\frac{3.3 \times \sqrt{[Mg^{2+}]} +}{[Mon^+]}\right)$$

(Peyret, Ph.D. Thesis, Wayne State University, Detroit, Mich., pp. 128, section 5.4.2 (2000))

$$\frac{1}{T_m(Mg^{2+})} = \frac{1}{T_m(1\ M\ Na^+)} - \frac{0.00322 \times \Delta g_{el} \times (N_{bp}-1)}{\Delta H^\circ} \quad \text{(Equation 9)}$$

(Tan and Chen, *Biophys. J.* 2006, 90:1175-1190).

Because the solution was buffered at a pH of 8.3, the monovalent concentration was assumed to be equal to half of the total Tris concentration in these calculations (1 mM monovalent ion for the 0.5-20 mM magnesium solutions and 5 mM for the 50-600 mM magnesium solutions). This is because the functional group primarily involved in the buffering action of Tris is an —NH$_2$ group that ionizes to —NH$_3^+$ at a pK$_a$ of 8.3, and the pK$_a$ is the pH at which 50% of the buffer concentration is ionized and 50% is not.

Statistical comparisons of experimental results with predictions from Equations 6-9 and Equations 13 and 16 are summarized in the Table V. As before, each analysis used a reference salt concentration $[Na^+]_0 = 1.0$ M. The reference melting temperature, $T_m^0$ was the oligomer's experimentally determined melting temperature, previously published in Owczarzy et al., *Biochemistry* 2004, 43:35367-3554. Goodness of fit was evaluated from the reduced "chi-square" value ($\chi_r^2 = \chi^2/\nu$) and from $<|\Delta T_m|>_{AVE}$, the average difference between the measured $T_m$ values and corresponding $T_m$ values predicted using Equations 6-9 and Equations 13 and 16 for scaling of $T_m$ from 1 M Na$^+$ buffer to Mg$^{2+}$ buffers. The R ratios were larger than 6.0 in all experiments reported in Table I and Table II, that is, magnesium ions were dominant. The chi-squared goodness-of-fit test compares a theoretical distribution with the observed data from a sample. (See William H. Press et al., *Numerical Recipes in C. The Art of Scientific Computing* 659-61 (2d Ed. 1992)). Thus, smaller values for $\chi_r^2$ and/or $<|\Delta T_m|>_{AVE}$ indicate that the equation or model used accurately and reliably predicts actual melting temperatures for different salt concentrations. $\nu$ is the number of degrees of freedom in the fit. Statistical F-tests were applied to compare $\chi_r^2$ differences between each $T_m$ magnesium correction. The tests provided probability P (compared to Equation 13) that observed differences in values of $\chi_r^2$ can happen by random chance alone.

Equation 13 predicts $T_m$ values from Table I and Table II with the highest accuracy and with the average error of 0.5° C. The P values show that Equation 13 provides significantly more accurate $T_m$ predictions than the Equations 6, 7, 8 and 9. Without being limited to any particular theory or mechanism of action, it is believed that Equations 6-9 are less accurate because the assumption of equivalent effects for Na$^+$ and Mg$^{2+}$ ions does not hold. It was discovered that the effects of magnesium ions on $T_m$ differ significantly both quantitatively and qualitatively from effects of sodium ions as discussed above. The changes of $T_m$ caused by magnesium ions depend both on the number of base pairs Nbp as well as the fraction of G-C base pairs $f_{GC}$. In contrast, $T_m$ changes brought about by sodium ions are independent of the number of base pairs and depend mainly on the fraction of G-C base pairs (Owczarzy et al., *Biochemistry* 2004, 43:3537-3554). Therefore, the $T_m$ magnesium correction function contains extra terms and is different from the $T_m$ sodium correction function. Equations 6-9 in the prior art take no account of the effect of the G-C base pair content on the influence of monovalent and divalent cations on duplex stability and hence Tm.

TABLE V

Statistical analysis of $T_m$ predictions for data of Table I and Table II at "dominant" divalent ion concentrations, in Tris-HCl, no KCl, and [DNA] = 2 µM.

| Equation | Magnesium $T_m$ correction | $<|\Delta T_m|>_{AVE}$ (° C.) | $\chi^2/\nu$ | P |
|---|---|---|---|---|
| 13 | This invention ($1/T_m$ correction function) | 0.5 | 4.6 | |
| 16 | This invention ($T_m$ correction function) | 0.5 | 5.0 | 0.266 |
| 8 | Peyret correction | 2.9 | 163.1 | <10$^{-300}$ |
| 7 | Ahsen et al. correction | 3.0 | 185.3 | <10$^{-300}$ |
| 9 | Tan and Chen correction | 3.2 | 171.5 | <10$^{-300}$ |
| 6 | Mitsuhashi correction | 4.7 | 350.7 | <10$^{-300}$ |

The data presented in Table IV and Table V, supra, shows that the Equations 13 and 16, predict the melting temperature of a particular polynucleotide with greater accuracy and reliability than existing methods (P<0.05). Equation 16 provided slightly less accurate $T_m$ predictions, however, the difference between equation 13 and equation 16 is not statistically significant (P=0.27).

Example 5

Selection of the Most Accurate $T_m$ Correction Function and Calculation of Coefficients in Buffers where Divalent Ions (Mg$^+$) Compete with Monovalent Ions (K$^+$)

DNA oligomers were prepared using a published procedure (Moreira et al., *Biochem. Biophys. Res. Commun.* 2005, 327:473-484 and Owczarzy et al., *Biochemistry* 2004, 43:3537-3554), as outlined in Example 1. In this Example 5, both monovalent ions (K$^+$, Tris$^+$) and divalent ions (Mg$^+$) were present in significant concentrations and competed for their effects on melting temperatures. Therefore, the algorithm outlined in FIG. 5 was used to select the most accurate $T_m$ salt correction based on concentrations of magnesium and monovalent ions. When ratios R were in the range from 0.22 to 6.0, coefficients a, d, g, in Equation 13 were allowed to vary with monovalent ion concentrations according to Equations 18, 19 and 20. In the first set of experiments, the concentration of potassium ions was 50 mM KCl, which is a typical concentration of KCl in PCR buffers. In the second set of experiments, 12 oligonucleotides were melted in 38 different magnesium buffers where magnesium concentrations were 0.5 mM, 1.5 mM, 3.0 mM, 10 mM, 20 mM, 50 mM or 125 mM and KCl concentrations were 0 mM, 50 mM, 100 mM, 200 mM, 600 mM or 1M. As stated in Example 1, buffers contained 10 mM Tris-HCl adjusted to pH 8.3 (at 25° C.) with 0.6 M HCl. Accuracy of $T_m$ predictions was estimated for both sets of experiments. DNA concentrations were 2 μM. Experimental results are shown in Tables VI and VII.

TABLE VI

Experimental melting temperatures of 80 DNA duplex oligomers in buffers containing 50 mM KCl and various magnesium concentrations.

| SEQ ID NO: | DNA sequence (5' to 3') | $T_m$ (° C.) at 50 mM KCl, 10 mM Tris-HCl and [Mg$^{2+}$] indicated | | | | |
|---|---|---|---|---|---|---|
| | | 0.5 mM | 1.5 mM | 3.0 mM | 10 mM | 20 mM |
| 1 | TACTAACATTAACTA | 38.1 | 40.8 | 42.6 | 46.3 | 47.4 |
| 2 | ATACTTACTGATTAG | 38.7 | 41.3 | 43.2 | 45.9 | 47.5 |
| 3 | GTACACTGTCTTATA | 42.8 | 45.3 | 47.1 | 49.9 | 51.0 |
| 4 | GTATGAGAGACTTTA | 42.1 | 45.1 | 47.1 | 50.2 | 51.4 |
| 6 | AGTAGTAATCACACC | 45.6 | 48.1 | 49.7 | 52.6 | 53.6 |
| 7 | ATCGTCTCGGTATAA | 47.3 | 49.8 | 51.4 | 54.2 | 55.1 |
| 8 | ACGACAGGTTTACCA | 50.3 | 53.1 | 54.6 | 57.8 | 58.5 |
| 9 | CTTTCATGTCCGCAT | 52.4 | 54.6 | 56.3 | 58.5 | 59.5 |
| 10 | TGGATGTGTGAACAC | 49.2 | 51.9 | 53.7 | 56.5 | 57.6 |
| 11 | ACCCCGCAATACATG | 52.8 | 55.0 | 56.2 | 58.5 | 59.2 |
| 13 | GGTCCTTACTTGGTG | 50.1 | 52.2 | 53.9 | 56.3 | 56.9 |
| 14 | CGCCTCATGCTCATC | 54.8 | 57.0 | 58.4 | 60.5 | 61.2 |
| 15 | AAATAGCCGGGCCGC | 61.0 | 63.5 | 64.5 | 66.3 | 67.0 |
| 16 | CCAGCCAGTCTCTCC | 56.5 | 58.9 | 60.3 | 62.3 | 63.1 |
| 17 | GACGACAAGACCGCG | 59.6 | 61.4 | 62.7 | 64.4 | 65.1 |
| 19 | CTCGCGGTCGAAGCG | 62.0 | 64.3 | 65.2 | 66.8 | 67.4 |
| 20 | GCGTCGGTCCGGGCT | 66.0 | 68.2 | 68.9 | 70.3 | 70.5 |
| 21 | TATGTATATTTGTAATCAG | 46.7 | 49.5 | 51.4 | 54.0 | 55.2 |
| 22 | TTCAAGTTAAACATTCTATC | 48.1 | 50.8 | 52.8 | 55.4 | 56.5 |
| 24 | GAGATTGTTTCCCTTTCAAA | 51.3 | 54.2 | 56.3 | 59.3 | 60.3 |
| 25 | ATGCAATGCTACATATTCGC | 56.9 | 59.3 | 60.7 | 62.8 | 63.6 |
| 26 | CCACTATACCATCTATGTAC | 52.9 | 55.0 | 56.4 | 58.3 | 59.1 |
| 27 | CCATCATTGTGTCTACCTCA | 57.5 | 60.1 | 61.2 | 63.0 | 64.0 |
| 28 | CGGGACCAACTAAAGGAAAT | 56.3 | 59.5 | 60.8 | 63.2 | 64.1 |
| 29 | TAGTGGCGATTAGATTCTGC | 59.4 | 61.8 | 63.1 | 65.1 | 66.1 |
| 31 | TACTTCCAGTGCTCAGCGTA | 62.2 | 64.6 | 65.6 | 67.4 | 68.2 |
| 32 | CAGTGAGACAGCAATGGTCG | 61.5 | 63.9 | 64.9 | 66.8 | 67.4 |
| 33 | CGAGCTTATCCCTATCCCTC | 58.9 | 61.9 | 63.4 | 65.2 | 65.9 |
| 34 | CGTACTAGCGTTGGTCATGG | 61.2 | 63.4 | 64.6 | 66.1 | 66.9 |
| 35 | AAGGCGAGTCAGGCTCAGTG | 66.1 | 68.3 | 69.5 | 71.0 | 71.5 |
| 36 | ACCGACGACGCTGATCCGAT | 67.3 | 69.3 | 70.1 | 71.9 | 72.3 |
| 37 | AGCAGTCCGCCACACCCTGA | 68.3 | 70.3 | 71.2 | 72.7 | 73.1 |

TABLE VI-continued

Experimental melting temperatures of 80 DNA duplex oligomers in buffers containing 50 mM KCl and various magnesium concentrations.

| SEQ ID NO: DNA sequence (5' to 3') | $T_m$ (° C.) at 50 mM KCl, 10 mM Tris-HCl and [Mg$^{2+}$] indicated | | | | |
|---|---|---|---|---|---|
| | 0.5 mM | 1.5 mM | 3.0 mM | 10 mM | 20 mM |
| 39 GTGGTGGGCCGTGCGCTCTG | 70.9 | 72.6 | 73.8 | 75.2 | 75.7 |
| 40 GTCCACGCCCGGTGCGACGG | 71.7 | 73.3 | 74.5 | 75.1 | 75.3 |
| 41 GATATAGCAAAATTCTAAGTTAATA | 51.9 | 54.7 | 56.8 | 59.5 | 60.6 |
| 42 ATAACTTTACGTGTGTGACCTATTA | 58.9 | 61.4 | 62.8 | 65.1 | 66.1 |
| 44 CCCTGCACTTTAACTGAATTGTTTA | 59.4 | 61.9 | 63.5 | 65.7 | 66.6 |
| 45 TAACCATACTGAATACCTTTTGACG | 58.6 | 61.0 | 62.7 | 65.3 | 65.6 |
| 46 TCCACACGGTAGTAAAATTAGGCTT | 61.3 | 64.0 | 65.4 | 67.3 | 68.2 |
| 47 TTCCAAAAGGAGTTATGAGTTGCGA | 61.2 | 63.7 | 65.2 | 67.2 | 68.0 |
| 48 AATATCTCTCATGCGCCAAGCTACA | 64.0 | 66.4 | 67.7 | 70.2 | 70.2 |
| 49 TAGTATATCGCAGCATCATACAGGC | 62.7 | 64.9 | 66.4 | 67.7 | 68.4 |
| 50 TGGATTCTACTCAACCTTAGTCTGG | 61.2 | 63.8 | 65.3 | 67.2 | 68.0 |
| 51 CGGAATCCATGTTACTTCGGCTATC | 63.2 | 65.5 | 67.1 | 69.0 | 69.6 |
| 53 ACAGCGAATGGACCTACGTGGCCTT | 70.2 | 72.0 | 73.2 | 75.3 | 75.2 |
| 54 AGCAAGTCGAGCAGGGCCTACGTTT | 70.5 | 72.5 | 73.4 | 74.6 | 75.3 |
| 55 GCGAGCGACAGGTTACTTGGCTGAT | 69.2 | 71.2 | 72.5 | 74.0 | 74.6 |
| 56 AAAGGTGTCGCGGAGAGTCGTGCTG | 71.1 | 73.2 | 74.3 | 75.6 | 76.2 |
| 57 ATGGGTGGGAGCCTCGGTAGCAGCC | 72.8 | 74.7 | 75.8 | 76.9 | 77.6 |
| 59 GCCAACTCCGTCGCCGTTCGTGCGC | 74.3 | 76.2 | 76.8 | 77.5 | 78.0 |
| 60 ACGGGTCCCCGCACCGCACCGCCAG | 78.4 | 80.8 | 80.8 | 81.5 | 81.5 |
| 61 TTATGTATTAAGTTATATAGTAGTAGTAGT | 53.1 | 55.8 | 57.7 | 60.4 | 61.1 |
| 62 ATTGATATCCTTTTCTATTCATCTTTCATT | 56.4 | 59.5 | 61.3 | 63.6 | 64.7 |
| 63 AAAGTACATCAACATAGAGAATTGCATTTC | 59.9 | 62.6 | 64.2 | 66.1 | 66.9 |
| 65 CTCAACTTGCGGTAAATAAATCGCTTAATC | 62.7 | 65.2 | 66.6 | 68.7 | 69.3 |
| 66 TATTGAGAACAAGTGTCCGATTAGCAGAAA | 63.7 | 66.4 | 67.9 | 70.0 | 70.6 |
| 67 GTCATACGACTGAGTGCAACATTGTTCAAA | 64.8 | 67.1 | 68.4 | 70.2 | 71.0 |
| 68 AACCTGCAACATGGAGTTTTTGTCTCATGC | 66.8 | 69.0 | 70.1 | 71.8 | 72.5 |
| 69 CCGTGCGGTGTGTACGTTTTATTCATCATA | 66.1 | 68.3 | 69.6 | 71.3 | 72.0 |
| 70 GTTCACGTCCGAAAGCTCGAAAAAGGATAC | 66.7 | 69.0 | 70.5 | 72.0 | 73.2 |
| 72 TCGGAGAAATCACTGAGCTGCCTGAGAAGA | 68.4 | 70.8 | 72.0 | 73.6 | 74.4 |
| 73 CTTCAACGGATCAGGTAGGACTGTGGTGGG | 69.3 | 71.6 | 72.4 | 73.6 | 74.4 |
| 74 ACGCCCACAGGATTAGGCTGGCCCACATTG | 73.2 | 75.3 | 76.5 | 77.2 | 77.8 |
| 75 GTTATTCCGCAGTCCGATGGCAGCAGGCTC | 72.7 | 74.7 | 76.0 | 77.1 | 77.7 |
| 76 TCAGTAGGCGTGACGCAGAGCTGGCGATGG | 74.6 | 76.3 | 77.2 | 78.3 | 78.4 |
| 77 CGCGCCACGTGTGATCTACAGCCGTTCGGC | 74.1 | 75.6 | 76.6 | 77.8 | 77.9 |
| 79 GCCCCTCCACTGGCCGACGGCAGCAGGCTC | 77.9 | 79.9 | 80.5 | 81.0 | 81.5 |
| 80 CGCCGCTGCCGACTGGAGGAGCGCGGGACG | 79.4 | 81.0 | 81.5 | 81.9 | 82.3 |

TABLE VI-continued

Experimental melting temperatures of 80 DNA duplex oligomers in buffers containing 50 mM KCl and various magnesium concentrations.

| SEQ ID NO: | DNA sequence (5' to 3') | $T_m$ (° C.) at 50 mM KCl, 10 mM Tris-HCl and [Mg$^{2+}$] indicated | | | | |
|---|---|---|---|---|---|---|
| | | 0.5 mM | 1.5 mM | 3.0 mM | 10 mM | 20 mM |
| 81 | ATCAATCATA | 22.4 | 24.3 | 25.9 | 29.5 | 30.4 |
| 82 | TTGTAGTCAT | 25.6 | 28.1 | 30.2 | 33.3 | 34.6 |
| 83 | GAAATGAAAG | 23.6 | 25.7 | 27.4 | 30.8 | 32.3 |
| 84 | CCAACTTCTT | 30.0 | 32.2 | 34.5 | 37.4 | 38.9 |
| 85 | ATCGTCTGGA | 35.5 | 37.8 | 39.2 | 41.8 | 43.2 |
| 86 | AGCGTAAGTC | 28.3 | 30.9 | 33.2 | 38.0 | 39.3 |
| 87 | CGATCTGCGA | 40.4 | 41.9 | 42.8 | 45.4 | 46.9 |
| 88 | TGGCGAGCAC | 45.6 | 47.8 | 49.2 | 52.4 | 52.8 |
| 89 | GATGCGCTCG | 44.8 | 46.7 | 47.9 | 50.4 | 50.9 |
| 90 | GGGACCGCCT | 49.1 | 50.9 | 52.6 | 55.1 | 56.0 |
| 91 | CGTACACATGC | 41.5 | 43.4 | 44.2 | 46.6 | 47.6 |
| 92 | CCATTGCTACC | 38.9 | 41.2 | 43.0 | 45.6 | 46.3 |

For Table VII, the [Mon$^+$] is the sum of the [Tris$^+$] and [K$^+$]. Solution contained either 0 mM, 50 mM, 100 mM, 200 mM, 600 mM or 1 M of KCl.

TABLE VII

Experimental melting temperatures (° C.) for 12 DNA duplex oligonucleotides in buffers of various magnesium, potassium and Tris ion concentrations and at constant DNA concentration. ($C_T$ = 2 ± 0.2 μM).

| DNA sequence (5' to 3') | [Mon+] (mM) | [Mg$^{2+}$] (mM) | | | | | | | |
|---|---|---|---|---|---|---|---|---|---|
| | | 0 | 0.5 | 1.5 | 3.0 | 10 | 20 | 50 | 125 |
| TTCTACCTATGTGAT (SEQ ID NO: 5) | 1 | — | 43.3 | 46.1 | 47.8 | 50.2 | 50.4 | — | — |
| | 5 | — | 42.1 | 45.6 | 47.6 | 49.5 | 50.4 | 51.0 | 51.5 |
| | 55 | 39.3 | 42.5 | 44.7 | 46.2 | 49.1 | 49.6 | 51.0 | 51.5 |
| | 105 | 43.8 | 44.8 | 45.8 | 47.1 | 49.1 | 50.1 | 51.1 | 51.6 |
| | 205 | 47.7 | — | 48.1 | — | 49.9 | — | 51.1 | 51.4 |
| | 605 | 52.1 | — | 51.9 | — | 51.9 | — | 51.8 | 51.7 |
| | 1005 | 53.2 | — | 53.0 | — | 53.0 | — | 52.0 | 51.4 |
| GCAGTGGATGTGAGA (SEQ ID NO: 12) | 1 | — | 52.3 | 55.1 | 56.5 | 58.1 | 58.7 | — | — |
| | 5 | — | 51.9 | 54.7 | 56.2 | 58.2 | 58.8 | 59.2 | 59.0 |
| | 55 | 49.5 | 52.5 | 54.6 | 56.0 | 58.0 | 58.8 | 59.3 | 59.1 |
| | 105 | 53.8 | 54.6 | 55.8 | 56.6 | 58.2 | 58.9 | 59.4 | 59.4 |
| | 205 | 57.3 | — | 57.9 | — | 59.1 | — | 59.4 | 59.5 |
| | 605 | 61.6 | — | 61.3 | — | 61.1 | — | 60.2 | 59.5 |
| | 1005 | 62.4 | — | 62.3 | — | 61.7 | — | 60.3 | 59.6 |
| CAGCCTCGTCGCAGC (SEQ ID NO: 18) | 1 | — | 61.9 | 64.1 | 65.3 | 66.8 | 67.3 | — | — |
| | 5 | — | 61.1 | 64.2 | 65.1 | 67.2 | 67.5 | 67.5 | 67.3 |
| | 55 | 58.9 | 62.0 | 64.0 | 65.2 | 66.6 | 67.4 | 68.1 | 67.4 |
| | 105 | 63.1 | 63.8 | 65.0 | 65.7 | 67.5 | 67.5 | 67.8 | 67.2 |
| | 205 | 66.5 | — | 67.0 | — | 68.1 | — | 67.6 | 67.3 |
| | 605 | 69.9 | — | 69.8 | — | 69.4 | — | 67.9 | 67.3 |
| | 1005 | 70.6 | — | 70.3 | — | 70.1 | — | 68.1 | 66.9 |
| TGATTCTACCTATGTGATTT (SEQ ID NO: 23) | 1 | — | 51.8 | 54.6 | 55.8 | 57.7 | 58.2 | — | — |
| | 5 | — | 51.0 | 54.5 | 55.8 | 58.1 | 58.5 | 59.3 | 59.5 |
| | 55 | 47.6 | 51.1 | 53.8 | 55.4 | 57.9 | 58.9 | 59.4 | 59.5 |
| | 105 | 51.9 | 53.0 | 54.7 | 55.4 | 57.9 | 58.4 | 59.5 | 59.7 |

TABLE VII-continued

Experimental melting temperatures (° C.) for 12 DNA duplex oligo-
nucleotides in buffers of various magnesium, potassium and Tris
ion concentrations and at constant DNA concentration.
($C_T$ = 2 ± 0.2 µM).

| DNA sequence (5' to 3') | [Mon+] (mM) | [Mg$^{2+}$] (mM) | | | | | | | |
|---|---|---|---|---|---|---|---|---|---|
| | | 0 | 0.5 | 1.5 | 3.0 | 10 | 20 | 50 | 125 |
| | 205 | 56.1 | — | 57.0 | — | 58.7 | — | 59.4 | 59.9 |
| | 605 | 61.6 | — | 61.7 | — | 61.6 | — | 60.7 | 60.3 |
| | 1005 | 63.2 | — | 63.2 | — | 63.0 | — | 61.4 | 60.7 |
| AGCTGCAGTGGATGTGAGAA (SEQ ID NO: 30) | 1 | — | 61.1 | 63.7 | 64.8 | 66.3 | 66.8 | — | — |
| | 5 | — | 60.7 | 63.9 | 65.1 | 66.9 | 67.3 | 67.7 | 67.3 |
| | 55 | 57.8 | 61.1 | 63.2 | 64.6 | 65.8 | 67.1 | 67.8 | 67.5 |
| | 105 | 62.4 | 63.3 | 64.8 | 65.2 | 67.0 | 67.4 | 67.7 | 67.7 |
| | 205 | 66.4 | — | 67.1 | — | 68.1 | — | 67.5 | 67.8 |
| | 605 | 71.2 | — | 71.1 | — | 70.7 | — | 68.7 | 68.2 |
| | 1005 | 72.3 | — | 72.2 | — | 71.7 | — | 69.7 | 68.5 |
| CAGCCTCGTTCGCACAGCCC (SEQ ID NO: 38) | 1 | — | 68.9 | 71.3 | 72.3 | 73.4 | 73.9 | — | — |
| | 5 | — | 68.7 | 71.3 | 72.3 | 73.8 | 74.0 | 74.2 | 73.9 |
| | 55 | 65.0 | 68.7 | 70.8 | 71.9 | 73.2 | 74.0 | 74.2 | 73.8 |
| | 105 | 69.4 | 70.8 | 72.0 | 72.6 | 74.0 | 74.2 | 74.4 | 73.8 |
| | 205 | 73.5 | — | 74.0 | — | 74.8 | — | 74.4 | 73.9 |
| | 605 | 77.6 | — | 77.6 | — | 77.0 | — | 75.2 | 74.2 |
| | 1005 | 78.4 | — | 78.2 | — | 77.5 | — | 75.5 | 74.3 |
| GTTCTATACTCTTGAAGTTGATTAC (SEQ ID NO: 43) | 1 | — | 57.2 | 59.7 | 60.8 | 62.4 | 63.0 | — | — |
| | 5 | — | 56.3 | 59.4 | 60.7 | 62.6 | 63.1 | 63.8 | 64.0 |
| | 55 | 50.7 | 54.6 | 57.5 | 59.1 | 61.5 | 63.0 | 63.8 | 64.2 |
| | 105 | 55.9 | 57.3 | 58.9 | 60.0 | 62.2 | 63.2 | 63.9 | 64.3 |
| | 205 | 60.3 | — | 61.3 | — | 63.1 | — | 63.9 | 64.4 |
| | 605 | 66.1 | — | 66.2 | — | 66.0 | — | 65.2 | 64.9 |
| | 1005 | 68.0 | — | 67.9 | — | 67.5 | — | 66.1 | 65.5 |
| CTGGTCTGGATCTGAGAACTTCAGG (SEQ ID NO: 52) | 1 | — | 65.6 | 67.7 | 68.7 | 69.8 | 70.3 | — | — |
| | 5 | — | 65.1 | 67.6 | 68.5 | 70.1 | 70.3 | 70.7 | 70.6 |
| | 55 | 60.3 | 64.5 | 66.9 | 68.1 | 69.7 | 70.4 | 70.7 | 70.8 |
| | 105 | 64.9 | 66.2 | 68.0 | 68.8 | 70.3 | 70.7 | 71.0 | 70.9 |
| | 205 | 69.1 | — | 70.0 | — | 71.2 | — | 71.1 | 71.0 |
| | 605 | 74.2 | — | 74.1 | — | 74.0 | — | 72.5 | 71.6 |
| | 1005 | 75.8 | — | 75.6 | — | 75.2 | — | 73.2 | 72.3 |
| CAGTGGGCTCCTGGGCGTGCTGGTC (SEQ ID NO: 58) | 1 | — | 73.5 | 75.3 | 76.2 | 77.3 | 77.6 | — | — |
| | 5 | — | 73.3 | 75.9 | 76.6 | 78.0 | 78.0 | 78.2 | 77.4 |
| | 55 | 70.6 | 73.9 | 75.6 | 76.5 | 77.3 | 78.1 | 78.3 | 78.0 |
| | 105 | 74.3 | 75.6 | 77.2 | 77.4 | 78.7 | 78.4 | 78.3 | 77.8 |
| | 205 | 78.2 | — | 79.3 | — | 79.5 | — | 78.2 | 77.8 |
| | 605 | 82.6 | — | 82.6 | — | 81.9 | — | 79.4 | 78.3 |
| | 1005 | 83.4 | — | 83.3 | — | 82.6 | — | 79.8 | 78.4 |
| CTTAAGATATGAGAACTTCAACTAATGTGT (SEQ ID NO: 64) | 1 | — | 61.0 | 63.1 | 64.1 | 65.5 | 66.0 | — | — |
| | 5 | — | 60.5 | 63.2 | 64.4 | 65.9 | 66.4 | 67.1 | 67.1 |
| | 55 | 55.2 | 59.2 | 61.8 | 63.4 | 65.2 | 66.1 | 67.3 | 67.2 |
| | 105 | 60.2 | 61.5 | 63.0 | 64.0 | 66.0 | 66.6 | 67.2 | 67.2 |
| | 205 | 64.6 | — | 65.3 | — | 66.8 | — | 67.0 | 67.3 |
| | 605 | 70.4 | — | 70.4 | — | 70.1 | — | 68.5 | 68.1 |
| | 1005 | 72.4 | — | 72.0 | — | 71.4 | — | 69.6 | 68.5 |
| AGTCTGGTCTGGATCTGAGAACTTCAGGCT (SEQ ID NO: 71) | 1 | — | 69.8 | 71.6 | 72.5 | 73.6 | 73.9 | — | — |
| | 5 | — | 68.8 | 71.6 | 72.3 | 73.8 | 73.9 | 74.2 | 74.4 |
| | 55 | 64.6 | 68.5 | 71.0 | 72.1 | 73.8 | 74.1 | 74.4 | 74.7 |
| | 105 | 68.9 | 70.3 | 72.1 | 73.0 | 74.2 | 74.3 | 74.9 | 74.7 |
| | 205 | 73.2 | — | 74.3 | — | 75.1 | — | 74.7 | 74.9 |
| | 605 | 78.4 | — | 78.2 | — | 78.1 | — | 76.4 | 75.6 |
| | 1005 | 80.1 | — | 79.9 | — | 79.4 | — | 77.2 | 76.2 |
| GACCTGACGTGGACCGCTCCTGGGCGTGGT (SEQ ID NO: 78) | 1 | — | 76.1 | 77.8 | 78.6 | 79.4 | 79.7 | — | — |
| | 5 | — | 75.9 | 78.1 | 79.0 | 79.8 | 79.9 | 80.0 | 79.8 |
| | 55 | 73.2 | 76.5 | 78.0 | 79.0 | 79.5 | 80.0 | 80.3 | 79.6 |
| | 105 | 77.4 | 78.6 | 79.7 | 79.9 | 80.7 | 80.6 | 80.4 | 79.7 |
| | 205 | 81.2 | — | 81.8 | — | 81.8 | — | 80.5 | 79.9 |
| | 605 | 85.6 | — | 85.5 | — | 84.4 | — | 81.9 | 80.6 |
| | 1005 | 86.7 | — | 86.3 | — | 85.2 | — | 82.5 | 81.0 |

Starting from published experimentally measured reference $T_m^0$ values in 1.0 M Na$^+$ buffer (see Owczarzy et al., *Biochemistry* 2004, 43:3537-3554), melting temperatures for the sequences in Tables VI and VII were predicted using the invented algorithms and published algorithms, which were shown earlier in Example 4. Statistical comparisons of the predicted $T_m$ values with the experimentally measured values are reported in Table VIII. Using the method of the invention, it is shown that melting temperatures were predicted with an average error of 0.9° C. or less.

The first row of Table VIII shows the combined results of using the Equation 13 with the data in Tables VI and VII when the coefficients a, d, and g were allowed to vary with [Mon$^+$] (Equations 18-20) when ratio R was from 0.22 to 6.0. The second row of Table VIII shows the combined results of using Equation 13 with the data in Tables VI and VII when the coefficients a, d, and g were set to constant values from Table IIIa. The remaining rows of Table VIII show the results of using Equations 8, 7, and 6, respectively, with the data of Tables VI and VII.

tion. The melting temperature is predicted using Equation 13 in 0.5 mM Mg$^{2+}$, 10 mM Tris-HCl buffer. Since the total monovalent cation concentration is 5 mM Tris$^+$, R= $\sqrt{0.0005}/0.005$=4.47. As the ratio R is larger than 0.22, magnesium ions will exhibit dominant effects on melting temperatures and Equation 13 is accurate under these conditions. However, since R is smaller than 6.0, the most accurate prediction will be obtained when coefficients a, d, g from Equation 16 are calculated according to Equations 18-20.

$a = 3.92 \times 10^{-5}(1 - 0.157 - 0.352\sqrt{0.005} \cdot \ln 0.005) = 3.82 \times 10^{-5}$ $d = 1.42 \times 10^{-5}[1 + 0.279 - 4.03 \times 10^{-3} \ln 0.005 - 8.03 \times 10^{-3} (\ln 0.005)^2] = 1.53 \times 10^{-5}$ $g = 8.31 \times 10^{-5}[1 - 0.514 - 0.258 \ln 0.005 + 5.25 \times 10^{-3}(\ln 0.005)^3] = 8.91 \times 10^{-5}$ The remaining coefficients are taken directly from Table IIIa and entered into Equation 13,

TABLE VIII

Statistical analysis of $T_m$ predictions for data in Tables VI and VII where magnesium and potassium ions compete in their effects on melting temperatures.

| Equations | $T_m$ correction function | Data in buffers containing 50 mM KCl and various [Mg$^{2+}$] from Table VI and VII (n = 484) | | Data from Table VII where both [K$^+$] and [Mg$^{2+}$] vary (n = 456) | |
|---|---|---|---|---|---|
| | | $<\|\Delta T_m\|>_{AVE}$ (° C.) | $\chi_r^2/\nu$ | $<\|\Delta T_m\|>_{AVE}$ (° C.) | $\chi_r^2/\nu$ |
| 13,, 18-20 | This invention (1/$T_m$ correction function, allowing coefficients a, d, and g to vary with [Mon$^+$]) | 0.6 | 6.8 | 0.8 | 10.0 |
| 13 | This invention (1/$T_m$ correction function when coefficients a-g are constant) | 0.8 | 10.7 | 0.9 | 15.3 |
| 8 | Peyret correction | 1.2 | 32.0 | 2.6 | 137.5 |
| 7 | Ahsen et al. correction | 1.5 | 48.5 | 2.9 | 163.1 |
| 6 | Mitsuhashi correction | 2.1 | 77.5 | 3.8 | 250.0 |

Goodness of fit was evaluated from reduced $\chi_r^2$ and from average errors of $T_m$ magnesium predictions $<|\Delta T_m|>_{AVE}$, where $\Delta T_m = T_m$(predicted)$-T_m$(measured) for scaling of $T_m$ from 1M Na$^+$ buffer to magnesium buffers. $\nu$ is the number of degrees of freedom in the fit. The current invention predicts $T_m$ values with the highest accuracy. The most accurate $T_m$ predictions were obtained when coefficients a, d, g were allowed to vary with monovalent ion concentrations. Equations 6, 7, and 8 from the prior art are less accurate because the assumption of additive effects for Mon$^+$ and Mg$^{2+}$ ions is invalid. Since the magnesium and monovalent ions compete in their effects on melting temperatures of oligonucleotides, the effects of Mg$^{2+}$ were not properly modeled.

Example 6

Application of Equations 13 to Calculate Melting Temperature for a DNA Duplex in a Magnesium Solution Below we illustrate the utility of Equation 13 in estimating melting temperature of a 25 base-pair duplex, d(CAGTGGGCTCCTGGGCGTGCTGGTC) with 18 G-C base pairs ($f_{GC}=18/25=0.720$). A reference $T_m^0$ of 83.4° C. was measured in 1M Na$^+$ and 2 µM total single strand concentra- $$\frac{1}{T_m(Mg^{2+})} = \frac{1}{T_m^0} + 3.82 \times 10^{-5} - 9.11 \times 10^{-6} \ln 0.0005 +$$

$$0.72 \times (6.26 \times 10^{-5} + 1.53 \times 10^{-5} \ln 0.0005) + +$$

$$\frac{1}{2(25-1)} \times \begin{bmatrix} -4.82 \times 10^{-4} + 5.25 \times 10^{-4} \ln 0.0005 + \\ 8.91 \times 10^{-5} (\ln 0.0005)^2 \end{bmatrix}$$

$$= \frac{1}{(83.4 + 273.15)} + 8.2851 \times 10^{-5}$$

$$= 2.8875 - 10^{-3} K^{-1}$$

The predicted $T_m(Mg^{2+})$=346.3 K=73.2° C. This value is in excellent agreement with experimentally determined $T_m$ of 73.3° C. under these conditions. Table IX shows comparison of $T_m$ predictions using Equations 8-9 from the prior art. These predictions are significantly less accurate than the $T_m$ prediction from Equation 13 of the present invention.

TABLE IX

Analysis of $T_m$ predictions for a 25 base-pair duplex, d(CAGTGGGCTCCTGGGCGTGCTGGTC) (SEQ ID: 58) in 0.5 mM $MgCl_2$, 10 mM Tris-HCl buffer.

| Equation | Magnesium $T_m$ correction | Predicted $T_m$ (° C.) | Error of prediction (° C.) |
|---|---|---|---|
| 13, 18-20 | This invention ($1/T_m$ correction function, allowing coefficients a, d, and g to vary with [Mon+]) | 73.2 | -0.1 |
| 8 | Peyret correction | 69.9 | -3.4 |
| 7 | Absen et al. correction | 70.6 | -2.7 |
| 6 | Mitsuhashi correction | 66.4 | -6.9 |

Example 7

Implications for PCR and DNA Sequencing

Accurate prediction of $T_m$ in specific reaction conditions is a fundamental step when designing oligodeoxynucleotides for use in PCR, DNA sequencing and other molecular biology applications. $T_m$ prediction is particularly important when working with closely related sequences (allelic variants, single nucleotide polymorphisms, etc.) or when designing multiplex reactions where a large number of primers must function together. We have studied a number of the solution components that can affect DNA duplex stability and therefore impacts the design of DNA primers and probes.

Buffers used in molecular biology experiments generally contain a mixture of monovalent cations ($Na^+$ or $K^+$) and $Mg^{2+}$. As shown in FIG. 6, the effects of sodium and potassium ions on duplex stability are equivalent. This is true even under conditions in which $Na^+$ and $K^+$ compete with $Mg^{2+}$ for binding to DNA. Therefore, nearest-neighbor parameters and salt correction formulas developed for buffers containing $Na^+$ can be used interchangeably with $K^+$.

We have found that the effect of $Mg^{2+}$ on $T_m$ is dominant over monovalent cations under typical reaction conditions used for PCR and DNA sequencing ([$K^+$]=20-100 mM and [$Mg^{2+}$]=1.5-5 mM). Values of R range from about 0.3 to 4 $M^{-1/2}$. Accurate treatment of the effect of $Mg^{2+}$ on $T_m$ is, therefore, very important in the design of DNA primers and probes for these assays. Using the algorithm of FIG. 5 with the correction formulas presented herein, the $T_m$ can be predicted within an average accuracy of 1° C. Earlier models are less accurate and in some cases lead to large errors (>10° C.). The procedure of converting the $Mg^{2+}$ component to an "equivalent $Na^+$ concentration" is not justified. The influence of magnesium and monovalent cations on DNA duplex stability differ both with respect to $f_{GC}$ and oligonucleotide length and must be treated differently.

Figure 7:
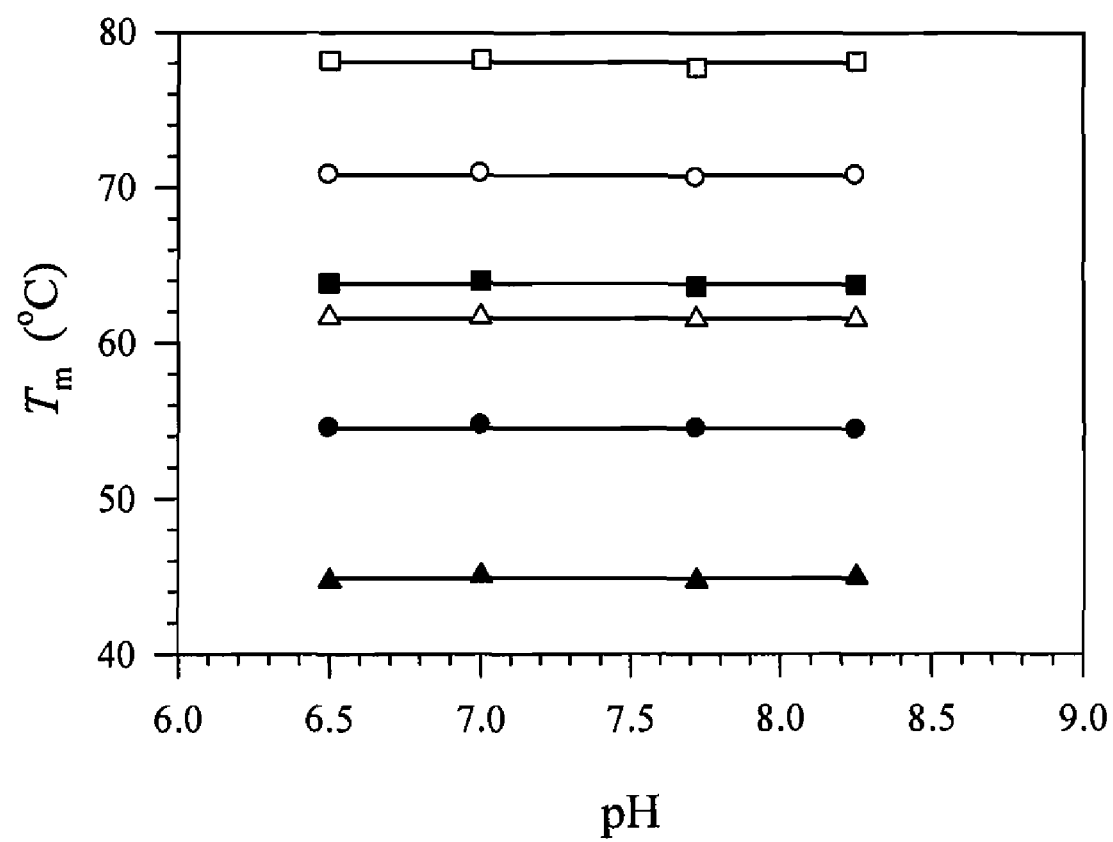
FIG. 7 is a graph that depicts melting temperatures of DNA duplex oligomers in the pH range from 6.5 to 8.3. Solid symbols are 15-mers, open symbols are 30-mers, fraction of G-C base pairs vary from 0.3 to 0.7. Sequences are TTCTAC-CTATGTGAT (SED ID: 5; ▲), GCAGTGGATGTGAGA (SED ID: 12; ●), CAGCCTCGTCGCAGC (SED ID: 8; ■), CTTAAGATATGAGAACTTCAACTAATGTGT (SED ID: 64; △), AGTCTGGTCTGGATCTGAGAACTTCAGGCT (SED ID: 71; ○), GACCTGACGTGGACCGCTC-CTGGGCGTGGT (SED ID: 78; □). Buffers contained 1.5 mM MgCl$_2$, 50 mM KCl and 10 mM cacodylic acid or MOPS.

Although metal ions present in reaction buffers ($Na^+$, $K^+$, $Mg^{2+}$) have the greatest impact on $T_m$, other components contribute and should be taken into account. Most buffers used in molecular biology applications rely on Tris or other ammonium salts, which exhibit a significant dependence of ionization constant on temperature. Tris buffer adjusted to pH of 8.3 at 25° C. decreases to pH 6.9 as temperature is raised to 95° C. This pH change, however, has little effect on the stability of DNA duplexes (see FIG. 7) as $pK_H$s of the ionizable groups of the bases lie outside of this range. Nucleic acid bases have $pK_H$ values lower than 4.5 (dC) and greater than 9.4 (dG) in the single-stranded state which move even further from neutrality in the duplex state (Record. *Biopolymers* 1967, 5:993-1008). Furthermore, the temperature range where primer hybridization and DNA synthesis occur during PCR is usually between 60° C. (the primer annealing step) and 72° C. (the enzymatic extension step). Within this narrow temperature window, pH varies only between 7.6 and 7.4. Thus the large pH shifts seen in Tris buffers with changes in temperature should have no effect on hybridization efficiency during PCR or other thermal cycling reactions. However, the protonated form of Tris is a monovalent cation and should be added to the total monovalent cation concentration when performing $T_m$ calculations. Due to the relative extent of ionization, 10 mM Tris is equivalent to about 5 mM $Na^+$.

Figure 8:
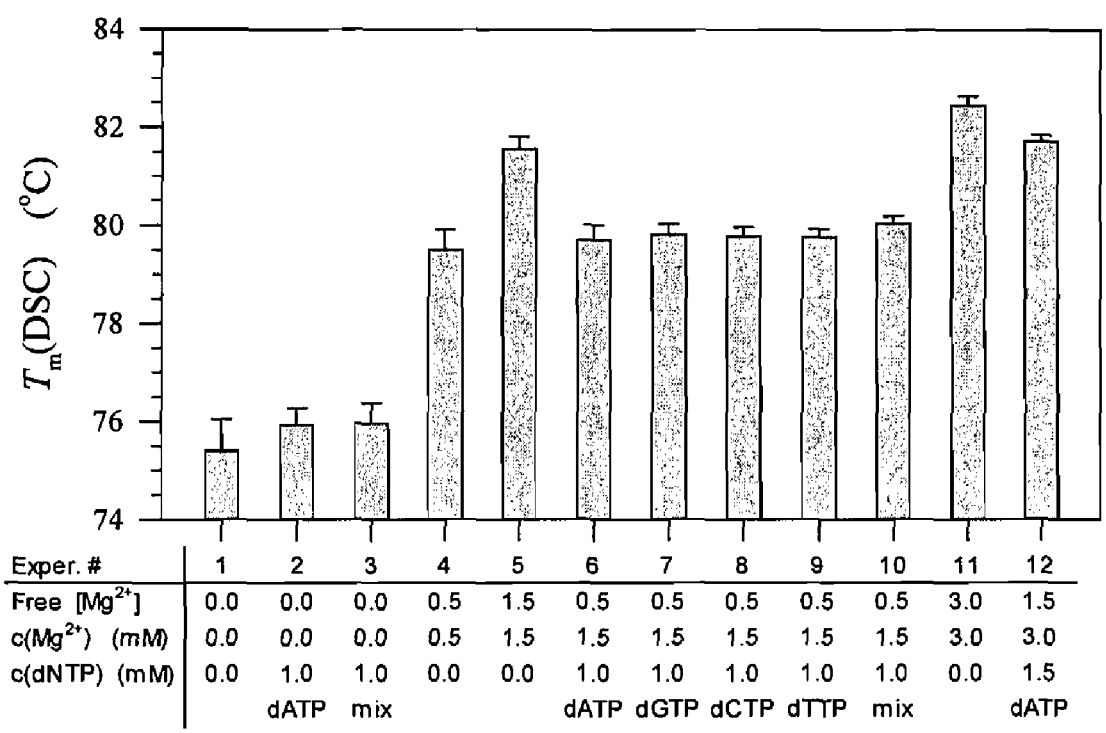
FIG. 8 displays experimental melting temperatures of the 60-mer duplex 5'-TTCGCGGATTAGCCCTACGCATCG-GTTACAAACGAGGACCTTATGCAC TTTGACAG-CATG-3', SEQ ID NO: 93, that were obtained using DSC at low DNA concentration ($C_t$=2 μM). Buffers contained 50 mM KCl, 10 mM Tris-HCl (pH=8.3) and various amounts of magnesium ions and deoxynucleotide triphosphates. Concentrations (mM) used in each experiment are indicated below the graph. The first row is the free [Mg$^{2+}$], which is calculated as the difference between total Mg$^{2+}$ and dNTP concentrations. dNTP "mix" contained equimolar concentrations of dATP, dGTP, dCTP and dTTP. The sum of their concentrations is shown in the table below the graph.

The binding of magnesium to dNTPs in a reaction mixture decreases the free magnesium ion concentration, which, in turn, lowers the $T_m$ for DNA hybridization reactions done in that buffer. As shown by the results in FIG. 8, the Mg-dNTP binding constant is sufficiently large (Sigel. *Chem. Soc. Rev.* I 1993, 22:255-267) that the free $Mg^{2+}$ concentration can be approximated simply by the difference between the total magnesium concentration and the total concentration of dNTPs. In a typical PCR reaction, the four dNTPs together are usually present at a concentration of 0.8 mM. If the total concentration of the magnesium were 3.0 mM, the free concentration of the Mg2+ used in conjunction with the algorithms and formulae of the present invention would be 2.2 mM.

REFERENCES CITED

Numerous references, including patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entirety and to the same extent as if each reference was individually incorporated by reference.

We claim:

1. A method for estimating a melting temperature, $T_m(X^{2+})$, for a polynucleotide having a known G-C content value, $f_{GC}$, at a desired divalent ion concentration, $[X^{2+}]$, and an optionally present monovalent cation concentration $[Mon^+]$, the method carried out by a computer system executing instructions contained in at least one memory, the method comprising:

(a) the computer system receiving a reference melting temperature, $T_m^o$, for the polynucleotide, said reference melting temperature being a melting temperature obtained or provided for the polynucleotide at a reference monovalent ion concentration, $[Mon^{+o}]$; and (b) the computer system generating the melting temperature of the polypeptide at the desired monovalent and divalent cation concentrations by modifying said reference melting temperature, or reciprocal of said melting temperature, by one or more terms which are a function of fGC $f_{GC}$;

wherein the reciprocal of the reference melting temperature is modified by adding a term comprising:

$$a + b\ln[X^{2+}] + f_{GC} \cdot (c + d\ln[X^{2+}])$$

wherein each of the coefficients a, b, c, and d is optimized for predicting polynucleotide melting temperatures.

2. The method of claim 1, wherein the melting temperature, $T_m(X^{2+})$, is estimated according to a formula comprising:

$$\frac{1}{T_m(X^{2+})} = \frac{1}{T_m^o(Mon_0^+)} + a + b\ln[X^{2+}] + f_{GC} \cdot (c + d\ln[X^{2+}])$$

wherein each of the coefficients a, b, c, and d is optimized for predicting polynucleotide melting temperatures.

3. The method of claim 1, wherein the melting temperature, $T_m(X^{2+})$, is estimated according to a formula comprising:

$$\frac{1}{T_m(X^{2+})} = \frac{1}{T_m^o(Mon_o^+)} + a + b \cdot \ln[X^{2+}] + f_{GC} \cdot (c + d \cdot \ln[X^{2+}]) + \left(\frac{e + f \cdot \ln[X^{2+}]}{2 \cdot (N_{bp} - 1)}\right)$$

wherein $N_{bp}$ is the number of base pairs in the polynucleotide, and wherein each of the coefficients a, b, c, d, e, and f is optimized for predicting polynucleotide melting temperatures.

4. The method of claim 1, wherein the melting temperature, $T_m(X^{2+})$, is estimated according to a formula comprising:

$$\frac{1}{T_m(X^{2+})} = \frac{1}{T_m^o(Mon_o^+)} + a + b \cdot \ln[X^{2+}] + f_{GC} \cdot \left(\frac{c + d \cdot}{\ln[X^{2+}]}\right) + \frac{e + f \cdot \ln[X^{2+}] + g \cdot (\ln[X^{2+}])^2}{2 \cdot (N_{bp} - 1)}$$

wherein $N_{bp}$ is the number of base pairs in the polynucleotide, and wherein each of the coefficients a, b, c, d, e, f, and g is optimized for predicting polynucleotide melting temperatures.

5. The method of claim 4, wherein the reciprocal of the reference melting temperature is further modified by adding one or more additional terms $$\frac{q \cdot (\ln[X^{2+}])^p}{2 \cdot (N_{bp} - 1)}$$

wherein $N_{bp}$ is the number of base pairs in the polynucleotide, wherein p is an integer, and q is a coefficient which is is optimized for predicting polynucleotide melting temperatures, and wherein one or more such terms may be added to the formula, and wherein p and q may be unique for each additional added term.

6. The method of claim 1, wherein the reference melting temperature is modified by adding a term comprising:

$$a' + b' \cdot \ln[X^{2+}] + f_{GC} \cdot (c' + d' \ln[X^{2+}]),$$

wherein each of the coefficients a', b', c', and d' is optimized for predicting polynucleotide melting temperatures.

7. The method of claim 6, wherein the melting temperature, $T_m(X^{2+})$, is estimated according to a formula comprising:

$$T_m(X^{2+}) = T_m^o + a' + b' \cdot \ln[X^{2+}] + f_{GC} \cdot (c' + d' \ln[X^{2+}])$$

wherein each of the coefficients a', b', c', and d' is optimized for predicting polynucleotide melting temperatures.

8. The method of claim 1, wherein the melting temperature, $T_m(X^{2+})$, is estimated according to a formula comprising:

$$T_m(X^{2+}) = T_m^o + a' + b' \cdot \ln[X^{2+}] + f_{GC} \cdot \left(\frac{c' + d' \cdot}{\ln[X^{2+}]}\right) + \frac{e' + f' \cdot \ln[X^{2+}]}{2 \cdot (N_{bp} - 1)}$$

wherein $N_{bp}$ is the number of base pairs in the polynucleotide, and wherein each of the coefficients a', b', c', d', e', and f' is optimized for predicting polynucleotide melting temperatures.

9. The method of claim 1, wherein the melting temperature, $T_m(X^{2+})$, is estimated according to a formula comprising:

$$T_m(X^{2+}) = T_m^o + a' + b' \cdot \ln[X^{2+}] + f_{GC} \cdot \left(\frac{c' + d' \cdot}{\ln[X^{2+}]}\right) + \frac{e' + f' \cdot \ln[X^{2+}] + g' \cdot (\ln[X^{2+}])^2}{2 \cdot (N_{bp} - 1)}$$

wherein $N_{bp}$ is the number of base pairs in the polynucleotide, and wherein each of the coefficients a', b', c', d', e', f', and g' is optimized for predicting polynucleotide melting temperatures.

10. The method of claim 9, wherein the reference melting temperature is further modified by adding one or more additional terms $$\frac{q \cdot (\ln[X^{2+}])^p}{2 \cdot (N_{bp} - 1)}$$

wherein $N_{bp}$ is the number of base pairs in the polynucleotide, wherein p is an integer, and q is a coefficient which is optimized for predicting polynucleotide melting temperatures, and wherein p and q may be unique for each additional added term.

11. The method of claim 4, wherein the coefficients a, b, c, d, e, f, and g are $3.92 \times 10^{-5} K^{-1}$, $-9.11 \times 10^{-6} K^{-1}$, $6.26 \times 10^{-5} K^{-1}$, $1.42 \times 10^{-5} K^{-1}$, $-4.82 \times 10^{-4} K^{-1}$, $5.25 \times 10^{-4} K^{-1}$, $8.31 \times 10^{-5} K^{-1}$ respectively and wherein the reference monovalent ion concentration, $[Mon^{-0}]$, is about 1 M.

12. The method of claim 9, wherein the coefficients a', b', c', d', e', f', and g' are $-4.59$ K, $1.06$ K, $-7.26$ K, $-1.34$ K, $63.3$ K, $-60.4$ K, and $-8.78$ K respectively, and wherein the reference monovalent ion concentration, $[Mon^+_o]$, is about 1 M.

13. The method of claim 1, further comprising:
(a) the computer system calculating the ratio R of free divalent ion, $[X^{2+}]$, and monovalent ion, $[Mon^-]$, concentrations, $$R = \frac{\sqrt{[X^{2+}]}}{[Mon^+]}; \text{ and}$$

(b) the computer system comparing the ratio R to one or more limiting values.

14. The method of claim 13, wherein R is compared to the limiting values $0.22$ $M^{-1/2}$ and $6.0$ $M^{-1/2}$.

15. The methods of claim 4 wherein the coefficients are allowed to vary with monovalent cation concentration, $[Mon^+]$.

16. The methods of claim 4, wherein the coefficient a is calculated according to formula $a = 3.92 \times 10^{-5}(1 - 0.157 - 0.352\sqrt{[Mon^+]} \cdot \ln[Mon^+])$, the coefficient d is calculated according to formula $d=1.42\times10^{-5}(1+0.279-4.03\times10^{-3} \ln[Mon^+]-8.03\times10^{-3} \ln^2[Mon^+])$, the coefficient g is calculated according to formula $g=8.31\times10^{-5}(1-0.514-0.258 \ln[Mon^+]+5.25\times10^{-3} \ln^3[Mon^+])$, and wherein the reference monovalent ion concentration, $[Mon^+_0]$, is about 1 M.

17. The method of claim 1, wherein the monovalent ion is selected from the group consisting of Tris ions, ammonium ions ($NH_4^+$), lithium ions ($Li^+$), sodium ions ($Na^{30}$), potassium ions ($K^+$), rubidium ions ($Rb^+$), cesium ions ($Cs^+$), and francium ions ($Fr^+$).

18. The method of claim 1, wherein the divalent ion is selected From the group consisting of magnesium ions ($Mg^{2+}$), manganese ions ($Mn^{2+}$) and calcium ions ($Ca^{2+}$).

19. The method of claim 1, wherein the polynucleotide is DNA.

20. The method of claim 1, wherein the polynucleotide ranges in length from about 8 to about 500 base pairs.

21. The method of claim 12, wherein the polynucleotide ranges from about 10 to about 30 base pairs in length.

22. The method of claim 1, wherein the reference melting temperature is experimentally determined, calculated from a theoretical model, and/or calculated from a nearest neighbor model.

23. The method of claim 1, wherein the reference ion concentration is about 1 M.

24. The method of claim 1, wherein the divalent cation concentration ranges between about 0.1 mM and about 1 M.

25. The method of claim 1, wherein the presence of compounds that bind to the divalent cation is subtracted from the divalent cation concentration through the formula:

$$[X^{2+}]=c(X^{2+})-c(\text{binding compound})\times(\text{no. of } X^{2+} \text{ ions bound per binding compound}).$$

26. A computer system for predicting a melting temperature, which computer system comprises:
  (a) a memory: and
  (b) a processor interconnected with the memory and having one or more software components loaded therein,
wherein the one or more software components cause the processor to execute steps of a method according to claim 1.

27. A computer program product comprising a computer readable medium having one or more software components encoded thereon in computer readable form, wherein the one or more software components may be loaded into a memory of a computer system and cause a processor interconnected with said memory to execute steps of a method according to claim 1.

* * * * *